United States Patent
Landry et al.

(10) Patent No.: US 8,318,156 B2
(45) Date of Patent: Nov. 27, 2012

(54) ANTI-COCAINE COMPOSITIONS AND TREATMENT

(75) Inventors: Donald W Landry, New York, NY (US); Joanne MacDonald, New York, NY (US); Shi-Xian Deng, White Plains, NY (US); Chang-Guo Zhan, Lexington, KY (US); Daquan Gao, Louisville, KY (US); James H. Woods, Ann Arbor, MI (US); Roger K. Sunahara, Ann Arbor, MI (US); Diwahar L. Narasimhan, Ann Arbor, MI (US); Victor Yang, Ann Arbor, MI (US); Mei-Chuan Holden Ko, Ann Arbor, MI (US); John J. Tesmer, Ann Arbor, MI (US); Tien-Yi Lee, Ann Arbor, MI (US); Young Min Kwon, Ann Arbor, MI (US)

(73) Assignees: The Trustees of Columbia University in the City of New York, New York, NY (US); The Regents of the University of Michigan, Ann Arbor, MI (US); University of Kentucky Research Foundation, Lexington, KY (US)

( * ) Notice: Subject to any disclaimer, the term of this patent is extended or adjusted under 35 U.S.C. 154(b) by 585 days.

(21) Appl. No.: 12/373,510

(22) PCT Filed: Jul. 10, 2007

(86) PCT No.: PCT/US2007/015762
§ 371 (c)(1),
(2), (4) Date: Oct. 2, 2009

(87) PCT Pub. No.: WO2008/008358
PCT Pub. Date: Jan. 17, 2008

(65) Prior Publication Data
US 2010/0034799 A1      Feb. 11, 2010

Related U.S. Application Data

(60) Provisional application No. 60/819,569, filed on Jul. 10, 2006.

(51) Int. Cl.
*A61K 38/46* (2006.01)
*A61K 38/43* (2006.01)
*C12N 9/16* (2006.01)
*C12N 9/14* (2006.01)
*C12P 21/06* (2006.01)
*C12P 19/34* (2006.01)
*C07H 21/04* (2006.01)

(52) U.S. Cl. ...... 424/94.6; 424/94.1; 435/196; 435/195; 435/69.1; 435/91.1; 536/23.1; 536/23.2; 530/350

(58) Field of Classification Search ................ 424/94.6, 424/94.1; 435/196, 195, 69.1, 91.1; 536/23.1, 536/23.2; 530/350
See application file for complete search history.

(56) References Cited

U.S. PATENT DOCUMENTS

| 5,462,868 A | 10/1995 | Britt et al. |
| 5,730,985 A | 3/1998 | Barber et al. |
| 5,977,314 A | 11/1999 | Landry et al. |
| 2002/0048271 A1 | 4/2002 | Rastinejad et al. |
| 2011/0142816 A1* | 6/2011 | Landry et al. ............... 424/94.6 |

FOREIGN PATENT DOCUMENTS

| GB | 2257972 | 1/1993 |
| WO | WO 2008/008358 | 1/2008 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Wishart et al., A single mutation converts a novel phosphotyrosine binding domain into a dual-specificity phosphatase. J. Biol. Chem., 1995, vol. 270(45): 26782-26785.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Supplemental European Search Report issued in the related application No. EP07810316 on Jan. 13, 2010.
Marshall et al., Rational Design and Engineering of Therapeutic Proteins, Drug Discovery Today, 2003, pp. 212-221, vol. 8, No. 5.
Ascenzi et al, The *Rhodococcus* sp. Cocaine Esterase: A Bacterial Candidate for Novel Pharmacokinetic-based Therapies for Cocaine Abuse, IUBMB Life, Jul. 2003, pp. 397-402, vol. 55, No. 7.
Baird et al, Natural and Artificial Enzymes Against Cocaine. I. Monoclonal Antibody 15A10 and the Reinforcing Effects of Cocaine in Rats. J. Pharmacol. Exp. Ther., 2000, pp. 1127-1134, vol. 295, No. 3.

(Continued)

*Primary Examiner* — Ganapathirama Raghu
(74) *Attorney, Agent, or Firm* — SNR Denton US LLP

(57) ABSTRACT

Embodiments of the invention disclosed herein generally relate to anti-cocaine therapeutics. Specifically, some embodiments of the invention relate to highly efficient, thermostable, and long-lasting cocaine esterase (CocE) mutants that can protect against the toxic and reinforcing effects of cocaine in subjects. Provided herein are mutant CocE polypeptides displaying thermostable esterase activity. Also provided are methods of treating cocaine-induced conditions in a subject in need via administration of mutant CocE as well as methods for high-throughput screening of candidate esterase polypeptides.

20 Claims, 36 Drawing Sheets

OTHER PUBLICATIONS

Bresler et al, Gene Cloning and Nucleotide Sequencing and Properties of a Cocaine Esterase from *Rhodococcus* sp. strain MB1. Appl. Environ. Microbiol., Mar. 2000, pp. 904-908, vol. 66, No. 3.

Britt et al, Identification of a Cocaine Esterase in a Strain of *Pseudomonas maltophilia*. Journal of Bacteriology, 1992, pp. 2087-2094, vol. 174, No. 7.

Browne et al, The Influence of Plasma Butyrylcholinesterase Concentration on the in Vitro Hydrolysis of Cocaine in Human Plasma, 1998, Biopharm. Drug Dispos., 1998, pp. 309-314, vol. 19.

Carmona et al, Butyrylcholinesterase Accelerates Cocaine Metabolism: In Vitro and In Vivo Effects in Nonhuman Primates and Humans. Drug Metab. Dispos., 2000, pp. 367-371, vol. 28, No. 3.

Carmona et al, Attenuation of Cocaine-Induced Locomotor Activity by Butyrylcholinesterase, Exp. Clin. Psychopharmacol., 1998, pp. 274-279, vol. 6, No. 3.

Carmona et al. Plasma Butyrylcholinesterase Activity and Cocaine Half-Life Differ Significantly in Rhesus and Squirrel Monkeys. Life Sci., 1996, pp. 939-943, vol. 59, No. 11.

Carroll et al, Pharmacotherapies for Treatment of Cocaine Abuse: Preclinical Aspects. J. Med. Chem., Jul. 29, 1999, pp. 2721-2736, vol. 42, No. 15.

Cooper et al, Inhibition of cocaine toxicity by cocaine esterase in the rat. FASEB Journal, 2005, p. A512, abstract No. 311.6.

Cooper et al. Rapid and Robust Protection Against Cocaine-Induced Lethality in Rats by the Bacterial Cocaine Esterase, Mol. Pharmacol., 2006, pp. 1885-1891, vol. 70, No. 6.

Cooper et al, Cocaine Esterase Blocks Cocaine-Induced Seizures and Cardiovascular Effects in the Rat, FASEB Journal, 2005, p. A512, abstract No. 311.7.

Deng et al, Anticocaine Catalytic Antibodies, J. Immunol. Methods, 2002, pp. 299-310, vol. 269.

Duysen et al, Wild-type and A328W Mutant Human Butyrylcholinesterase Tetramers Expressed in Chinese Hamster Ovary Cells have a 16-Hour Half-Life in the Circulation and Protect Mice from Cocaine Toxicity, J. Pharmacol. Exp. Ther., 2002, pp. 751-758, vol. 302, No. 2.

Flores and Ellington, Increasing The Thermal Stability of an Oligomeric Protein, Beta-Glucuronidase, Journal of Molecular Biology, 2002, pp. 325-337, vol. 315.

Gao and Brimijoin, An engineered cocaine hydrolase blunts and reverses cardiovascular responses to cocaine in rats. J. Pharmacol. Exp. Ther., 2004, pp. 1046-1052, vol. 310, No. 3.

Gao et al, Gene Transfer of Cocaine Hydrolase Suppresses Cardiovascular Responses to Cocaine in Rats, Molecular Pharmacology, 2005, pp. 204-211, vol. 67, No. 1.

Gorelick, Enhancing Cocaine Metabolism with Butyrylcholinesterase as a Treatment Strategy, Drug Alcohol Depend., 1997, pp. 159-165, vol. 48.

Harris and Chess, Effect of Pegylation on Pharmaceuticals, Nature Reviews. Drug Discovery, Mar. 2003, pp. 214-221, vol. 2.

Harris et al, Pegylation: A Novel Process for Modifying Pharmacokinetics, Clinical Pharmacokinetics, 2001, pp. 539-551, vol. 40, No. 7.

Hoffman et al, Administration of Purified Human Plasma Cholinesterase Protects against Cocaine Toxicity in Mice, J. Toxicol. Clin. Toxicol., May 1996, pp. 259-266, vol. 34, No. 3.

Kim et al, Directed Evolution of Thermus Maltogenic Amylase Toward Enhanced Thermal Resistance, Applied Environmental Microbiology, May 2003, pp. 4866-4874, vol. 69, No. 8.

Ko et al. Cocaine Esterase: Interactions with Cocaine and Immune Responses in Mice, J. Pharmacol. Exp. Ther., 2007, pp. 926-933, vol. 320, No. 2.

Koetzner and Woods, Characterization of Butyrylcholinesterase Antagonism of Cocaine-Induced Hyperactivity, Drug Metab. Dispos., 2002, pp. 716-723, vol. 30, No. 6.

Korkegian et al. Computational Thermostabilization of an Enzyme, Science, May 6, 2005, pp. 857-860, vol. 308.

Landry et al, Antibody-Catalyzed Degradation of Cocaine, Science, Mar. 26, 1993, pp. 1899-1901, vol. 259.

Larsen et al, Crystal Structure of a Bacterial Cocaine Esterase, Nature Struct. Biol., Jan. 2002, pp. 17-21, vol. 9, No. 1.

Larsen et al, Crystallographic and Biochemical Analysis of Cocaine-Degrading Antibody 15A10, Biochemistry, 2004, pp. 8067-8076, vol. 43.

Lehmann and Wyss, Engineering Proteins for Therrnostability: The Use of Sequence Alignments Versus Rational Design and Directed Evolution, Current Opinion in Biotechnology, 2001, pp. 371-375, vol. 12.

Lopez-Camacho et al, Amino Acid Substitutions Enhancing Thermostability of *Bacillus* Polymyxa Beta-Glucosidase A, Biochemistry Journal, 1996, pp. 833-838, vol. 314.

Lynch et al, Cocaine Detoxification by Human Plasma Butyrylcholinesterase, Toxicol. Appl. Pharmacol., 1997, pp. 363-371, vol. 145.

Mattes et al, Therapeutic Use of Butyrylcholinesterase for Cocaine Intoxication, Toxicol. Appl. Pharmacol., 1997, pp. 372-380, vol. 145.

Mets et al, A Catalytic Antibody Against Cocaine Prevents Cocaine's Reinforcing and Toxic Effects in Rats, Proc. Natl. Acad. Sci., Aug. 1998, pp. 10176-10181, vol. 95.

Miyazaki et al, Directed Evolution Study of Temperature Adaptation in a Psychrophilic Enzyme, Journal of Molecular Biology, 2000, pp. 1015-1026, vol. 297.

Norman et al. A Chimeric Human/Murine Anticocaine Monoclonal Antibody Inhibits the Distribution of Cocaine to the Brain in Mice, J. Pharmacol. Exp. Ther., 2007, pp. 145-153, vol. 320, No. 1.

Pan et al, Computational Redesign of Human Butyrylcholinesterase for Anticocaine Medication, Proc. Natl. Acad. Sci., Nov. 15, 2005, pp. 16656-16661, vol. 102, No. 46.

Pancook et al, Application of Directed Evolution Technology to Optimize the Cocaine Hydrolase Activity of Human Butyrylcholinesterase, FASEB Journal, 2003, p. A565, abstract No. 364.9.

Rogers et al, Towards Cocaine Esterase Therapeutics, J. Am. Chem. Soc., Jul. 20, 2005, pp. 10016-10017, vol. 127, No. 28.

Scandurra et al, Protein Thermostability in Extremophiles. Biochimie, 1998, pp. 933-941, vol. 80.

Sun et al, Cocaine Metabolism Accelerated by a Re-Engineered Human Butyrylcholinesterase, J. Pharmacol. Exp. Ther., 2002, pp. 710-716, vol. 302, No. 2.

Sun et al, Re-Engineering Butyrylcholinesterase as a Cocaine Hydrolase, Molecular Pharmacology, 2002, pp. 220-224, vol. 62, No. 2.

Turner et al, Biochemical Characterization and Structural Analysis of a Highly Proficient Cocaine Esterase, Biochemistry, 2002, pp. 12297-12307, vol. 41.

Uchiyama et al, Directed Evolution to Improve the Thermostability of Prolyl Endopeptidase, Journal of Biochemistry, 2000, pp. 441-447, vol. 128, Tokyo.

Veronese and Harris, Introduction and Overview of Peptide and Protein Pegylation, Advanced Drug Delivery Reviews, 2002, pp. 453-456, vol. 54.

White et al, Improved Thermostability of the North American Firefly Luciferase: Saturation Mutagenesis at Position 354, Biochemistry Journal, 1996, pp. 343-350, vol. 319.

Xie et al, An Improved Cocaine Hydrolase: The A328Y Mutant of Human Butyrylcholinesterase is 4-Fold more Efficient, Mol. Pharmacol., 1999, pp. 83-91, vol. 55.

Zhan et al, Fundamental Reaction Mechanism for Cocaine Hydrolysis in Human Butyrylcholinesterase, Journal of the American Chemical Society, 2003, pp. 2462-2474, vol. 125.

Chinese Office Action dated Jun. 1, 2011 in related Application No. 200780033496, includes English translation, 10 pages.

International Search Report and Written Opinion dated Feb. 9, 2009 in corresponding PCT Application No. PCT/US/2008/069659 filed Jul. 10, 2008, 11 pages.

International Search Report and Written Opinion dated Sep. 29, 2008 in related PCT Application No. PCT/US07/15762 filed Jul. 10, 2007, 6 pages.

Malaysian Official Action and Search Report dated Feb. 15, 2012 in related Application No. PI 20090140 filed Jul. 10, 2007, 3 pages.

New Zealand Official Action dated Jun. 14, 2010 in related Application No. 574376 filed Jul. 10, 2007, 3 pages.

New Zealand Official Action dated Nov. 15, 2010 in related Application No. 582626 filed Jul. 10, 2008, 2 pages.

Supplementary European Search Report dated Sep. 1, 2011 in related Application No. EP08781619.5 filed Jul. 10, 2008, 10 pages.

* cited by examiner

A

B

SEQUENCE LISTING

```
<160> NUMBER OF SEQ ID NOS: 47

<210> SEQ ID NO 1
<211> LENGTH: 574
<212> TYPE: PRT
<213> ORGANISM: Rhodococcus sp. MB1

<400> SEQUENCE: 1

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
        50                  55                  60
```

-continued

```
Asp Gly Tyr Ala Val Val Ile Gln Asp Thr Arg Gly Leu Phe Ala Ser
 65                  70                  75                  80

Glu Gly Glu Phe Val Pro His Val Asp Glu Ala Asp Ala Glu Asp
             85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
            115                 120                 125

Ser Gly Val Gly Gly Leu Lys Ala Ile Ala Pro Ser Met Ala Ser Ala
            130                 135                 140

Asp Leu Tyr Arg Ala Pro Trp Tyr Gly Pro Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ser Val Thr Pro Leu
            195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
            275                 280                 285

Asn Leu Thr Gly Arg Asn Ala Asp Arg Lys Phe Gly Ile Ala Ala Thr
            290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
            355                 360                 365

Ala Asn Thr Ser Thr Gly Gly Thr Leu Ser Thr Ser Ile Ser Gly
            370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
            435                 440                 445

Leu Phe Val Ser Ser Ala Val Asp Thr Phe Thr Ala Lys Leu
450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495
```

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
            515                 520                 525

Phe Pro Lys Tyr Asp Arg Asn Ser Asn Thr Gly Val Ile Ala Arg
            530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 2
<211> LENGTH: 2692
<212> TYPE: DNA
<213> ORGANISM: Rhodococcus sp. MB1

<400> SEQUENCE: 2

```
gatccagcga aggtcgggag tgaatggtgg acgggaatta cagtgttgcc tcgaacgtga        60
tggttccgat gcgtgatggg gtgcgtctgc cggtcgacct gtaccgacca gatgctgatg       120
gacctgttcc ggtcctgctg gttcgcaacc catacgacaa gttcgacgtg ttcgcgtggt       180
cgacgcagtc gacaaactgg cttgagttcg tgcgtgatgg ctatgccgtg gtcattcaag       240
acacgcgtgg cttgttcgca tcggaaggtg agttcgtccc gcacgttgac gacgaagctg       300
acgccgagga tacgttgagc tggattctgg aacaagcgtg gtgcgacggc aatgtgggca       360
tgttcggcgt ttcgtacttg ggtgtgaccc agtggcaggc cgccgtatcc ggcgttggtg       420
ggctgaaggc gatcgcgccg tccatggcgt cggcggactt gtaccgcgcc cgtggtacg        480
gccctggtgg tgcgctttca gtcgaggcgc tgttgggctg gtcagctctc ataggtactg       540
ggctcatcac gtcgaggtct gacgcccggc ccgaagacgc agccgacttc gtccaactcg       600
cagcaattct caatgacgtc gctggcgcgg cgtcggtcac gccccctggcc gagcaaccgc      660
ttctgggccg actgattccg tgggtgatcg atcaggttgt cgatcacccc gacaacgatg       720
aatcatggca gtccattagc ttgtttgaac gactcggcgg gttggcaaca ccggccttga       780
tcacggctgg gtggtacgac gggttcgtcg gcgaatcgtt gcgcactttc gttgcggtca       840
aggacaatgc cgacgcacgt ttggttgtcg gcccttggag tcacagcaac ctcactggtc       900
ggaatgcgga ccggaagttc ggcattgccg cgacctaccc gattcaagaa gccaccacga       960
tgcacaaggc attcttcgac cggcacctcc gcggcgagac cgatgcactc gcaggcgtcc      1020
ccaaagtgcg gctgttcgta atgggcatcg atgagtggcg tgacgaaacg gactggccac      1080
tgccggacac ggcgtatacg cccttctatc ttggaggtag cggggctgcg aatacctcca      1140
cgggtggtgg aacactgtcg acgtcgattt ccggaactga atctgctgac acctacctgt      1200
atgatccggc cgatcccgtg ccttcgctcg ggggacgct gctgttccac aacgagacga      1260
acggacccgc cgaccaacgt cccattcatg accgggacga cgttgttgtgt tacagcactg      1320
aggtattgac cgacccggtg gaagtaaccg gcaccgtctc cgcccggctg ttcgtgtcgt      1380
catcagcggt ggacactgat ttcaccgcca aacttgtcga cgtatttccc gacggtcgcg      1440
cgatcgcgct gtgtgacggg atcgtgcgga tgcggtaccg cgagacgttg gtcaatccaa      1500
ccttgatcga agcgggcgaa atctacgagg ttgctatcga catgcttgca acctcgaatg      1560
tattcctgcc agggcatcgc atcatggtcc aagtatcaag tagcaacttc ccgaaatacg      1620
accgcaattc gaataccggc ggagtaatcg cacgggaaca gctcgaagag atgtgcaccg      1680
```

-continued

```
ccgtgaaccg cattcaccga ggacctgagc atcccagcca cattgtgctg ccgattatca   1740
agcgatagtt ttcggtgcag ccgcgcctgg ctgacgctgc agctcaaacc caatggctcg   1800
gcaaccggta cgcgctcgcc gccctgcact ttccaccatg cgtaggtcgt cagcggccga   1860
ctgaaggccg gattgcatcc cgacccggcg accctaggtc aggcgaattg tccgaatgtc   1920
agcggtcatg taattcccca ggttgagcgg ttcgtcggtc acgtaattcc tcaccctgcc   1980
gtcacgtagt tccccaccct gggcgtgtcg gtcggggtgc gggtgctgct gcaggttcgc   2040
cccctcccaa ggtccacctg ggaaggggc ccgacggtgg caaggagaac gtggacgatg    2100
accgatctga cgatgaccga tctgatggag ttcttccggc actggcatgc cgggcgttcg   2160
caggttcaga tctcaccggc gtttgggatc gaccgcaaaa cctgacttgc acaagttgac   2220
ggcggtttcc ggactcggct gacatttgcg caagtagaag gccccgcggg ttcgggattt   2280
ggcgcactaa cgggtcggta aatctggcg agtggcggcg tacattcgca aggtcaggac   2340
cgcatcgggg gcgaccgcgg tgcagatcgc cgtcaagcag gacgtcgcg acaaggtgcg    2400 tcgagcacct cggttccgca cacaccgaca gcgagcttgc tgcgctactg caggccgccg   2460 aggaaagct gcaggtcgga cagtaggaac tcgacctcga cctcggcggt agcggggatc    2520
gagggtcggt gatcgcggcg aagcggtccc gctggttgat cgaggcgatc gagaccggat   2580
gacggcggct cggcttcgac gtgatcgacg acgaggtgtt catctaactg gtgatcggca   2640
ggctcgtcga accgacctcg atgagcgaca ccggccggga atcgccgaga tc           2692
```

<210> SEQ ID NO 3
<211> LENGTH: 574
<212> TYPE: PRT
<213> ORGANISM: Artificial
<220> FEATURE:
<223> OTHER INFORMATION: Mutant CocE polypeptide

<400> SEQUENCE: 3

```
Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
    130                 135                 140

Asp Leu Tyr Arg Ala Pro Trp Tyr Gly Pro Gly Gly Ala Leu Ser Val
145                 150                 155                 160

Glu Ala Val Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190
```

Ala Ala Ile Leu Asn Asp Val Ala Gly Ala Ser Val Thr Pro Leu
        195                 200                 205

Ala Glu Gln Pro Leu Leu Gly Arg Leu Ile Pro Trp Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
    290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Gly Ser Gly Ala
        355                 360                 365

Ala Asn Thr Ser Thr Gly Gly Gly Thr Leu Ser Thr Ser Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Asp Val Leu Cys Tyr Ser Thr
            420                 425                 430

Glu Val Leu Thr Asp Pro Val Glu Val Thr Gly Thr Val Ser Ala Arg
        435                 440                 445

Leu Phe Val Ser Ser Ala Val Asp Thr Asp Phe Thr Ala Lys Leu
    450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
        515                 520                 525

Phe Pro Lys Tyr Asp Arg Asn Ser Asn Thr Gly Gly Val Ile Ala Arg
    530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 4
<211> LENGTH: 574
<212> TYPE: PRT
<213> ORGANISM: Artificial
<220> FEATURE:
<223> OTHER INFORMATION: Mutant CocE pol

<400> SEQUENCE: 4

```
Met Val Asp Gly Asn Tyr Ser Val Ala Ser Asn Val Met Val Pro Met
1               5                   10                  15
Arg Asp Gly Val Arg Leu Ala Val Asp Leu Tyr Arg Pro Asp Ala Asp
            20                  25                  30
Gly Pro Val Pro Val Leu Leu Val Arg Asn Pro Tyr Asp Lys Phe Asp
        35                  40                  45
Val Phe Ala Trp Ser Thr Gln Ser Thr Asn Trp Leu Glu Phe Val Arg
    50                  55                  60
Asp Gly Tyr Ala Val Val Ile Gln Asp Thr Arg Gly Leu Phe Ala Ser
65                  70                  75                  80
Glu Gly Glu Phe Val Pro His Val Asp Asp Glu Ala Asp Ala Glu Asp
                85                  90                  95
Thr Leu Ser Trp Ile Leu Glu Gln Ala Trp Cys Asp Gly Asn Val Gly
            100                 105                 110
Met Phe Gly Val Ser Tyr Leu Gly Asp Thr Gln Trp Gln Ala Ala Val
        115                 120                 125
Ser Gly Val Gly Gly Leu Lys Ala Ile Ala Pro Ser Met Ala Ser Ala
    130                 135                 140
Asp Leu Tyr Arg Ala Pro Trp Tyr Gly Pro Gly Gly Ala Leu Ser Val
145                 150                 155                 160
Glu Ala Leu Leu Gly Trp Ser Ala Leu Ile Gly Thr Gly Leu Ile Thr
                165                 170                 175
Ser Arg Ser Asp Ala Arg Pro Glu Asp Ala Ala Asp Phe Val Gln Leu
            180                 185                 190
Ala Ala Ile Leu Asn Asp Val Ala Gly Ala Ala Ser Val Thr Pro Leu
        195                 200                 205
Ala Glu Gln Pro Leu Leu Gly Arg Leu Ile Pro Trp Val Ile Asp Gln
    210                 215                 220
Val Val Asp His Pro Asp Asn Asp Glu Ser Trp Gln Ser Ile Ser Leu
225                 230                 235                 240
Phe Glu Arg Leu Gly Gly Leu Ala Thr Pro Ala Leu Ile Thr Ala Gly
                245                 250                 255
Trp Tyr Asp Gly Phe Val Gly Glu Ser Leu Arg Thr Phe Val Ala Val
            260                 265                 270
Lys Asp Asn Ala Asp Ala Arg Leu Val Val Gly Pro Trp Ser His Ser
        275                 280                 285
Asn Leu Thr Gly Arg Asn Ala Asp Arg Lys Phe Gly Ile Ala Ala Thr
    290                 295                 300
Tyr Pro Ile Gln Glu Ala Thr Thr Met His Lys Ala Phe Phe Asp Arg
305                 310                 315                 320
His Leu Arg Gly Glu Thr Asp Ala Leu Ala Gly Val Pro Lys Val Arg
                325                 330                 335
Leu Phe Val Met Gly Ile Asp Glu Trp Arg Asp Glu Thr Asp Trp Pro
            340                 345                 350
Leu Pro Asp Thr Ala Tyr Thr Pro Phe Tyr Leu Gly Ser Gly Ala
        355                 360                 365
Ala Asn Thr Ser Thr Gly Gly Thr Leu Ser Thr Ile Ser Gly
    370                 375                 380
Thr Glu Ser Ala Asp Thr Tyr Leu Tyr Asp Pro Ala Asp Pro Val Pro
385                 390                 395                 400
Ser Leu Gly Gly Thr Leu Leu Phe His Asn Gly Asp Asn Gly Pro Ala
                405                 410                 415
```

```
Asp Gln Arg Pro Ile His Asp Arg Asp Asp Val Leu Cys Tyr Ser Thr
            420                 425                 430
Glu Val Leu Thr Asp Pro Val Glu Val Thr Gly Thr Val Ser Ala Arg
            435                 440                 445
Leu Phe Val Ser Ser Ala Val Asp Thr Asp Phe Thr Ala Lys Leu
            450                 455                 460
Val Asp Val Phe Pro Asp Gly Arg Ala Ile Ala Leu Cys Asp Gly Ile
465                 470                 475                 480
Val Arg Met Arg Tyr Arg Glu Thr Leu Val Asn Pro Thr Leu Ile Glu
                485                 490                 495
Ala Gly Glu Ile Tyr Glu Val Ala Ile Asp Met Leu Ala Thr Ser Asn
                500                 505                 510
Val Phe Leu Pro Gly His Arg Ile Met Val Gln Val Ser Ser Ser Asn
            515                 520                 525
Phe Pro Lys Tyr Asp Arg Asn Ser Asn Thr Gly Gly Val Ile Ala Arg
            530                 535                 540
Glu Gln Leu Glu Glu Met Cys Thr Ala Val Asn Arg Ile His Arg Gly
545                 550                 555                 560
Pro Glu His Pro Ser His Ile Val Leu Pro Ile Ile Lys Arg
                565                 570

<210> SEQ ID NO 5
<211> LENGTH: 574
<212> TYPE: PRT
<213> ORGANISM: Artificial
<220> FEATURE:
<223> OTHER INFORMATION: Mutant CocE polypeptide

<400> SEQUENCE: 5

Met Val Asp Gly Asn Tyr Ser Val Ala Ser Asn Val Met Val Pro Met
1               5                   10                  15
Arg Asp Gly Val Arg Leu Ala Val Asp Leu Tyr Arg Pro Asp Ala Asp
                20                  25                  30
Gly Pro Val Pro Val Leu Leu Val Arg Asn Pro Tyr Asp Lys Phe Asp
            35                  40                  45
Val Phe Ala Trp Ser Thr Gln Ser Thr Asn Trp Leu Glu Phe Val Arg
50                  55                  60
Asp Gly Tyr Ala Val Val Ile Gln Asp Thr Arg Gly Leu Phe Ala Ser
65                  70                  75                  80
Glu Gly Glu Phe Val Pro His Val Asp Asp Glu Ala Asp Ala Glu Asp
                85                  90                  95
Thr Leu Ser Trp Ile Leu Glu Gln Ala Trp Cys Asp Gly Asn Val Gly
            100                 105                 110
Met Phe Gly Val Ser Tyr Leu Gly Val Thr Gln Trp Gln Ala Ala Val
            115                 120                 125
Ser Gly Val Gly Gly Leu Lys Ala Ile Ala Pro Ser Met Ala Ser Ala
130                 135                 140
Asp Leu Tyr Arg Ala Pro Trp Tyr Gly Pro Gly Gly Ala Leu Ser Val
145                 150                 155                 160
Glu Ala Leu Leu Gly Trp Ala Ala Leu Ile Gly Thr Gly Leu Ile Thr
                165                 170                 175
Ser Arg Ser Asp Ala Arg Pro Glu Asp Ala Ala Asp Phe Val Gln Leu
            180                 185                 190
Ala Ala Ile Leu Asn Asp Val Ala Gly Ala Ala Ser Val Thr Pro Leu
            195                 200                 205
Ala Glu Gln Pro Leu Leu Gly Arg Leu Ile Pro Trp Val Ile Asp Gln
```

```
            210                 215                 220
Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
                260                 265                 270

Lys Asp Asn Ala Asp Ala Arg Leu Val Val Gly Pro Trp Ser His Ser
                275                 280                 285

Asn Leu Thr Gly Arg Asn Ala Asp Arg Lys Phe Gly Ile Ala Ala Thr
290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
                340                 345                 350

Leu Pro Asp Thr Ala Tyr Thr Pro Phe Tyr Leu Gly Gly Ser Gly Ala
                355                 360                 365

Ala Asn Thr Ser Thr Gly Gly Thr Leu Ser Thr Ser Ile Ser Gly
370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
                420                 425                 430

Glu Val Leu Thr Asp Pro Val Glu Val Thr Gly Thr Val Ser Ala Arg
                435                 440                 445

Leu Phe Val Ser Ser Ala Val Asp Thr Asp Phe Thr Ala Lys Leu
                450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
                500                 505                 510

Val Phe Leu Pro Gly His Arg Ile Met Val Gln Val Ser Ser Ser Asn
                515                 520                 525

Phe Pro Lys Tyr Asp Arg Asn Ser Asn Thr Gly Gly Val Ile Ala Arg
530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570
```

<210> SEQ ID NO 6
<211> LENGTH: 574
<212> TYPE: PRT
<213> ORGANISM: Artificial
<220> FEATURE:
<223> OTHER INFORMATION: Mutant CocE polypeptide

<400> SEQUENCE: 6

```
Met Val Asp Gly Asn Tyr Ser Val Ala Ser Asn Val Met Val Pro Met
1               5                   10                  15
```

-continued

```
Arg Asp Gly Val Arg Leu Ala Val Asp Leu Tyr Arg Pro Asp Ala Asp
                20              25              30
Gly Pro Val Pro Val Leu Leu Val Arg Asn Pro Tyr Asp Lys Phe Asp
            35              40              45
Val Phe Ala Trp Ser Thr Gln Ser Thr Asn Trp Leu Glu Phe Val Arg
 50              55              60
Asp Gly Tyr Ala Val Val Ile Gln Asp Thr Arg Gly Leu Phe Ala Ser
 65              70              75              80
Glu Gly Glu Phe Val Pro His Val Asp Glu Ala Asp Ala Glu Asp
                85              90              95
Thr Leu Ser Trp Ile Leu Glu Gln Ala Trp Cys Asp Gly Asn Val Gly
                100             105             110
Met Phe Gly Val Ser Tyr Leu Gly Val Thr Glu Trp Gln Ala Ala Val
            115             120             125
Ser Gly Val Gly Gly Leu Lys Ala Ile Ala Pro Ser Met Ala Ser Ala
    130             135             140
Asp Leu Tyr Arg Ala Pro Trp Tyr Gly Pro Gly Ala Leu Ser Val
145             150             155             160
Glu Ala Leu Leu Gly Trp Ser Ala Leu Ile Gly Thr Gly Leu Ile Thr
                165             170             175
Ser Arg Ser Asp Ala Arg Pro Glu Asp Ala Ala Asp Phe Val Gln Leu
            180             185             190
Ala Ala Ile Leu Asn Asp Val Ala Gly Ala Ala Ser Val Thr Pro Leu
    195             200             205
Ala Glu Gln Pro Leu Leu Gly Arg Leu Ile Pro Trp Val Ile Asp Gln
210             215             220
Val Val Asp His Pro Asp Asn Asp Glu Ser Trp Gln Ser Ile Ser Leu
225             230             235             240
Phe Glu Arg Leu Gly Gly Leu Ala Thr Pro Ala Leu Ile Thr Ala Gly
                245             250             255
Trp Tyr Asp Gly Phe Val Gly Glu Ser Leu Arg Thr Phe Val Ala Val
            260             265             270
Lys Asp Asn Ala Asp Ala Arg Leu Val Val Gly Pro Trp Ser His Ser
    275             280             285
Asn Leu Thr Gly Arg Asn Ala Asp Arg Lys Phe Gly Ile Ala Ala Thr
    290             295             300
Tyr Pro Ile Gln Glu Ala Thr Thr Met His Lys Ala Phe Phe Asp Arg
305             310             315             320
His Leu Arg Gly Glu Thr Asp Ala Leu Ala Gly Val Pro Lys Val Arg
                325             330             335
Leu Phe Val Met Gly Ile Asp Glu Trp Arg Asp Glu Thr Asp Trp Pro
            340             345             350
Leu Pro Asp Thr Ala Tyr Thr Pro Phe Tyr Leu Gly Gly Ser Gly Ala
    355             360             365
Ala Asn Thr Ser Thr Gly Gly Thr Leu Ser Thr Ile Ser Gly
    370             375             380
Thr Glu Ser Ala Asp Thr Tyr Leu Tyr Asp Pro Ala Asp Pro Val Pro
385             390             395             400
Ser Leu Gly Gly Thr Leu Leu Phe His Asn Gly Asp Asn Gly Pro Ala
                405             410             415
Asp Gln Arg Pro Ile His Asp Arg Asp Asp Val Leu Cys Tyr Ser Thr
            420             425             430
Glu Val Leu Thr Asp Pro Val Glu Val Thr Gly Thr Val Ser Ala Arg
```

```
                435                 440                 445
Leu Phe Val Ser Ser Ala Val Asp Thr Asp Phe Thr Ala Lys Leu
450                 455                 460
Val Asp Val Phe Pro Asp Gly Arg Ala Ile Ala Leu Cys Asp Gly Ile
465                 470                 475                 480
Val Arg Met Arg Tyr Arg Glu Thr Leu Val Asn Pro Thr Leu Ile Glu
                485                 490                 495
Ala Gly Glu Ile Tyr Glu Val Ala Ile Asp Met Leu Ala Thr Ser Asn
                500                 505                 510
Val Phe Leu Pro Gly His Arg Ile Met Val Gln Val Ser Ser Ser Asn
                515                 520                 525
Phe Pro Lys Tyr Asp Arg Asn Ser Asn Thr Gly Gly Val Ile Ala Arg
                530                 535                 540
Glu Gln Leu Glu Glu Met Cys Thr Ala Val Asn Arg Ile His Arg Gly
545                 550                 555                 560
Pro Glu His Pro Ser His Ile Val Leu Pro Ile Ile Lys Arg
                565                 570
```

<210> SEQ ID NO 7
<211> LENGTH: 574
<212> TYPE: PRT
<213> ORGANISM: Artificial
<220> FEATURE:
<223> OTHER INFORMATION: Mutant CocE polypeptide

<400> SEQUENCE: 7

```
Met Val Asp Gly Asn Tyr Ser Val Ala Ser Asn Val Met Val Pro Met
1               5                   10                  15
Arg Asp Gly Val Arg Leu Ala Val Asp Leu Tyr Arg Pro Asp Ala Asp
                20                  25                  30
Gly Pro Val Pro Val Leu Leu Val Arg Asn Pro Tyr Asp Lys Phe Asp
                35                  40                  45
Val Phe Ala Trp Ser Thr Gln Ser Thr Asn Trp Leu Glu Phe Val Arg
50                  55                  60
Asp Gly Tyr Ala Val Val Ile Gln Asp Thr Arg Gly Leu Phe Ala Ser
65                  70                  75                  80
Glu Gly Glu Phe Val Pro His Val Asp Asp Glu Ala Asp Ala Glu Asp
                85                  90                  95
Thr Leu Ser Trp Ile Leu Glu Gln Ala Trp Cys Asp Gly Asn Val Gly
                100                 105                 110
Met Phe Gly Val Ser Tyr Leu Gly Val Thr Gln Trp Gln Ala Ala Val
                115                 120                 125
Ser Gly Val Gly Gly Leu Lys Ala Ile Ala Pro Ser Met Ala Ser Ala
130                 135                 140
Asp Leu Tyr Arg Ala Pro Trp Tyr Gly Pro Gly Gly Ala Leu Ser Val
145                 150                 155                 160
Glu Ala Leu Leu Gly Trp Ser Ala Leu Ile Gly Thr Gly Leu Ile Thr
                165                 170                 175
Ser Arg Ser Asp Ala Arg Pro Glu Asp Ala Ala Asp Phe Val Gln Leu
                180                 185                 190
Ala Ala Ile Leu Asn Asp Val Ala Gly Ala Ala Ser Val Thr Pro Leu
                195                 200                 205
Ala Glu Gln Pro Leu Leu Gly Arg Leu Ile Pro Trp Val Ile Asp Gln
                210                 215                 220
Ile Val Asp His Pro Asp Asn Asp Glu Ser Trp Gln Ser Ile Ser Leu
225                 230                 235                 240
```

-continued

```
Phe Glu Arg Leu Gly Gly Leu Ala Thr Pro Ala Leu Ile Thr Ala Gly
            245                 250                 255

Trp Tyr Asp Gly Phe Val Gly Glu Ser Leu Arg Thr Phe Val Ala Val
        260                 265                 270

Lys Asp Asn Ala Asp Ala Arg Leu Val Val Gly Pro Trp Ser His Ser
    275                 280                 285

Asn Leu Thr Gly Arg Asn Ala Asp Arg Lys Phe Gly Ile Ala Ala Thr
290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Gly Ser Gly Ala
        355                 360                 365

Ala Asn Thr Ser Thr Gly Gly Thr Leu Ser Thr Ser Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
        435                 440                 445

Leu Phe Val Ser Ser Ala Val Asp Thr Asp Phe Thr Ala Lys Leu
    450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
        515                 520                 525

Phe Pro Lys Tyr Asp Arg Asn Ser Asn Thr Gly Gly Val Ile Ala Arg
    530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 8
<211> LENGTH: 574
<212> TYPE: PRT
<213> ORGANISM: Artificial
<220> FEATURE:
<223> OTHER INFORMATION: Mutant CocE polypeptide

<400> SEQUENCE: 8

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30
```

-continued

```
Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
 50                  55                  60

Asp Gly Tyr Ala Val Val Ile Gln Asp Thr Arg Gly Leu Phe Ala Ser
 65                  70                  75                  80

Glu Gly Glu Phe Val Pro His Val Asp Asp Glu Ala Asp Ala Glu Asp
                     85                  90                  95

Thr Leu Ser Trp Ile Leu Glu Gln Ala Trp Cys Asp Gly Asn Val Gly
                100                 105                 110

Met Phe Gly Val Ser Tyr Leu Gly Val Thr Gln Trp Gln Ala Ala Val
                115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
                180                 185                 190

Ala Ala Ile Leu Asn Asp Val Ala Gly Ala Ala Ser Val Thr Pro Leu
                195                 200                 205

Ala Glu Gln Pro Leu Leu Gly Arg Leu Leu Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
                260                 265                 270

Lys Asp Asn Ala Asp Ala Arg Leu Val Val Gly Pro Trp Ser His Ser
                275                 280                 285

Asn Leu Thr Gly Arg Asn Ala Asp Arg Lys Phe Gly Ile Ala Ala Thr
290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
                340                 345                 350

Leu Pro Asp Thr Ala Tyr Thr Pro Phe Tyr Leu Gly Gly Ser Gly Ala
                355                 360                 365

Ala Asn Thr Ser Thr Gly Gly Thr Leu Ser Thr Ser Ile Ser Gly
370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
                420                 425                 430

Glu Val Leu Thr Asp Pro Val Glu Val Thr Gly Thr Val Ser Ala Arg
                435                 440                 445

Leu Phe Val Ser Ser Ser Ala Val Asp Thr Asp Phe Thr Ala Lys Leu
450                 455                 460
```

```
Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
            485                 490                 495

Ala Gly Glu Ile Tyr Glu Val Ala Ile Asp Met Leu Ala Thr Ser Asn
        500                 505                 510

Val Phe Leu Pro Gly His Arg Ile Met Val Gln Val Ser Ser Ser Asn
        515                 520                 525

Phe Pro Lys Tyr Asp Arg Asn Ser Asn Thr Gly Gly Val Ile Ala Arg
    530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570
```

<210> SEQ ID NO 9
<211> LENGTH: 574
<212> TYPE: PRT
<213> ORGANISM: Artificial
<220> FEATURE:
<223> OTHER INFORMATION: Mutant CocE polypeptide

<400> SEQUENCE: 9

```
Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
    130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255
```

Trp Tyr Asp Gly Phe Val Gly Glu Ser Leu Arg Thr Phe Val Ala Val
                260                 265                 270

Lys Asp Asn Ala Asp Ala Arg Leu Val Val Gly Pro Trp Ser His Ser
            275                 280                 285

Asn Leu Thr Gly Arg Asn Ala Asp Arg Lys Phe Gly Ile Ala Ala Thr
        290                 295                 300

Tyr Pro Ile Gln Glu Asp Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
        355                 360                 365

Ala Asn Thr Ser Thr Gly Gly Thr Leu Ser Thr Ser Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
        435                 440                 445

Leu Phe Val Ser Ser Ala Val Asp Thr Asp Phe Thr Ala Lys Leu
450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
        515                 520                 525

Phe Pro Lys Tyr Asp Arg Asn Ser Asn Thr Gly Gly Val Ile Ala Arg
530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 10
<211> LENGTH: 574
<212> TYPE: PRT
<213> ORGANISM: Artificial
<220> FEATURE:
<223> OTHER INFORMATION: Mutant CocE polypeptide

<400> SEQUENCE: 10

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg

```
            50                  55                  60
Asp Gly Tyr Ala Val Val Ile Gln Asp Thr Arg Gly Leu Phe Ala Ser
 65              70                  75                  80

Glu Gly Glu Phe Val Pro His Val Asp Glu Ala Asp Ala Glu Asp
                 85                  90                  95

Thr Leu Ser Trp Ile Leu Glu Gln Ala Trp Cys Asp Gly Asn Val Gly
                100                 105                 110

Met Phe Gly Val Ser Tyr Leu Gly Val Thr Gln Trp Gln Ala Ala Val
                115                 120                 125

Ser Gly Val Gly Gly Leu Lys Ala Ile Ala Pro Ser Met Ala Ser Ala
130                 135                 140

Asp Leu Tyr Arg Ser Pro Trp Tyr Gly Pro Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
                180                 185                 190

Ala Ala Ile Leu Asn Asp Val Ala Gly Ala Ala Ser Val Thr Pro Leu
                195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
                260                 265                 270

Lys Asp Asn Ala Asp Ala Arg Leu Val Val Gly Pro Trp Ser His Ser
                275                 280                 285

Asn Leu Thr Gly Arg Asn Ala Asp Arg Lys Phe Gly Ile Ala Ala Thr
                290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
                340                 345                 350

Leu Pro Asp Thr Ala Tyr Thr Pro Phe Tyr Leu Gly Gly Ser Gly Ala
                355                 360                 365

Ala Asn Thr Ser Thr Gly Gly Gly Thr Leu Ser Thr Ser Ile Ser Gly
                370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
                420                 425                 430

Glu Val Leu Thr Asp Pro Val Glu Val Thr Gly Thr Val Ser Ala Arg
                435                 440                 445

Leu Phe Val Ser Ser Ser Ala Val Asp Thr Asp Phe Thr Ala Lys Leu
                450                 455                 460

Val Asp Val Phe Pro Asp Gly Arg Ala Ile Ala Leu Cys Asp Gly Ile
465                 470                 475                 480
```

```
Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
        515                 520                 525

Phe Pro Lys Tyr Asp Arg Asn Ser Asn Thr Gly Gly Val Ile Ala Arg
    530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570
```

<210> SEQ ID NO 11
<211> LENGTH: 574
<212> TYPE: PRT
<213> ORGANISM: Artificial
<220> FEATURE:
<223> OTHER INFORMATION: Mutant CocE polypeptide

<400> SEQUENCE: 11

```
Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
    130                 135                 140

Asp Leu Tyr Arg Ala Pro Trp Tyr Gly Pro Gly Gly Ala Leu Ala Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
```

275                 280                 285
Asn Leu Thr Gly Arg Asn Ala Asp Arg Lys Phe Gly Ile Ala Ala Thr
290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
            355                 360                 365

Ala Asn Thr Ser Thr Gly Gly Thr Leu Ser Thr Ser Ile Ser Gly
370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
            435                 440                 445

Leu Phe Val Ser Ser Ala Val Asp Thr Asp Phe Thr Ala Lys Leu
450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
            515                 520                 525

Phe Pro Lys Tyr Asp Arg Asn Ser Asn Thr Gly Gly Val Ile Ala Arg
530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 12
<211> LENGTH: 574
<212> TYPE: PRT
<213> ORGANISM: Artificial
<220> FEATURE:
<223> OTHER INFORMATION: Mutant CocE polypeptide

<400> SEQUENCE: 12

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

```
Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ala Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Gly Ser Gly Ala
        355                 360                 365

Ala Asn Thr Ser Thr Gly Gly Thr Leu Ser Thr Ile Ser Gly
370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
        435                 440                 445

Leu Phe Val Ser Ser Ala Val Asp Thr Asp Phe Thr Ala Lys Leu
450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
```

-continued

```
            500                 505                 510
Val Phe Leu Pro Gly His Arg Ile Met Val Gln Val Ser Ser Asn
        515                 520                 525

Phe Pro Lys Tyr Asp Arg Asn Ser Asn Thr Gly Gly Val Ile Ala Arg
    530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 13
<211> LENGTH: 574
<212> TYPE: PRT
<213> ORGANISM: Artificial
<220> FEATURE:
<223> OTHER INFORMATION: Mutant CocE polypeptide

<400> SEQUENCE: 13

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
        35                  40                  45

Val Phe Ala Trp Ser Thr Gln Gly Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
    130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
    290                 295                 300
```

```
Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
            325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
            355                 360                 365

Ala Asn Thr Ser Thr Gly Gly Gly Thr Leu Ser Thr Ser Ile Ser Gly
            370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
            405                 410                 415

Asp Gln Arg Pro Ile His Asp Arg Asp Asp Val Leu Cys Tyr Ser Thr
            420                 425                 430

Glu Val Leu Thr Asp Pro Val Glu Val Thr Gly Thr Val Ser Ala Arg
            435                 440                 445

Leu Phe Val Ser Ser Ser Ala Val Asp Thr Asp Phe Thr Ala Lys Leu
450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
            485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
            515                 520                 525

Phe Pro Lys Tyr Asp Arg Asn Ser Asn Thr Gly Gly Val Ile Ala Arg
            530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
            565                 570

<210> SEQ ID NO 14
<211> LENGTH: 574
<212> TYPE: PRT
<213> ORGANISM: Artificial
<220> FEATURE:
<223> OTHER INFORMATION: Mutant CocE polypeptide

<400> SEQUENCE: 14

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
        50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95
```

```
Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Ala Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
    290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Gly Ser Gly Ala
        355                 360                 365

Ala Asn Thr Ser Thr Gly Gly Gly Thr Leu Ser Thr Ser Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
        435                 440                 445

Leu Phe Val Ser Ser Ser Ala Val Asp Thr Asp Phe Thr Ala Lys Leu
    450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
        515                 520                 525
```

```
Phe Pro Lys Tyr Asp Arg Asn Ser Asn Thr Gly Gly Val Ile Ala Arg
        530                 535                 540
Glu Gln Leu Glu Glu Met Cys Thr Ala Val Asn Arg Ile His Arg Gly
545                 550                 555                 560
Pro Glu His Pro Ser His Ile Val Leu Pro Ile Ile Lys Arg
                565                 570

<210> SEQ ID NO 15
<211> LENGTH: 574
<212> TYPE: PRT
<213> ORGANISM: Artificial
<220> FEATURE:
<223> OTHER INFORMATION: Mutant CocE polypeptide

<400> SEQUENCE: 15

Met Val Asp Gly Asn Tyr Ser Val Ala Ser Asn Val Met Val Pro Met
1               5                   10                  15
Arg Asp Gly Val Arg Leu Ala Val Asp Leu Tyr Arg Pro Asp Ala Asp
            20                  25                  30
Gly Pro Val Pro Val Leu Leu Val Arg Asn Pro Tyr Asp Lys Phe Asp
        35                  40                  45
Val Phe Ala Trp Ser Thr Gln Ser Thr Asn Trp Leu Glu Phe Val Arg
    50                  55                  60
Asp Gly Tyr Ala Val Val Ile Gln Asp Thr Arg Gly Leu Phe Ala Ser
65                  70                  75                  80
Glu Gly Glu Phe Val Pro His Val Asp Asp Glu Ala Asp Ala Glu Asp
                85                  90                  95
Thr Leu Ser Trp Ile Leu Glu Gln Ala Trp Cys Asp Gly Asn Val Gly
            100                 105                 110
Met Phe Gly Val Ser Tyr Leu Gly Val Ala Gln Trp Gln Ala Ala Val
        115                 120                 125
Ser Gly Val Gly Gly Leu Lys Ala Ile Ala Pro Ser Met Ala Ser Ala
    130                 135                 140
Asp Leu Tyr Arg Ala Pro Trp Tyr Gly Pro Gly Gly Ala Leu Ser Val
145                 150                 155                 160
Glu Ala Leu Leu Gly Trp Ser Ala Leu Ile Gly Thr Gly Leu Ile Thr
                165                 170                 175
Ser Arg Ser Asp Ala Arg Pro Glu Asp Ala Ala Asp Phe Val Gln Leu
            180                 185                 190
Ala Ala Ile Leu Asn Asp Val Ala Gly Ala Ala Ser Val Thr Pro Leu
        195                 200                 205
Ala Glu Gln Pro Leu Leu Gly Arg Leu Ile Pro Trp Val Ile Asp Gln
    210                 215                 220
Val Val Asp His Pro Asp Asn Asp Glu Ser Trp Gln Ser Ile Ser Leu
225                 230                 235                 240
Phe Glu Arg Leu Gly Gly Leu Ala Thr Pro Ala Leu Ile Thr Ala Gly
                245                 250                 255
Trp Tyr Asp Gly Phe Val Gly Glu Ser Leu Arg Thr Phe Val Ala Val
            260                 265                 270
Lys Asp Asn Ala Asp Ala Arg Leu Val Val Gly Pro Trp Ser His Ser
        275                 280                 285
Asn Leu Thr Gly Arg Asn Ala Asp Arg Lys Phe Gly Ile Ala Ala Thr
    290                 295                 300
Tyr Pro Ile Gln Glu Ala Thr Thr Met His Lys Ala Phe Phe Asp Arg
305                 310                 315                 320
```

His Leu Arg Gly Glu Thr Asp Ala Leu Ala Gly Val Pro Lys Val Arg
            325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
            355                 360                 365

Ala Asn Thr Ser Thr Gly Gly Thr Leu Ser Thr Ile Ser Gly
            370                 375                 380

Thr Glu Ser Ala Asp Thr Tyr Leu Tyr Asp Pro Ala Pro Val Pro
385                 390                 395                 400

Ser Leu Gly Gly Thr Leu Leu Phe His Asn Gly Asp Asn Gly Pro Ala
            405                 410                 415

Asp Gln Arg Pro Ile His Asp Arg Asp Asp Val Leu Cys Tyr Ser Thr
            420                 425                 430

Glu Val Leu Thr Asp Pro Val Glu Val Thr Gly Thr Val Ser Ala Arg
            435                 440                 445

Leu Phe Val Ser Ser Ala Val Asp Thr Asp Phe Thr Ala Lys Leu
            450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
            485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
            515                 520                 525

Phe Pro Lys Tyr Asp Arg Asn Ser Asn Thr Gly Val Ile Ala Arg
            530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
            565                 570

<210> SEQ ID NO 16
<211> LENGTH: 574
<212> TYPE: PRT
<213> ORGANISM: Artificial
<220> FEATURE:
<223> OTHER INFORMATION: Mutant CocE polypeptide

<400> SEQUENCE: 16

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
            50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
            85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val

```
            115                 120                 125
Ser Gly Val Gly Gly Leu Lys Ala Ile Ala Pro Ala Met Ala Ser Ala
130                 135                 140
Asp Leu Tyr Arg Ala Pro Trp Tyr Gly Pro Gly Gly Ala Leu Ser Val
145                 150                 155                 160
Glu Ala Leu Leu Gly Trp Ser Ala Leu Ile Gly Thr Gly Leu Ile Thr
                    165                 170                 175
Ser Arg Ser Asp Ala Arg Pro Glu Asp Ala Ala Asp Phe Val Gln Leu
                180                 185                 190
Ala Ala Ile Leu Asn Asp Val Ala Gly Ala Ala Ser Val Thr Pro Leu
            195                 200                 205
Ala Glu Gln Pro Leu Leu Gly Arg Leu Ile Pro Trp Val Ile Asp Gln
210                 215                 220
Val Val Asp His Pro Asp Asn Asp Glu Ser Trp Gln Ser Ile Ser Leu
225                 230                 235                 240
Phe Glu Arg Leu Gly Gly Leu Ala Thr Pro Ala Leu Ile Thr Ala Gly
                    245                 250                 255
Trp Tyr Asp Gly Phe Val Gly Glu Ser Leu Arg Thr Phe Val Ala Val
                260                 265                 270
Lys Asp Asn Ala Asp Ala Arg Leu Val Val Gly Pro Trp Ser His Ser
            275                 280                 285
Asn Leu Thr Gly Arg Asn Ala Asp Arg Lys Phe Gly Ile Ala Ala Thr
290                 295                 300
Tyr Pro Ile Gln Glu Ala Thr Thr Met His Lys Ala Phe Phe Asp Arg
305                 310                 315                 320
His Leu Arg Gly Glu Thr Asp Ala Leu Ala Gly Val Pro Lys Val Arg
                    325                 330                 335
Leu Phe Val Met Gly Ile Asp Glu Trp Arg Asp Glu Thr Asp Trp Pro
                340                 345                 350
Leu Pro Asp Thr Ala Tyr Thr Pro Phe Tyr Leu Gly Gly Ser Gly Ala
            355                 360                 365
Ala Asn Thr Ser Thr Gly Gly Gly Thr Leu Ser Thr Ser Ile Ser Gly
370                 375                 380
Thr Glu Ser Ala Asp Thr Tyr Leu Tyr Asp Pro Ala Asp Pro Val Pro
385                 390                 395                 400
Ser Leu Gly Gly Thr Leu Leu Phe His Asn Gly Asp Asn Gly Pro Ala
                    405                 410                 415
Asp Gln Arg Pro Ile His Asp Arg Asp Asp Val Leu Cys Tyr Ser Thr
                420                 425                 430
Glu Val Leu Thr Asp Pro Val Glu Val Thr Gly Thr Val Ser Ala Arg
            435                 440                 445
Leu Phe Val Ser Ser Ser Ala Val Asp Thr Asp Phe Thr Ala Lys Leu
450                 455                 460
Val Asp Val Phe Pro Asp Gly Arg Ala Ile Ala Leu Cys Asp Gly Ile
465                 470                 475                 480
Val Arg Met Arg Tyr Arg Glu Thr Leu Val Asn Pro Thr Leu Ile Glu
                    485                 490                 495
Ala Gly Glu Ile Tyr Glu Val Ala Ile Asp Met Leu Ala Thr Ser Asn
                500                 505                 510
Val Phe Leu Pro Gly His Arg Ile Met Val Gln Val Ser Ser Ser Asn
            515                 520                 525
Phe Pro Lys Tyr Asp Arg Asn Ser Asn Thr Gly Gly Val Ile Ala Arg
530                 535                 540
```

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 17
<211> LENGTH: 574
<212> TYPE: PRT
<213> ORGANISM: Artificial
<220> FEATURE:
<223> OTHER INFORMATION: Mutant CocE polypeptide

<400> SEQUENCE: 17

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Leu Val Gln Leu
            180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro

```
            340                 345                 350
Leu Pro Asp Thr Ala Tyr Thr Pro Phe Tyr Leu Gly Gly Ser Gly Ala
        355                 360                 365

Ala Asn Thr Ser Thr Gly Gly Gly Thr Leu Ser Thr Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
                435                 440                 445

Leu Phe Val Ser Ser Ala Val Asp Thr Asp Phe Thr Ala Lys Leu
            450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
                500                 505                 510

Val Phe Leu Pro Gly His Arg Ile Met Val Gln Val Ser Ser Ser Asn
                515                 520                 525

Phe Pro Lys Tyr Asp Arg Asn Ser Asn Thr Gly Gly Val Ile Ala Arg
            530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 18
<211> LENGTH: 574
<212> TYPE: PRT
<213> ORGANISM: Artificial
<220> FEATURE:
<223> OTHER INFORMATION: Mutant CocE polypeptide

<400> SEQUENCE: 18

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
        50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
    130                 135                 140
```

```
Asp Leu Tyr Arg Ala Pro Trp Tyr Gly Pro Gly Ala Leu Ser Val
145                 150                 155                 160

Glu Ala Leu Leu Gly Trp Ser Ala Leu Ile Gly Thr Gly Leu Ile Thr
            165                 170                 175

Ser Arg Ser Asp Ala Arg Pro Glu Asp Ala Ala Asp Phe Val Gln Leu
            180                 185                 190

Asp Ala Ile Leu Asn Asp Val Ala Gly Ala Ala Ser Val Thr Pro Leu
            195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
                260                 265                 270

Lys Asp Asn Ala Asp Ala Arg Leu Val Val Gly Pro Trp Ser His Ser
            275                 280                 285

Asn Leu Thr Gly Arg Asn Ala Asp Arg Lys Phe Gly Ile Ala Ala Thr
            290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
                340                 345                 350

Leu Pro Asp Thr Ala Tyr Thr Pro Phe Tyr Leu Gly Ser Gly Ala
            355                 360                 365

Ala Asn Thr Ser Thr Gly Gly Gly Thr Leu Ser Thr Ser Ile Ser Gly
            370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
            435                 440                 445

Leu Phe Val Ser Ser Ser Ala Val Asp Thr Asp Phe Thr Ala Lys Leu
450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
            515                 520                 525

Phe Pro Lys Tyr Asp Arg Asn Ser Asn Thr Gly Gly Val Ile Ala Arg
            530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
```

-continued

```
                565                 570

<210> SEQ ID NO 19
<211> LENGTH: 574
<212> TYPE: PRT
<213> ORGANISM: Artificial
<220> FEATURE:
<223> OTHER INFORMATION: Mutant CocE polypeptide

<400> SEQUENCE: 19

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
    130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Arg Ala Gly
                245                 250                 255

Trp Tyr Asp Gly Phe Val Gly Gln Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
    290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Gly Ser Gly Ala
        355                 360                 365
```

```
Ala Asn Thr Ser Thr Gly Gly Gly Thr Leu Ser Thr Ser Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
            435                 440                 445

Leu Phe Val Ser Ser Ala Val Asp Thr Asp Phe Thr Ala Lys Leu
    450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
                500                 505                 510

Val Phe Leu Pro Gly His Arg Ile Met Val Gln Val Ser Ser Asn
    515                 520                 525

Phe Pro Lys Tyr Asp Arg Asn Ser Asn Thr Gly Val Ile Ala Arg
530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 20
<211> LENGTH: 574
<212> TYPE: PRT
<213> ORGANISM: Artificial
<220> FEATURE:
<223> OTHER INFORMATION: Mutant CocE polypeptide

<400> SEQUENCE: 20

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Val Pro Tyr Asp Lys Phe Asp
            35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
    130                 135                 140

Asp Leu Tyr Arg Ala Pro Trp Tyr Gly Pro Gly Gly Ala Leu Ser Val
145                 150                 155                 160
```

-continued

```
Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
    290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Gly Ser Gly Ala
        355                 360                 365

Ala Asn Thr Ser Thr Gly Gly Gly Thr Leu Ser Thr Ser Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
        435                 440                 445

Leu Phe Val Ser Ser Ala Val Asp Thr Asp Phe Thr Ala Lys Leu
    450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Asn
        515                 520                 525

Phe Pro Lys Tyr Asp Arg Asn Ser Asn Thr Gly Gly Val Ile Ala Arg
    530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 21
```

<211> LENGTH: 574
<212> TYPE: PRT
<213> ORGANISM: Artificial
<220> FEATURE:
<223> OTHER INFORMATION: Mutant CocE polypeptide

<400> SEQUENCE: 21

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Leu Gly Asp Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
        355                 360                 365

Ala Asn Thr Ser Thr Gly Gly Gly Thr Leu Ser Thr Ser Ile Ser Gly
370                 375                 380

```
Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
            405                 410                 415

Asp Gln Arg Pro Ile His Asp Arg Asp Val Leu Cys Tyr Ser Thr
        420                 425                 430

Glu Val Leu Thr Asp Pro Val Glu Val Thr Gly Thr Val Ser Ala Arg
            435                 440                 445

Leu Phe Val Ser Ser Ala Val Asp Thr Asp Phe Thr Ala Lys Leu
    450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
            485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Asn
    515                 520                 525

Phe Pro Lys Tyr Asp Arg Asn Ser Asn Thr Gly Val Ile Ala Arg
    530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
            565                 570

<210> SEQ ID NO 22
<211> LENGTH: 574
<212> TYPE: PRT
<213> ORGANISM: Artificial
<220> FEATURE:
<223> OTHER INFORMATION: Mutant CocE polypeptide

<400> SEQUENCE: 22

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
    130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
```

```
                180             185             190
Ala Ala Ile Leu Asn Asp Val Ala Gly Ala Ser Val Thr Pro Leu
            195                 200                 205
Ala Glu Gln Pro Leu Leu Gly Arg Leu Ile Pro Trp Val Ile Asp Gln
    210                 215                 220
Val Val Asp His Pro Asp Asn Asp Glu Ser Trp Gln Ser Ile Ser Leu
225                 230                 235                 240
Phe Glu Arg Leu Gly Gly Leu Ala Thr Pro Ala Leu Ile Thr Ala Gly
                245                 250                 255
Trp Tyr Asp Gly Phe Val Gly Glu Ser Leu Arg Thr Phe Val Ala Val
                260                 265                 270
Lys Asp Asn Ala Asp Ala Arg Leu Val Val Gly Pro Trp Ser His Ser
            275                 280                 285
Asn Leu Thr Gly Arg Asn Ala Asp Arg Lys Phe Gly Ile Ala Ala Thr
            290                 295                 300
Tyr Pro Ile Gln Glu Ala Thr Thr Met His Lys Ala Phe Phe Asp Arg
305                 310                 315                 320
His Leu Arg Gly Glu Thr Asp Ala Leu Ala Gly Val Pro Lys Val Arg
                325                 330                 335
Leu Phe Val Met Gly Ile Asp Glu Trp Arg Asp Glu Thr Asp Trp Pro
                340                 345                 350
Leu Pro Asp Thr Ala Tyr Thr Pro Phe Tyr Leu Gly Gly Ser Gly Ala
            355                 360                 365
Ala Asn Thr Ser Thr Gly Gly Gly Thr Leu Ser Thr Ser Ile Ser Gly
            370                 375                 380
Thr Glu Ser Ala Asp Thr Tyr Leu Tyr Asp Pro Ala Asp Pro Val Pro
385                 390                 395                 400
Ser Leu Gly Gly Thr Leu Leu Phe His Asn Gly Asp Asn Gly Pro Ala
                405                 410                 415
Asp Gln Arg Pro Ile His Asp Arg Asp Val Leu Cys Tyr Ser Thr
                420                 425                 430
Glu Val Leu Thr Asp Pro Val Glu Val Thr Gly Thr Val Ser Ala Arg
            435                 440                 445
Leu Phe Val Ser Ser Ser Ala Val Asp Thr Asp Phe Thr Ala Lys Leu
    450                 455                 460
Val Asp Val Phe Pro Asp Gly Arg Ala Ile Ala Leu Cys Asp Gly Ile
465                 470                 475                 480
Val Arg Met Arg Tyr Arg Glu Thr Leu Val Asn Pro Thr Leu Ile Glu
                485                 490                 495
Ala Gly Glu Ile Tyr Glu Val Ala Ile Asp Met Gly Ala Thr Ser Asn
            500                 505                 510
Val Phe Leu Pro Gly His Arg Ile Met Val Gln Val Ser Ser Ser Asn
            515                 520                 525
Phe Pro Lys Tyr Asp Arg Asn Ser Asn Thr Gly Gly Val Ile Ala Arg
            530                 535                 540
Glu Gln Leu Glu Glu Met Cys Thr Ala Val Asn Arg Ile His Arg Gly
545                 550                 555                 560
Pro Glu His Pro Ser His Ile Val Leu Pro Ile Ile Lys Arg
                565                 570

<210> SEQ ID NO 23
<211> LENGTH: 574
<212> TYPE: PRT
<213> ORGANISM: Artificial
<220> FEATURE:
```

<223> OTHER INFORMATION: Mutant CocE polypeptide

<400> SEQUENCE: 23

```
Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
130                 135                 140

Asp Leu Tyr Arg Ala Pro Trp His Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
    290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
        355                 360                 365

Ala Asn Thr Ser Thr Gly Gly Thr Leu Ser Thr Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
```

```
                        405                 410                 415
Asp Gln Arg Pro Ile His Asp Arg Asp Val Leu Cys Tyr Ser Thr
                420                 425                 430

Glu Val Leu Thr Asp Pro Val Glu Val Thr Gly Thr Val Ser Ala Arg
                435                 440                 445

Leu Phe Val Ser Ser Ala Val Asp Thr Asp Phe Thr Ala Lys Leu
450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
                500                 505                 510

Val Phe Leu Pro Gly His Arg Ile Met Val Gln Val Ser Ser Asn
                515                 520                 525

Phe Pro Lys Tyr Asp Arg Asn Ser Asn Thr Gly Val Ile Ala Arg
                530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 24
<211> LENGTH: 574
<212> TYPE: PRT
<213> ORGANISM: Artificial
<220> FEATURE:
<223> OTHER INFORMATION: Mutant CocE polypeptide

<400> SEQUENCE: 24

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
                35                  40                  45

Val Phe Ala Trp Ser Thr Gln Ser Thr Asn Trp Leu Glu Phe Val Arg
50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
                100                 105                 110

Met Phe Gly Val Ser Tyr Leu Gly Val Thr Gln Trp Gln Ala Ala Val
                115                 120                 125

Ser Gly Val Gly Gly Leu Lys Ala Ile Ala Pro Ser Met Ala Ser Ala
                130                 135                 140

Asp Leu Tyr Arg Ala Pro Trp Tyr Gly Pro Gly Gly Ala Leu Ser Ala
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
                180                 185                 190

Ala Ala Ile Leu Asn Asp Val Ala Gly Ala Ala Ser Val Thr Pro Leu
                195                 200                 205
```

Ala Glu Gln Pro Leu Leu Gly Arg Leu Ile Pro Trp Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
    290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Gly Ser Gly Ala
        355                 360                 365

Ala Asn Thr Ser Thr Gly Gly Gly Thr Leu Ser Thr Ser Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
        435                 440                 445

Leu Phe Val Ser Ser Ser Ala Val Asp Thr Asp Phe Thr Ala Lys Leu
    450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
        515                 520                 525

Phe Pro Lys Tyr Asp Arg Asn Ser Asn Thr Gly Gly Val Ile Ala Arg
    530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 25
<211> LENGTH: 574
<212> TYPE: PRT
<213> ORGANISM: Artificial
<220> FEATURE:
<223> OTHER INFORMATION: Mutant CocE polypeptide

<400> SEQUENCE: 25

```
Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
                100                 105                 110

Met Phe Gly Val Ser Tyr Leu Gly Val Thr Gln Trp Gln Ala Ala Val
            115                 120                 125

Ser Gly Val Gly Gly Leu Lys Ala Ile Ala Pro Ser Met Ala Ser Ala
            130                 135                 140

Asp Leu Tyr Arg Ala Pro Trp Tyr Gly Pro Gly Ala Leu Ser Val
145                 150                 155                 160

Glu Ala Leu Leu Gly Trp Ser Ala Leu Ile Gly Arg Gly Leu Ile Thr
                165                 170                 175

Ser Arg Ser Asp Ala Arg Pro Glu Asp Ala Ala Asp Phe Val Gln Leu
                180                 185                 190

Ala Ala Ile Leu Asn Asp Val Ala Gly Ala Ala Ser Val Thr Pro Leu
            195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Gly Ser Leu Arg Thr Phe Val Ala Val
            260                 265                 270

Lys Asp Asn Ala Asp Ala Arg Leu Val Val Gly Pro Trp Ser His Ser
275                 280                 285

Asn Leu Thr Gly Arg Asn Ala Asp Arg Lys Phe Gly Ile Ala Ala Thr
        290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
            355                 360                 365

Ala Asn Thr Ser Thr Gly Gly Thr Leu Ser Thr Ser Ile Ser Gly
            370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430
```

```
Glu Val Leu Thr Asp Pro Val Glu Val Thr Gly Thr Val Ser Ala Arg
            435                 440                 445

Leu Phe Val Ser Ser Ala Val Asp Thr Asp Phe Thr Ala Lys Leu
    450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
                500                 505                 510

Val Phe Leu Pro Gly His Arg Ile Met Val Gln Val Ser Ser Asn
    515                 520                 525

Phe Pro Lys Tyr Asp Arg Asn Ser Asn Thr Gly Val Ile Ala Arg
    530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 26
<211> LENGTH: 574
<212> TYPE: PRT
<213> ORGANISM: Artificial
<220> FEATURE:
<223> OTHER INFORMATION: Mutant CocE polypeptide

<400> SEQUENCE: 26

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
    210                 215                 220
```

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
            245                 250                 255

Trp Tyr Asp Gly Phe Val Gly Glu Ser Leu Arg Thr Phe Val Ala Val
        260                 265                 270

Lys Asp Asn Ala Asp Ala Arg Leu Val Val Gly Pro Trp Ser His Ser
    275                 280                 285

Asn Leu Thr Gly Arg Asn Ala Asp Arg Lys Phe Gly Ile Ala Ala Thr
290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
            325                 330                 335

Leu Phe Val Met Gly Ile Asp Glu Trp Arg Asp Glu Thr Asp Trp Pro
        340                 345                 350

Leu Pro Asp Thr Ala Tyr Thr Pro Phe Tyr Leu Gly Gly Ser Gly Ala
    355                 360                 365

Ala Asn Thr Ser Thr Gly Gly Thr Leu Ser Thr Ser Ile Ser Gly
370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
            405                 410                 415

Asp Gln Arg Pro Ile His Asp Arg Asp Val Leu Cys Tyr Ser Thr
        420                 425                 430

Glu Val Leu Thr Asp Pro Val Glu Val Thr Gly Thr Val Ser Ala Arg
    435                 440                 445

Leu Phe Val Ser Ser Ala Val Asp Thr Asp Phe Thr Ala Lys Leu
450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
            485                 490                 495

Ala Gly Glu Ile Tyr Glu Val Ala Ile Asp Met Leu Ala Thr Ser Asn
        500                 505                 510

Val Phe Leu Pro Gly His Arg Ile Met Val Gln Val Ser Ser Ser Asn
    515                 520                 525

Phe Pro Lys Phe Asp Arg Asn Ser Asn Thr Gly Gly Val Ile Ala Arg
530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
            565                 570

<210> SEQ ID NO 27
<211> LENGTH: 574
<212> TYPE: PRT
<213> ORGANISM: Artificial
<220> FEATURE:
<223> OTHER INFORMATION: Mutant CocE polypeptide

<400> SEQUENCE: 27

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp

```
                     20                  25                  30
Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
 50                  55                  60

Asp Gly Tyr Ala Val Val Ile Gln Asp Ser Arg Gly Leu Phe Ala Ser
 65                  70                  75                  80

Glu Gly Glu Phe Val Pro His Val Asp Asp Glu Ala Asp Ala Glu Asp
                    85                  90                  95

Thr Leu Ser Trp Ile Leu Glu Gln Ala Trp Cys Asp Gly Asn Val Gly
                   100                 105                 110

Met Phe Gly Val Ser Tyr Leu Gly Val Thr Gln Trp Gln Ala Ala Val
            115                 120                 125

Ser Gly Val Gly Gly Leu Lys Ala Ile Ala Pro Ser Met Ala Ser Ala
            130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
            195                 200                 205

Ala Glu Gln Pro Leu Leu Gly Arg Leu Ile Pro Trp Val Ile Asp Gln
        210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Gly Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
            355                 360                 365

Ala Asn Thr Ser Thr Gly Gly Thr Leu Ser Thr Ile Ser Gly
            370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
            435                 440                 445
```

```
Leu Phe Val Ser Ser Ala Val Asp Thr Asp Phe Thr Ala Lys Leu
    450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
                500                 505                 510

Val Phe Leu Pro Gly His Arg Ile Met Val Gln Val Ser Ser Ser Asn
            515                 520                 525

Phe Pro Lys Tyr Asp Arg Asn Ser Asn Thr Gly Val Ile Ala Arg
    530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570
```

<210> SEQ ID NO 28
<211> LENGTH: 574
<212> TYPE: PRT
<213> ORGANISM: Artificial
<220> FEATURE:
<223> OTHER INFORMATION: Mutant CocE polypeptide

<400> SEQUENCE: 28

```
Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
                100                 105                 110

Met Phe Gly Val Ser Tyr Leu Gly Val Thr Gln Trp Gln Ala Ala Val
            115                 120                 125

Ser Gly Val Gly Gly Leu Lys Ala Ile Ala Pro Ser Met Ala Ser Ala
    130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
                180                 185                 190

Ala Ala Ile Leu Asn Asp Val Ala Gly Ala Ala Ser Val Thr Pro Leu
            195                 200                 205

Ala Glu Gln Pro Leu Leu Gly Arg Leu Ile Pro Trp Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
```

```
            245                 250                 255
Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Thr Ser His Ser
            275                 280                 285

Asn Leu Thr Gly Arg Asn Ala Asp Arg Lys Phe Gly Ile Ala Ala Thr
            290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
            325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
            355                 360                 365

Ala Asn Thr Ser Thr Gly Gly Thr Leu Ser Thr Ser Ile Ser Gly
            370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
            405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
            435                 440                 445

Leu Phe Val Ser Ser Ala Val Asp Thr Asp Phe Thr Ala Lys Leu
            450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
            485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
            515                 520                 525

Phe Pro Lys Tyr Asp Arg Asn Ser Asn Thr Gly Gly Val Ile Ala Arg
            530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
            565                 570

<210> SEQ ID NO 29
<211> LENGTH: 574
<212> TYPE: PRT
<213> ORGANISM: Artificial
<220> FEATURE:
<223> OTHER INFORMATION: Mutant CocE polypeptide

<400> SEQUENCE: 29

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
            35                  40                  45
```

```
Val Phe Ala Trp Ser Thr Gln Ser Thr Asn Trp Leu Glu Phe Val Arg
     50                  55                  60

Asp Gly Tyr Ala Val Val Ile Gln Asp Thr Arg Gly Leu Phe Ala Ser
65                   70                  75                  80

Glu Gly Glu Phe Val Pro His Val Asp Asp Glu Ala Asp Ala Glu Asp
                 85                  90                  95

Thr Leu Ser Trp Ile Leu Glu Gln Ala Trp Cys Asp Gly Asn Val Gly
                100                 105                 110

Met Phe Gly Val Ser Tyr Leu Gly Val Thr Gln Trp Gln Ala Ala Val
            115                 120                 125

Ser Gly Val Gly Gly Leu Lys Ala Ile Ala Pro Ser Met Ala Ser Ala
        130                 135                 140

Asp Pro Tyr Arg Ala Pro Trp Tyr Gly Pro Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
        355                 360                 365

Ala Asn Thr Ser Thr Gly Gly Thr Leu Ser Thr Ile Ser Gly
370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
        435                 440                 445

Leu Phe Val Ser Ser Ala Val Asp Thr Asp Phe Thr Ala Lys Leu
450                 455                 460

Val Asp Val Phe Pro Asp Gly Arg Ala Ile Ala Leu Cys Asp Gly Ile
```

```
                465                 470                 475                 480
Val Arg Met Arg Tyr Arg Glu Thr Leu Val Asn Pro Thr Leu Ile Glu
                    485                 490                 495

Ala Gly Glu Ile Tyr Glu Val Ala Ile Asp Met Leu Ala Thr Ser Asn
                500                 505                 510

Val Phe Leu Pro Gly His Arg Ile Met Val Gln Val Ser Ser Ser Asn
                515                 520                 525

Phe Pro Lys Tyr Asp Arg Asn Ser Asn Thr Gly Val Ile Ala Arg
                530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 30
<211> LENGTH: 574
<212> TYPE: PRT
<213> ORGANISM: Artificial
<220> FEATURE:
<223> OTHER INFORMATION: Mutant CocE polypeptide

<400> SEQUENCE: 30

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
                35                  40                  45

Val Phe Ala Trp Ser Thr Gln Ser Thr Asn Trp Leu Glu Phe Val Arg
            50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
                100                 105                 110

Met Phe Gly Val Ser Tyr Leu Gly Val Thr Gln Trp Gln Ala Ala Val
                115                 120                 125

Ser Gly Val Gly Gly Leu Lys Ala Ile Ala Pro Ser Met Ala Ser Ala
            130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
                180                 185                 190

Ala Ala Ile Leu Asn Asp Val Ala Gly Ala Ala Ser Val Thr Pro Leu
                195                 200                 205

Ala Glu Gln Pro Leu Leu Gly Arg Leu Ile Pro Trp Val Ile Asp Gln
            210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
                260                 265                 270
```

```
Lys Asp Asn Ala Asp Ala Arg Leu Val Val Gly Pro Trp Ser His Ser
            275                 280                 285

Asn Leu Thr Gly Arg Asn Ala Asp Arg Lys Phe Gly Ile Ala Ala Thr
        290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
        355                 360                 365

Ala Asn Thr Ser Thr Gly Gly Thr Leu Ser Thr Ile Ser Gly
        370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
            435                 440                 445

Leu Phe Val Ser Ser Ala Val Asp Thr Asp Phe Thr Ala Lys Leu
        450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
            515                 520                 525

Phe Pro Lys Tyr Ser Arg Asn Ser Asn Thr Gly Gly Val Ile Ala Arg
        530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 31
<211> LENGTH: 574
<212> TYPE: PRT
<213> ORGANISM: Artificial
<220> FEATURE:
<223> OTHER INFORMATION: Mutant CocE polypeptide

<400> SEQUENCE: 31

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
        50                  55                  60
```

-continued

```
Asp Gly Tyr Ala Val Val Ile Gln Asp Thr Arg Gly Leu Phe Ala Ser
 65                  70                  75                  80

Glu Gly Glu Phe Val Pro His Val Asp Glu Ala Asp Ala Glu Asp
                 85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
    130                 135                 140

Asp Leu Tyr Arg Ala Pro Trp Tyr Gly Pro Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Arg Ile Leu Asn Asp Val Ala Gly Ala Ser Val Thr Pro Leu
        195                 200                 205

Ala Glu Gln Pro Leu Leu Gly Arg Leu Ile Pro Trp Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Pro Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
    290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
        355                 360                 365

Ala Asn Thr Ser Thr Gly Gly Thr Leu Ser Thr Ser Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
        435                 440                 445

Leu Phe Val Ser Ser Ala Val Asp Thr Phe Thr Ala Lys Leu
    450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495
```

```
Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
            515                 520                 525

Phe Pro Lys Tyr Asp Arg Asn Ser Asn Thr Gly Val Ile Ala Arg
            530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570
```

<210> SEQ ID NO 32
<211> LENGTH: 574
<212> TYPE: PRT
<213> ORGANISM: Artificial
<220> FEATURE:
<223> OTHER INFORMATION: Mutant CocE polypeptide

<400> SEQUENCE: 32

```
Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65              70                  75                  80

Glu Gly Glu Phe Val Pro His Val Asp Asp Glu Ala Asp Ala Glu Asp
            85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
            115                 120                 125

Ser Gly Val Gly Gly Leu Lys Ala Ile Ala Pro Ser Met Ala Ser Ala
    130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gln Leu Ile Thr
            165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
    195                 200                 205

Ala Glu Gln Pro Leu Leu Gly Arg Leu Ile Pro Trp Val Ile Asp Gln
            210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
            245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
    275                 280                 285
```

-continued

```
Asn Leu Thr Gly Arg Asn Ala Asp Arg Lys Phe Gly Ile Ala Ala Thr
    290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
        355                 360                 365

Ala Asn Thr Ser Thr Gly Gly Thr Leu Ser Thr Ser Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
                435                 440                 445

Leu Phe Val Ser Ser Ala Val Asp Thr Asp Phe Thr Ala Lys Leu
    450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
        515                 520                 525

Phe Pro Lys Tyr Asp Arg Asn Ser Asn Thr Gly Gly Val Ile Ala Arg
530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 33
<211> LENGTH: 574
<212> TYPE: PRT
<213> ORGANISM: Artificial
<220> FEATURE:
<223> OTHER INFORMATION: Mutant CocE polypeptide

<400> SEQUENCE: 33

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
```

```
                       85                  90                   95
Thr Leu Ser Trp Ile Leu Glu Gln Ala Trp Cys Asp Gly Asn Val Gly
                100                 105                 110
Met Phe Gly Val Ser Tyr Leu Gly Val Thr Gln Trp Gln Ala Ala Val
                115                 120                 125
Ser Gly Val Gly Gly Leu Lys Ala Ile Ala Pro Ser Met Ala Ser Ala
                130                 135                 140
Asp Leu Tyr Arg Ala Pro Trp Tyr Gly Pro Gly Ala Leu Ser Val
145                 150                 155                 160
Glu Ala Leu Leu Gly Trp Ser Ala Leu Ile Gly Thr Gly Leu Ile Thr
                165                 170                 175
Ser Arg Ser Asp Ala Arg Pro Glu Asp Ala Ala Asp Phe Val Gln Leu
                180                 185                 190
Ala Ala Ile Leu Asn Asp Val Ala Gly Ala Ser Val Thr Pro Leu
                195                 200                 205
Ala Glu Gln Pro Leu Leu Gly Arg Leu Ile Pro Trp Val Ile Asp Gln
                210                 215                 220
Val Val Asp His Pro Asp Asn Asp Glu Ser Trp Gln Ser Ile Ser Leu
225                 230                 235                 240
Phe Glu Arg Leu Gly Gly Leu Ala Thr Pro Ala Leu Ile Thr Ala Gly
                245                 250                 255
Trp Tyr Asp Gly Phe Val Gly Glu Ser Leu Arg Thr Phe Val Ala Val
                260                 265                 270
Lys Asp Asn Ala Asp Ala Arg Leu Val Val Gly Pro Trp Ser His Ser
                275                 280                 285
Asn Leu Thr Gly Arg Asn Ala Asp Arg Lys Phe Gly Ile Ala Ala Thr
                290                 295                 300
Tyr Pro Ile Gln Glu Ala Thr Thr Met His Lys Ala Phe Phe Asp Arg
305                 310                 315                 320
His Leu Arg Gly Glu Thr Asp Ala Leu Ala Gly Val Pro Lys Val Arg
                325                 330                 335
Leu Phe Val Met Gly Ile Asp Glu Trp Arg Asp Glu Thr Asp Trp Pro
                340                 345                 350
Leu Pro Asp Thr Ala Tyr Thr Pro Phe Tyr Leu Gly Gly Ser Gly Ala
                355                 360                 365
Ala Asn Thr Ser Thr Gly Gly Gly Thr Leu Ser Thr Ser Ile Ser Gly
                370                 375                 380
Thr Glu Ser Ala Asp Thr Tyr Leu Tyr Asp Pro Ala Asp Pro Val Pro
385                 390                 395                 400
Ser Leu Gly Gly Thr Leu Leu Phe His Asn Gly Asp Asn Gly Pro Ala
                405                 410                 415
Asp Gln Arg Pro Ile His Asp Arg Asp Val Leu Cys Tyr Ser Thr
                420                 425                 430
Glu Val Leu Thr Asp Pro Val Glu Val Thr Gly Thr Val Ser Ala Arg
                435                 440                 445
Leu Phe Val Ser Ser Ala Val Asp Thr Asp Phe Thr Ala Lys Leu
                450                 455                 460
Val Asp Val Phe Pro Asp Gly Arg Ala Ile Ala Leu Thr Asp Gly Ile
465                 470                 475                 480
Val Arg Met Arg Tyr Arg Glu Thr Leu Val Asn Pro Thr Leu Ile Glu
                485                 490                 495
Ala Gly Glu Ile Tyr Glu Val Ala Ile Asp Met Leu Ala Thr Ser Asn
                500                 505                 510
```

```
Val Phe Leu Pro Gly His Arg Ile Met Val Gln Val Ser Ser Ser Asn
            515                 520                 525

Phe Pro Lys Tyr Asp Arg Asn Ser Asn Thr Gly Val Ile Ala Arg
        530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 34
<211> LENGTH: 574
<212> TYPE: PRT
<213> ORGANISM: Artificial
<220> FEATURE:
<223> OTHER INFORMATION: Mutant CocE polypeptide

<400> SEQUENCE: 34

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Glu Ala Asp Ala Glu Asp
                85                  90                  95

Thr Leu Ser Trp Ile Leu Glu Gln Ala Trp Cys Asp Gly Asn Val Gly
                100                 105                 110

Met Phe Gly Val Ser Tyr Leu Gly Val Thr Gln Trp Gln Ala Ala Val
            115                 120                 125

Ser Gly Val Gly Gly Leu Lys Ala Ile Ala Pro Ser Met Ala Ser Ala
    130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
    195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
    290                 295                 300

Tyr Pro Ile Gln Glu Ala Thr Thr Met His Lys Ala Phe Phe Asp Arg
```

```
            305                 310                 315                 320
His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Gly Ser Gly Ala
        355                 360                 365

Ala Asn Thr Ser Thr Gly Gly Thr Leu Ser Thr Ser Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
        435                 440                 445

Leu Phe Val Ser Ser Ala Val Asp Thr Asp Phe Thr Ala Lys Leu
    450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
        515                 520                 525

Phe Pro Ala Tyr Asp Arg Asn Ser Asn Thr Gly Gly Val Ile Ala Arg
    530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 35
<211> LENGTH: 574
<212> TYPE: PRT
<213> ORGANISM: Artificial
<220> FEATURE:
<223> OTHER INFORMATION: R41I

<400> SEQUENCE: 35

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Ile Asn Pro Tyr Asp Lys Phe Asp
        35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110
```

```
Met Phe Gly Val Ser Tyr Leu Gly Val Thr Gln Trp Gln Ala Val
            115                 120                 125
Ser Gly Val Gly Gly Leu Lys Ala Ile Ala Pro Ser Met Ala Ser Ala
    130                 135                 140
Asp Leu Tyr Arg Ala Pro Trp Tyr Gly Pro Gly Ala Leu Ser Val
145                 150                 155                 160
Glu Ala Leu Leu Gly Trp Ser Ala Leu Ile Gly Thr Gly Leu Ile Thr
                165                 170                 175
Ser Arg Ser Asp Ala Arg Pro Glu Asp Ala Ala Asp Phe Val Gln Leu
                180                 185                 190
Ala Ala Ile Leu Asn Asp Val Ala Gly Ala Ser Val Thr Pro Leu
        195                 200                 205
Ala Glu Gln Pro Leu Leu Gly Arg Leu Ile Pro Trp Val Ile Asp Gln
    210                 215                 220
Val Val Asp His Pro Asp Asn Asp Glu Ser Trp Gln Ser Ile Ser Leu
225                 230                 235                 240
Phe Glu Arg Leu Gly Gly Leu Ala Thr Pro Ala Leu Ile Thr Ala Gly
                245                 250                 255
Trp Tyr Asp Gly Phe Val Gly Glu Ser Leu Arg Thr Phe Val Ala Val
                260                 265                 270
Lys Asp Asn Ala Asp Ala Arg Leu Val Val Gly Pro Trp Ser His Ser
            275                 280                 285
Asn Leu Thr Gly Arg Asn Ala Asp Arg Lys Phe Gly Ile Ala Ala Thr
        290                 295                 300
Tyr Pro Ile Gln Glu Ala Thr Thr Met His Lys Ala Phe Phe Asp Arg
305                 310                 315                 320
His Leu Arg Gly Glu Thr Asp Ala Leu Ala Gly Val Pro Lys Val Arg
                325                 330                 335
Leu Phe Val Met Gly Ile Asp Glu Trp Arg Asp Glu Thr Asp Trp Pro
            340                 345                 350
Leu Pro Asp Thr Ala Tyr Thr Pro Phe Tyr Leu Gly Ser Gly Ala
        355                 360                 365
Ala Asn Thr Ser Thr Gly Gly Gly Thr Leu Ser Thr Ser Ile Ser Gly
    370                 375                 380
Thr Glu Ser Ala Asp Thr Tyr Leu Tyr Asp Pro Ala Asp Pro Val Pro
385                 390                 395                 400
Ser Leu Gly Gly Thr Leu Leu Phe His Asn Gly Asp Asn Gly Pro Ala
                405                 410                 415
Asp Gln Arg Pro Ile His Asp Arg Asp Asp Val Leu Cys Tyr Ser Thr
                420                 425                 430
Glu Val Leu Thr Asp Pro Val Glu Val Thr Gly Thr Val Ser Ala Arg
            435                 440                 445
Leu Phe Val Ser Ser Ser Ala Val Asp Thr Asp Phe Thr Ala Lys Leu
        450                 455                 460
Val Asp Val Phe Pro Asp Gly Arg Ala Ile Ala Leu Cys Asp Gly Ile
465                 470                 475                 480
Val Arg Met Arg Tyr Arg Glu Thr Leu Val Asn Pro Thr Leu Ile Glu
                485                 490                 495
Ala Gly Glu Ile Tyr Glu Val Ala Ile Asp Met Leu Ala Thr Ser Asn
                500                 505                 510
Val Phe Leu Pro Gly His Arg Ile Met Val Gln Val Ser Ser Ser Asn
        515                 520                 525
Phe Pro Lys Tyr Asp Arg Asn Ser Asn Thr Gly Gly Val Ile Ala Arg
```

```
                530                 535                 540
Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 36
<211> LENGTH: 574
<212> TYPE: PRT
<213> ORGANISM: Artificial
<220> FEATURE:
<223> OTHER INFORMATION: Mutant CocE polypeptide

<400> SEQUENCE: 36

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Ala Gly Val Thr Gln Trp Gln Ala Ala Val
        115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335
```

-continued

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
        355                 360                 365

Ala Asn Thr Ser Thr Gly Gly Thr Leu Ser Thr Ser Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
        420                 425                 430

Glu Val Leu Thr Asp Pro Val Glu Val Thr Gly Thr Val Ser Ala Arg
                435                 440                 445

Leu Phe Val Ser Ser Ala Val Asp Thr Asp Phe Thr Ala Lys Leu
        450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
        515                 520                 525

Phe Pro Lys Tyr Asp Arg Asn Ser Asn Thr Gly Gly Val Ile Ala Arg
530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 37
<211> LENGTH: 574
<212> TYPE: PRT
<213> ORGANISM: Artificial
<220> FEATURE:
<223> OTHER INFORMATION: Mutant CocE polypeptide

<400> SEQUENCE: 37

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Ala Phe Asp
        35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

-continued

```
Ser Gly Val Gly Gly Leu Lys Ala Ile Ala Pro Ser Met Ala Ser Ala
    130                 135                 140

Asp Leu Tyr Arg Ala Pro Trp Tyr Gly Pro Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
                180                 185                 190

Ala Ala Ile Leu Asn Asp Val Ala Gly Ala Ala Ser Val Thr Pro Leu
            195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
                260                 265                 270

Lys Asp Asn Ala Asp Ala Arg Leu Val Val Gly Pro Trp Ser His Ser
            275                 280                 285

Asn Leu Thr Gly Arg Asn Ala Asp Arg Lys Phe Gly Ile Ala Ala Thr
290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
                340                 345                 350

Leu Pro Asp Thr Ala Tyr Thr Pro Phe Tyr Leu Gly Gly Ser Gly Ala
            355                 360                 365

Ala Asn Thr Ser Thr Gly Gly Thr Leu Ser Thr Ser Ile Ser Gly
370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
            420                 425                 430

Glu Val Leu Thr Asp Pro Val Glu Val Thr Gly Thr Val Ser Ala Arg
                435                 440                 445

Leu Phe Val Ser Ser Ser Ala Val Asp Thr Asp Phe Thr Ala Lys Leu
450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
            515                 520                 525

Phe Pro Lys Tyr Asp Arg Asn Ser Asn Thr Gly Gly Val Ile Ala Arg
530                 535                 540

Glu Gln Leu Glu Glu Met Cys Thr Ala Val Asn Arg Ile His Arg Gly
545                 550                 555                 560
```

```
Pro Glu His Pro Ser His Ile Val Leu Pro Ile Ile Lys Arg
            565                 570

<210> SEQ ID NO 38
<211> LENGTH: 574
<212> TYPE: PRT
<213> ORGANISM: Artificial
<220> FEATURE:
<223> OTHER INFORMATION: Mutant CocE polypeptide

<400> SEQUENCE: 38

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Tyr Val Pro His Val Asp Glu Ala Asp Ala Glu Asp
                85                  90                  95

Thr Leu Ser Trp Ile Leu Glu Gln Ala Trp Cys Asp Gly Asn Val Gly
                100                 105                 110

Met Phe Gly Val Ser Tyr Leu Gly Val Thr Gln Trp Gln Ala Ala Val
            115                 120                 125

Ser Gly Val Gly Gly Leu Lys Ala Ile Ala Pro Ser Met Ala Ser Ala
    130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Asn Asp Val Ala Gly Ala Ala Ser Val Thr Pro Leu
    195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
    275                 280                 285

Asn Leu Thr Gly Arg Asn Ala Asp Arg Lys Phe Gly Ile Ala Ala Thr
290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350
```

```
Leu Pro Asp Thr Ala Tyr Thr Pro Phe Tyr Leu Gly Gly Ser Gly Ala
            355                 360                 365

Ala Asn Thr Ser Thr Gly Gly Thr Leu Ser Thr Ser Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Asp Val Leu Cys Tyr Ser Thr
            420                 425                 430

Glu Val Leu Thr Asp Pro Val Glu Val Thr Gly Thr Val Ser Ala Arg
                435                 440                 445

Leu Phe Val Ser Ser Ala Val Asp Thr Asp Phe Thr Ala Lys Leu
    450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
                500                 505                 510

Val Phe Leu Pro Gly His Arg Ile Met Val Gln Val Ser Ser Ser Asn
    515                 520                 525

Phe Pro Lys Tyr Asp Arg Asn Ser Asn Thr Gly Gly Val Ile Ala Arg
    530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg
                565                 570

<210> SEQ ID NO 39
<211> LENGTH: 587
<212> TYPE: PRT
<213> ORGANISM: Artificial
<220> FEATURE:
<223> OTHER INFORMATION: Mutant CocE polypeptide

<400> SEQUENCE: 39

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
            115                 120                 125

Ser Gly Val Gly Gly Leu Lys Ala Ile Ala Pro Ser Met Ala Ser Ala
    130                 135                 140

Asp Leu Tyr Arg Ala Pro Trp Tyr Gly Pro Gly Gly Ala Leu Ser Val
```

```
145                 150                 155                 160
Glu Ala Leu Leu Gly Trp Ser Ala Leu Ile Gly Arg Gln Leu Ile Thr
                165                 170                 175

Ser Arg Ser Asp Ala Arg Pro Glu Asp Ala Ala Asp Phe Val Gln Leu
                180                 185                 190

Ala Ala Ile Leu Asn Asp Val Ala Gly Ala Ser Val Thr Pro Leu
                195                 200                 205

Ala Glu Gln Pro Leu Leu Gly Arg Leu Ile Pro Trp Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
                260                 265                 270

Lys Asp Asn Ala Asp Ala Arg Leu Val Val Gly Pro Trp Ser His Ser
                275                 280                 285

Asn Leu Thr Gly Arg Asn Ala Asp Arg Lys Phe Gly Ile Ala Ala Thr
    290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
                340                 345                 350

Leu Pro Asp Thr Ala Tyr Thr Pro Phe Tyr Leu Gly Gly Ser Gly Ala
                355                 360                 365

Ala Asn Thr Ser Thr Gly Gly Gly Thr Leu Ser Thr Ser Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Asp Val Leu Cys Tyr Ser Thr
                420                 425                 430

Glu Val Leu Thr Asp Pro Val Glu Val Thr Gly Thr Val Ser Ala Arg
                435                 440                 445

Leu Phe Val Ser Ser Ala Val Asp Thr Asp Phe Thr Ala Lys Leu
    450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
                500                 505                 510

Val Phe Leu Pro Gly His Arg Ile Met Val Gln Val Ser Ser Ser Asn
                515                 520                 525

Phe Pro Lys Tyr Asp Arg Asn Ser Asn Thr Gly Gly Val Ile Ala Arg
                530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg Lys Leu
                565                 570                 575
```

```
Ala Ala Ala Leu Glu His His His His His
            580                 585

<210> SEQ ID NO 40
<211> LENGTH: 587
<212> TYPE: PRT
<213> ORGANISM: Artificial
<220> FEATURE:
<223> OTHER INFORMATION: Mutant CocE polypeptide

<400> SEQUENCE: 40

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Arg Gly Leu Ile Thr
            165                 170                 175

Ser Arg Ser Asp Ala Arg Pro Glu Asp Ala Ala Asp Phe Val Gln Leu
        180                 185                 190

Ala Ala Ile Leu Asn Asp Val Ala Gly Ala Ala Ser Val Thr Pro Leu
    195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
            245                 250                 255

Trp Tyr Asp Gly Phe Val Gly Glu Ser Leu Arg Thr Phe Val Ala Val
        260                 265                 270

Lys Asp Asn Ala Asp Ala Arg Leu Val Val Gly Pro Trp Ser His Ser
    275                 280                 285

Asn Leu Thr Gly Arg Asn Ala Asp Arg Lys Phe Gly Ile Ala Ala Thr
290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
            325                 330                 335

Leu Phe Val Met Gly Ile Asp Glu Trp Arg Asp Glu Thr Asp Trp Pro
        340                 345                 350

Leu Pro Asp Thr Ala Tyr Thr Pro Phe Tyr Leu Gly Gly Ser Gly Ala
```

-continued

```
                355                 360                 365
Ala Asn Thr Ser Thr Gly Gly Gly Thr Leu Ser Thr Ser Ile Ser Gly
        370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
                420                 425                 430

Glu Val Leu Thr Asp Pro Val Glu Val Thr Gly Thr Val Ser Ala Arg
                435                 440                 445

Leu Phe Val Ser Ser Ala Val Asp Thr Asp Phe Thr Ala Lys Leu
                450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
                500                 505                 510

Val Phe Leu Pro Gly His Arg Ile Met Val Gln Val Ser Ser Ser Asn
                515                 520                 525

Phe Pro Lys Tyr Asp Arg Asn Ser Asn Thr Gly Gly Val Ile Ala Arg
                530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg Lys Leu
                565                 570                 575

Ala Ala Ala Leu Glu His His His His His His
                580                 585

<210> SEQ ID NO 41
<211> LENGTH: 587
<212> TYPE: PRT
<213> ORGANISM: Artificial
<220> FEATURE:
<223> OTHER INFORMATION: Mutant CocE polypeptide

<400> SEQUENCE: 41

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
50              55                  60

Asp Gly Tyr Ala Val Val Ile Gln Asp Thr Arg Gly Leu Phe Ala Ser
65              70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
        100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
    130                 135                 140
```

```
Asp Leu Tyr Arg Ala Pro Trp Tyr Gly Pro Gly Ala Leu Ser Val
145                 150                 155                 160

Glu Ala Leu Leu Gly Trp Ser Ala Leu Ile Gly Arg Gly Leu Ile Thr
            165                 170                 175

Ser Arg Ser Asp Ala Arg Pro Glu Asp Ala Ala Asp Ala Val Gln Leu
        180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
    290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

Leu Pro Asp Thr Ala Tyr Thr Pro Phe Tyr Leu Gly Ser Gly Ala
        355                 360                 365

Ala Asn Thr Ser Thr Gly Gly Gly Thr Leu Ser Thr Ser Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
        420                 425                 430

Glu Val Leu Thr Asp Pro Val Glu Val Thr Gly Thr Val Ser Ala Arg
    435                 440                 445

Leu Phe Val Ser Ser Ser Ala Val Asp Thr Asp Phe Thr Ala Lys Leu
450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
        515                 520                 525

Phe Pro Lys Tyr Asp Arg Asn Ser Asn Thr Gly Val Ile Ala Arg
        530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg Lys Leu
```

-continued

Ala Ala Ala Leu Glu His His His His His His
                580             585

<210> SEQ ID NO 42
<211> LENGTH: 582
<212> TYPE: PRT
<213> ORGANISM: Artificial
<220> FEATURE:
<223> OTHER INFORMATION: Mutant CocE polypeptide

<400> SEQUENCE: 42

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Gln Leu
            180                 185                 190

Ala Ala Ile Leu Lys Asp Val Ala Gly Ala Ala Ser Val Thr Pro Leu
        195                 200                 205

Ala Glu Gln Pro Leu Leu Gly Arg Leu Ile Pro Trp Val Ile Asp Gln
    210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Arg Asn Ala Asp Arg Lys Phe Gly Ile Ala Ala Thr
    290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335

Leu Phe Val Met Gly Ile Asp Glu Trp Arg Asp Glu Thr Asp Trp Pro
            340                 345                 350

```
Leu Pro Asp Thr Ala Tyr Thr Pro Phe Tyr Leu Gly Gly Ser Gly Ala
            355                 360                 365

Ala Asn Thr Ser Thr Gly Gly Gly Thr Leu Ser Thr Ser Ile Ser Gly
        370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Asp Val Leu Cys Tyr Ser Thr
            420                 425                 430

Glu Val Leu Thr Asp Pro Val Glu Val Thr Gly Thr Val Ser Ala Arg
        435                 440                 445

Leu Phe Val Ser Ser Ala Val Asp Thr Asp Phe Thr Ala Lys Leu
    450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
            500                 505                 510

Val Phe Leu Pro Gly His Arg Ile Met Val Gln Val Ser Ser Ser Asn
        515                 520                 525

Phe Pro Lys Tyr Asp Arg Asn Ser Asn Thr Gly Gly Val Ile Ala Arg
    530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg Leu Glu
                565                 570                 575

His His His His His His
            580

<210> SEQ ID NO 43
<211> LENGTH: 582
<212> TYPE: PRT
<213> ORGANISM: Artificial
<220> FEATURE:
<223> OTHER INFORMATION: Mutant CocE polypeptide

<400> SEQUENCE: 43

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
        35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
        115                 120                 125
```

-continued

```
Ser Gly Val Gly Gly Leu Lys Ala Ile Ala Pro Ser Met Ala Ser Ala
    130                 135                 140
Asp Leu Tyr Arg Ala Pro Trp Tyr Gly Pro Gly Ala Leu Ser Val
145                 150                 155                 160
Glu Ala Leu Leu Gly Trp Ser Ala Leu Ile Gly Thr Gly Leu Ile Thr
                165                 170                 175
Ser Arg Ser Asp Ala Lys Pro Glu Asp Ala Ala Asp Phe Val Gln Leu
            180                 185                 190
Ala Ala Ile Leu Asn Asp Val Ala Gly Ala Ser Val Thr Pro Leu
        195                 200                 205
Ala Glu Gln Pro Leu Leu Gly Arg Leu Ile Pro Trp Val Ile Asp Gln
210                 215                 220
Val Val Asp His Pro Asp Asn Asp Glu Ser Trp Gln Ser Ile Ser Leu
225                 230                 235                 240
Phe Glu Arg Leu Gly Gly Leu Ala Thr Pro Ala Leu Ile Thr Ala Gly
                245                 250                 255
Trp Tyr Asp Gly Phe Val Gly Glu Ser Leu Arg Thr Phe Val Ala Val
                260                 265                 270
Lys Asp Asn Ala Asp Ala Arg Leu Val Val Gly Pro Trp Ser His Ser
            275                 280                 285
Asn Leu Thr Gly Arg Asn Ala Asp Arg Lys Phe Gly Ile Ala Ala Thr
        290                 295                 300
Tyr Pro Ile Gln Glu Ala Thr Thr Met His Lys Ala Phe Phe Asp Arg
305                 310                 315                 320
His Leu Arg Gly Glu Thr Asp Ala Leu Ala Gly Val Pro Lys Val Arg
                325                 330                 335
Leu Phe Val Met Gly Ile Asp Glu Trp Arg Asp Glu Thr Asp Trp Pro
                340                 345                 350
Leu Pro Asp Thr Ala Tyr Thr Pro Phe Tyr Leu Gly Gly Ser Gly Ala
            355                 360                 365
Ala Asn Thr Ser Thr Gly Gly Thr Leu Ser Thr Ser Ile Ser Gly
        370                 375                 380
Thr Glu Ser Ala Asp Thr Tyr Leu Tyr Asp Pro Ala Asp Pro Val Pro
385                 390                 395                 400
Ser Leu Gly Gly Thr Leu Leu Phe His Asn Gly Asp Asn Gly Pro Ala
                405                 410                 415
Asp Gln Arg Pro Ile His Asp Arg Asp Asp Val Leu Cys Tyr Ser Thr
            420                 425                 430
Glu Val Leu Thr Asp Pro Val Glu Val Thr Gly Thr Val Ser Ala Arg
        435                 440                 445
Leu Phe Val Ser Ser Ala Val Asp Thr Asp Phe Thr Ala Lys Leu
450                 455                 460
Val Asp Val Phe Pro Asp Gly Arg Ala Ile Ala Leu Cys Asp Gly Ile
465                 470                 475                 480
Val Arg Met Arg Tyr Arg Glu Thr Leu Val Asn Pro Thr Leu Ile Glu
                485                 490                 495
Ala Gly Glu Ile Tyr Glu Val Ala Ile Asp Met Leu Ala Thr Ser Asn
            500                 505                 510
Val Phe Leu Pro Gly His Arg Ile Met Val Gln Val Ser Ser Ser Asn
        515                 520                 525
Phe Pro Lys Tyr Asp Arg Asn Ser Asn Thr Gly Gly Val Ile Ala Arg
    530                 535                 540
Glu Gln Leu Glu Glu Met Cys Thr Ala Val Asn Arg Ile His Arg Gly
545                 550                 555                 560
```

```
Pro Glu His Pro Ser His Ile Val Leu Pro Ile Ile Lys Arg Leu Glu
            565                 570                 575
His His His His His His
            580

<210> SEQ ID NO 44
<211> LENGTH: 582
<212> TYPE: PRT
<213> ORGANISM: Artificial
<220> FEATURE:
<223> OTHER INFORMATION: Mutant CocE polypeptide

<400> SEQUENCE: 44

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
                115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Lys Val Gln Leu
                180                 185                 190

Ala Ala Ile Leu Asn Asp Val Ala Gly Ala Ala Ser Val Thr Pro Leu
            195                 200                 205

Ala Glu Gln Pro Leu Leu Gly Arg Leu Ile Pro Trp Val Ile Asp Gln
        210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
                260                 265                 270

Lys Asp Asn Ala Asp Ala Arg Leu Val Val Gly Pro Trp Ser His Ser
            275                 280                 285

Asn Leu Thr Gly Arg Asn Ala Asp Arg Lys Phe Gly Ile Ala Ala Thr
        290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg
                325                 330                 335
```

```
Leu Phe Val Met Gly Ile Asp Glu Trp Arg Asp Glu Thr Asp Trp Pro
                340                 345                 350

Leu Pro Asp Thr Ala Tyr Thr Pro Phe Tyr Leu Gly Ser Gly Ala
        355                 360                 365

Ala Asn Thr Ser Thr Gly Gly Gly Thr Leu Ser Thr Ser Ile Ser Gly
    370                 375                 380

Thr Glu Ser Ala Asp Thr Tyr Leu Tyr Asp Pro Ala Asp Pro Val Pro
385                 390                 395                 400

Ser Leu Gly Gly Thr Leu Leu Phe His Asn Gly Asp Asn Gly Pro Ala
                405                 410                 415

Asp Gln Arg Pro Ile His Asp Arg Asp Val Leu Cys Tyr Ser Thr
        420                 425                 430

Glu Val Leu Thr Asp Pro Val Glu Val Thr Gly Thr Val Ser Ala Arg
                435                 440                 445

Leu Phe Val Ser Ser Ala Val Asp Thr Asp Phe Thr Ala Lys Leu
        450                 455                 460

Val Asp Val Phe Pro Asp Gly Arg Ala Ile Ala Leu Cys Asp Gly Ile
465                 470                 475                 480

Val Arg Met Arg Tyr Arg Glu Thr Leu Val Asn Pro Thr Leu Ile Glu
                485                 490                 495

Ala Gly Glu Ile Tyr Glu Val Ala Ile Asp Met Leu Ala Thr Ser Asn
                500                 505                 510

Val Phe Leu Pro Gly His Arg Ile Met Val Gln Val Ser Ser Ser Asn
                515                 520                 525

Phe Pro Lys Tyr Asp Arg Asn Ser Asn Thr Gly Gly Val Ile Ala Arg
                530                 535                 540

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg Leu Glu
                565                 570                 575

His His His His His His
            580

<210> SEQ ID NO 45
<211> LENGTH: 582
<212> TYPE: PRT
<213> ORGANISM: Artificial
<220> FEATURE:
<223> OTHER INFORMATION: Mutant CocE polypeptide

<400> SEQUENCE: 45

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
                20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
        50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
```

```
            115                 120                 125
Ser Gly Val Gly Gly Leu Lys Ala Ile Ala Pro Ser Met Ala Ser Ala
130                 135                 140
Asp Leu Tyr Arg Ala Pro Trp Tyr Gly Pro Gly Gly Ala Leu Ser Val
145                 150                 155                 160
Glu Ala Leu Leu Gly Trp Ser Ala Leu Ile Gly Thr Gly Leu Ile Thr
                    165                 170                 175
Ser Arg Ser Asp Ala Arg Pro Glu Asp Ala Ala Asp Phe Lys Gln Leu
                180                 185                 190
Ala Ala Ile Leu Asn Asp Val Ala Gly Ala Ala Ser Val Thr Pro Leu
            195                 200                 205
Ala Glu Gln Pro Leu Leu Gly Arg Leu Ile Pro Trp Val Ile Asp Gln
        210                 215                 220
Val Val Asp His Pro Asp Asn Asp Glu Ser Trp Gln Ser Ile Ser Leu
225                 230                 235                 240
Phe Glu Arg Leu Gly Gly Leu Ala Thr Pro Ala Leu Ile Thr Ala Gly
                    245                 250                 255
Trp Tyr Asp Gly Phe Val Gly Glu Ser Leu Arg Thr Phe Val Ala Val
                260                 265                 270
Lys Asp Asn Ala Asp Ala Arg Leu Val Val Gly Pro Trp Ser His Ser
            275                 280                 285
Asn Leu Thr Gly Arg Asn Ala Asp Arg Lys Phe Gly Ile Ala Ala Thr
        290                 295                 300
Tyr Pro Ile Gln Glu Ala Thr Thr Met His Lys Ala Phe Phe Asp Arg
305                 310                 315                 320
His Leu Arg Gly Glu Thr Asp Ala Leu Ala Gly Val Pro Lys Val Arg
                    325                 330                 335
Leu Phe Val Met Gly Ile Asp Glu Trp Arg Asp Glu Thr Asp Trp Pro
                340                 345                 350
Leu Pro Asp Thr Ala Tyr Thr Pro Phe Tyr Leu Gly Gly Ser Gly Ala
            355                 360                 365
Ala Asn Thr Ser Thr Gly Gly Gly Thr Leu Ser Thr Ser Ile Ser Gly
        370                 375                 380
Thr Glu Ser Ala Asp Thr Tyr Leu Tyr Asp Pro Ala Asp Pro Val Pro
385                 390                 395                 400
Ser Leu Gly Gly Thr Leu Leu Phe His Asn Gly Asp Asn Gly Pro Ala
                    405                 410                 415
Asp Gln Arg Pro Ile His Asp Arg Asp Val Leu Cys Tyr Ser Thr
                420                 425                 430
Glu Val Leu Thr Asp Pro Val Glu Val Thr Gly Thr Val Ser Ala Arg
            435                 440                 445
Leu Phe Val Ser Ser Ser Ala Val Asp Thr Asp Phe Thr Ala Lys Leu
        450                 455                 460
Val Asp Val Phe Pro Asp Gly Arg Ala Ile Ala Leu Cys Asp Gly Ile
465                 470                 475                 480
Val Arg Met Arg Tyr Arg Glu Thr Leu Val Asn Pro Thr Leu Ile Glu
                    485                 490                 495
Ala Gly Glu Ile Tyr Glu Val Ala Ile Asp Met Leu Ala Thr Ser Asn
                500                 505                 510
Val Phe Leu Pro Gly His Arg Ile Met Val Gln Val Ser Ser Ser Asn
            515                 520                 525
Phe Pro Lys Tyr Asp Arg Asn Ser Asn Thr Gly Gly Val Ile Ala Arg
        530                 535                 540
```

Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg Leu Glu
            565                 570                 575

His His His His His His
            580

<210> SEQ ID NO 46
<211> LENGTH: 582
<212> TYPE: PRT
<213> ORGANISM: Artificial
<220> FEATURE:
<223> OTHER INFORMATION: Mutant CocE polypeptide

<400> SEQUENCE: 46

Met Val Asp Gly Asn Tyr Ser Val Ala Ser Asn Val Met Val Pro Met
1               5                   10                  15

Arg Asp Gly Val Arg Leu Ala Val Asp Leu Tyr Arg Pro Asp Ala Asp
            20                  25                  30

Gly Pro Val Pro Val Leu Leu Val Arg Asn Pro Tyr Asp Lys Phe Asp
            35                  40                  45

Val Phe Ala Trp Ser Thr Gln Ser Thr Asn Trp Leu Glu Phe Val Arg
    50                  55                  60

Asp Gly Tyr Ala Val Val Ile Gln Asp Thr Arg Gly Leu Phe Ala Ser
65                  70                  75                  80

Glu Gly Glu Phe Val Pro His Val Asp Asp Glu Ala Asp Ala Glu Asp
                85                  90                  95

Thr Leu Ser Trp Ile Leu Glu Gln Ala Trp Cys Asp Gly Asn Val Gly
            100                 105                 110

Met Phe Gly Val Ser Tyr Leu Gly Val Thr Gln Trp Gln Ala Ala Val
            115                 120                 125

Ser Gly Val Gly Gly Leu Lys Ala Ile Ala Pro Ser Met Ala Ser Ala
130                 135                 140

Asp Leu Tyr Arg Ala Pro Trp Tyr Gly Pro Gly Gly Ala Leu Ser Val
145                 150                 155                 160

Glu Ala Leu Leu Gly Trp Ser Ala Leu Ile Gly Thr Gly Leu Ile Thr
                165                 170                 175

Ser Arg Ser Asp Ala Arg Pro Glu Asp Ala Ala Asp Phe Val Lys Leu
            180                 185                 190

Ala Ala Ile Leu Asn Asp Val Ala Gly Ala Ala Ser Val Thr Pro Leu
        195                 200                 205

Ala Glu Gln Pro Leu Leu Gly Arg Leu Ile Pro Trp Val Ile Asp Gln
210                 215                 220

Val Val Asp His Pro Asp Asn Asp Glu Ser Trp Gln Ser Ile Ser Leu
225                 230                 235                 240

Phe Glu Arg Leu Gly Gly Leu Ala Thr Pro Ala Leu Ile Thr Ala Gly
                245                 250                 255

Trp Tyr Asp Gly Phe Val Gly Glu Ser Leu Arg Thr Phe Val Ala Val
            260                 265                 270

Lys Asp Asn Ala Asp Ala Arg Leu Val Val Gly Pro Trp Ser His Ser
        275                 280                 285

Asn Leu Thr Gly Gln Asn Ala Asp Arg Lys Phe Gly Ile Ala Ala Thr
            290                 295                 300

Tyr Pro Ile Gln Glu Ala Thr Thr Met His Lys Ala Phe Phe Asp Arg
305                 310                 315                 320

His Leu Arg Gly Glu Thr Asp Ala Leu Ala Gly Val Pro Lys Val Arg

```
                    325                 330                 335
Leu Phe Val Met Gly Ile Asp Glu Trp Arg Asp Glu Thr Asp Trp Pro
                340                 345                 350
Leu Pro Asp Thr Ala Tyr Thr Pro Phe Tyr Leu Gly Gly Ser Gly Ala
            355                 360                 365
Ala Asn Thr Ser Thr Gly Gly Thr Leu Ser Thr Ser Ile Ser Gly
        370                 375                 380
Thr Glu Ser Ala Asp Thr Tyr Leu Tyr Asp Pro Ala Asp Pro Val Pro
385                 390                 395                 400
Ser Leu Gly Gly Thr Leu Leu Phe His Asn Gly Asp Asn Gly Pro Ala
                405                 410                 415
Asp Gln Arg Pro Ile His Asp Arg Asp Val Leu Cys Tyr Ser Thr
                420                 425                 430
Glu Val Leu Thr Asp Pro Val Glu Val Thr Gly Thr Val Ser Ala Arg
                435                 440                 445
Leu Phe Val Ser Ser Ala Val Asp Thr Asp Phe Thr Ala Lys Leu
            450                 455                 460
Val Asp Val Phe Pro Asp Gly Arg Ala Ile Ala Leu Cys Asp Gly Ile
465                 470                 475                 480
Val Arg Met Arg Tyr Arg Glu Thr Leu Val Asn Pro Thr Leu Ile Glu
                485                 490                 495
Ala Gly Glu Ile Tyr Glu Val Ala Ile Asp Met Leu Ala Thr Ser Asn
                500                 505                 510
Val Phe Leu Pro Gly His Arg Ile Met Val Gln Val Ser Ser Ser Asn
                515                 520                 525
Phe Pro Lys Tyr Asp Arg Asn Ser Asn Thr Gly Gly Val Ile Ala Arg
            530                 535                 540
Glu Gln Leu Glu Glu Met Cys Thr Ala Val Asn Arg Ile His Arg Gly
545                 550                 555                 560
Pro Glu His Pro Ser His Ile Val Leu Pro Ile Ile Lys Arg Leu Glu
                565                 570                 575
His His His His His His
            580

<210> SEQ ID NO 47
<211> LENGTH: 582
<212> TYPE: PRT
<213> ORGANISM: Artificial
<220> FEATURE:
<223> OTHER INFORMATION: Mutant CocE polypeptide

<400> SEQUENCE: 47

Met Val Asp Gly Asn Tyr Ser Val Ala Ser Asn Val Met Val Pro Met
1               5                   10                  15
Arg Asp Gly Val Arg Leu Ala Val Asp Leu Tyr Arg Pro Asp Ala Asp
                20                  25                  30
Gly Pro Val Pro Val Leu Leu Val Arg Asn Pro Tyr Asp Lys Phe Asp
            35                  40                  45
Val Phe Ala Trp Ser Thr Gln Ser Thr Asn Trp Leu Glu Phe Val Arg
        50                  55                  60
Asp Gly Tyr Ala Val Val Ile Gln Asp Thr Arg Gly Leu Phe Ala Ser
65                  70                  75                  80
Glu Gly Glu Phe Val Pro His Val Asp Asp Glu Ala Asp Ala Glu Asp
                85                  90                  95
Thr Leu Ser Trp Ile Leu Glu Gln Ala Trp Cys Asp Gly Asn Val Gly
                100                 105                 110
```

```
Met Phe Gly Val Ser Tyr Leu Gly Val Thr Gln Trp Gln Ala Val
        115                 120                 125
Ser Gly Val Gly Gly Leu Lys Ala Ile Ala Pro Ser Met Ala Ser Ala
    130                 135                 140
Asp Leu Tyr Arg Ala Pro Trp Tyr Gly Pro Gly Ala Leu Ser Val
145                 150                 155                 160
Glu Ala Leu Leu Gly Trp Ser Ala Leu Ile Gly Thr Gly Leu Ile Thr
                165                 170                 175
Ser Arg Ser Asp Ala Arg Pro Glu Asp Ala Ala Asp Phe Val Gln Leu
            180                 185                 190
Ala Lys Ile Leu Asn Asp Val Ala Gly Ala Ser Val Thr Pro Leu
        195                 200                 205
Ala Glu Gln Pro Leu Leu Gly Arg Leu Ile Pro Trp Val Ile Asp Gln
    210                 215                 220
Val Val Asp His Pro Asp Asn Asp Glu Ser Trp Gln Ser Ile Ser Leu
225                 230                 235                 240
Phe Glu Arg Leu Gly Gly Leu Ala Thr Pro Ala Leu Ile Thr Ala Gly
                245                 250                 255
Trp Tyr Asp Gly Phe Val Gly Glu Ser Leu Arg Thr Phe Val Ala Val
            260                 265                 270
Lys Asp Asn Ala Asp Ala Arg Leu Val Val Gly Pro Trp Ser His Ser
        275                 280                 285
Asn Leu Thr Gly Arg Asn Ala Asp Arg Lys Phe Gly Ile Ala Ala Thr
    290                 295                 300
Tyr Pro Ile Gln Glu Ala Thr Thr Met His Lys Ala Phe Phe Asp Arg
305                 310                 315                 320
His Leu Arg Gly Glu Thr Asp Ala Leu Ala Gly Val Pro Lys Val Arg
                325                 330                 335
Leu Phe Val Met Gly Ile Asp Glu Trp Arg Asp Glu Thr Asp Trp Pro
            340                 345                 350
Leu Pro Asp Thr Ala Tyr Thr Pro Phe Tyr Leu Gly Ser Gly Ala
        355                 360                 365
Ala Asn Thr Ser Thr Gly Gly Gly Thr Leu Ser Thr Ser Ile Ser Gly
    370                 375                 380
Thr Glu Ser Ala Asp Thr Tyr Leu Tyr Asp Pro Ala Asp Pro Val Pro
385                 390                 395                 400
Ser Leu Gly Gly Thr Leu Leu Phe His Asn Gly Asp Asn Gly Pro Ala
                405                 410                 415
Asp Gln Arg Pro Ile His Asp Arg Asp Asp Val Leu Cys Tyr Ser Thr
            420                 425                 430
Glu Val Leu Thr Asp Pro Val Glu Val Thr Gly Thr Val Ser Ala Arg
        435                 440                 445
Leu Phe Val Ser Ser Ser Ala Val Asp Thr Asp Phe Thr Ala Lys Leu
    450                 455                 460
Val Asp Val Phe Pro Asp Gly Arg Ala Ile Ala Leu Cys Asp Gly Ile
465                 470                 475                 480
Val Arg Met Arg Tyr Arg Glu Thr Leu Val Asn Pro Thr Leu Ile Glu
                485                 490                 495
Ala Gly Glu Ile Tyr Glu Val Ala Ile Asp Met Leu Ala Thr Ser Asn
            500                 505                 510
Val Phe Leu Pro Gly His Arg Ile Met Val Gln Val Ser Ser Ser Asn
        515                 520                 525
Phe Pro Lys Tyr Asp Arg Asn Ser Asn Thr Gly Gly Val Ile Ala Arg
```

```
                530                 535                 540
Glu Gln Leu Glu Glu Met Cys Thr Ala Val Asn Arg Ile His Arg Gly
545                 550                 555                 560

Pro Glu His Pro Ser His Ile Val Leu Pro Ile Ile Lys Arg Leu Glu
                565                 570                 575

His His His His His His
            580
```

ANTI-COCAINE COMPOSITIONS AND TREATMENT

CROSS-REFERENCE TO RELATED APPLICATIONS

This application claims priority to U.S. provisional application No. 60/819,569, filed Jul. 10, 2006, which is hereby incorporated by reference in its entirety.

STATEMENT REGARDING FEDERALLY SPONSORED RESEARCH OR DEVELOPMENT

This invention was made with Government support under Grant No. DA021416 and Grant No. DA013683 awarded by National Institute of Health. The Government has certain rights in the invention.

INCORPORATION-BY-REFERENCE OF MATERIAL SUBMITTED ON A COMPACT DISC

The Sequence Listing, which is a part of the present disclosure, includes a computer readable form and a written sequence listing comprising nucleotide and/or amino acid sequences of the present invention. The sequence listing information recorded in computer readable form is identical to the written sequence listing. The subject matter of the Sequence Listing is incorporated herein by reference in its entirety.

FIELD OF THE INVENTION

The invention disclosed herein generally relates to anti-cocaine therapeutics.

BACKGROUND

Abuse of cocaine is an intractable social and medical problem that is resistant to remediation through pharmacotherapy. Cocaine acts to block the reuptake of monoamines, dopamine, norepinephrine, and serotin thus prolonging and magnifying the effects of these neurotransmitters in the central nervous system (Benowitz N L (1993) Pharmacol Toxicol 72, 3-12). Cocaine toxicity is marked by both convulsions and cardiac dysfunction (e.g., myocardial infarction, cardiac arrhythmias, increased blood pressure, stroke, or dissecting aneurysm, and increased myocardial oxygen demand), due to effects on neurotransmitter systems and myocardial sodium channel blockade (Bauman J L and DiDomenico R J (2002) J Cardiovasc Pharmacol Ther 7, 195-202; Wilson L D and Shelat C (2003) J Toxicol Clin Toxicol 41, 777-788; Knuepfer M M (2003) Pharmacol Ther 97, 181-222). Because of cocaine's ability to readily cross the blood brain barrier and its widespread effects on the central and peripheral nervous systems, overdose can result in sudden death (see Bauman J L and DiDomenico R J (2002) J Cardiovasc Pharmacol Ther 7, 195-202, for review).

Although the mechanism of cocaine's action is well understood, this information has not yet resulted in the development of an effective antagonist of cocaine that could be used in abuse and overdose situations. The rapid and pleiotropic effects of cocaine present a complex problem for the treatment of acute cocaine toxicity (Carroll F I, Howell L L and Kuhar M. J (1999) J Med Chem 42, 2721-2736). The two types of therapies that are available for the treatment of opioid abuse, antagonism (e.g., naltrexone) and replacement (e.g., methadone), do not have parallels in the case of cocaine, although attempts at the latter are being considered (e.g., J. Grabowski et al. (2004) Addictive Behaviors 29, 1439-1464). One approach is to prevent or reduce the cocaine from reaching sites of action by administering either endogenous esterases, cocaine specific antibodies, or a catalytic antibody.

Naturally occurring cocaine is hydrolyzed at the benzoyl ester by serum butyrylcholinesterase (BChE) to nontoxic ecgonine methyl ester and benzoic acid. In the liver, carboxylesterase hCE-2 hydrolyzes the methyl ester to yield benzoylecgonine and methanol (see e.g., FIG. 1). The elimination half-life of cocaine in the blood ranges from 0.5 to 1.5 hr (T. Inaba (1989) Canadian Journal of Physiology & Pharmacology 67, 1154-1157). There have been a few attempts to use naturally occurring BChE or genetically engineered BChE to increase cocaine breakdown (see e.g., Carmona et al. (2000) Drug Metabolism & Disposition 28, 367-371; Xie et al. (1999) Molecular Pharmacology 55, 83-91; Sun et al. (2002a) Molecular Pharmacology; Sun et al. (2002b) Pharmacology & Experimental Therapeutics 302, 710-716; Duysen et al. (2002) Journal of Pharmacology & Experimental Therapeutics 302, 751-758; Gao Y and Brimijoin S (2004) Journal of Pharmacology & Experimental Therapeutics 310, 1046-1052; Gao et al. (2005) Molecular Pharmacology 67, 204-211). Other researchers have utilized a monoclonal antibody, Mab 15A10, as a catalytic antibody to cocaine (see e.g., Landry et al, 1993; Mets et al., 1998; Baird et al., 2000; Larsen et al., 2004), while others are exploring the use of cocaine vaccines (see e.g., Kosten et al. (2002) Vaccine 20, 1196-1204).

TABLE 1

Kinetics of several cocaine hydrolyzing enzymes against (-) cocaine.

| Enzyme | Kcat (min − 1) | Km (μM) | Efficiency (kcat/Km) | Reference |
|---|---|---|---|---|
| BChE | 4.1 | 4.5 | $9.1 \times 10^6$ | Sun et al., 2002a |
| Ala328W/Y332A | 154 | 18 | $8.5 \times 10^6$ | Sun et al., 2002a |
| Mab15A10 | 2.2 | 220 | $1 \times 10^4$ | Larsen et al., 2004 |
| AME 359 | 620 | 20 | $3.1 \times 10^7$ | Gao et al., 2005 |
| CocE | 468 | 0.64 | $7.2 \times 10^8$ | Turner et al., 2002 |

A bacterium, *Rhodococcus* sp. MB 1, indigenous to the soil surrounding the coca plant, has evolved the capacity to utilize cocaine as its sole carbon and nitrogen source. The bacterium expresses a cocaine esterase (CocE) that acts similarly to BChE to hydrolyze the benzoyl ester of cocaine, yielding ecgonine methyl ester and benzoic acid (see e.g., FIG. 1) (Bresler et al. (2000) Appl Environ Microbiol 66, 904-908; Turner et at. (2002) Biochemistry 41, 12297-12307; Larsen et al. (2002) Nature Struct Biol 9, 17-21). The gene for CocE has been isolated and cloned (Bresler et al. (2000) Appl Environ Microbiol 66, 904-908), and the crystal structure of CocE has been determined (Turner et at. (2002) Biochemistry 41, 12297-12307; Larsen et al. (2002) Nature Struct Biol 9, 17-21). The structure of CocE (see e.g., FIG. 2) reveals a classic serine esterase fold in addition to two other domains that combine to form a cocaine binding pocket. Altering any of three amino acids (Asp, His, or Ser) within the catalytic triad in the active site (for review, see Dodson G and Wlodawer A (1998) Trends Biochem Sci 23, 347-352) inactivates the esterase activity against cocaine. Furthermore, mutation of residues that make contact with the benzoate moiety of cocaine (e.g., Tyr44) also disrupts cocaine hydrolysis, presumably through impairing oxyanion stabilization in the transition state (Turner et al. (2002) Biochemistry 41, 12297-12307; Larsen et al. (2002) Nature Structural Biology 9, 17-21). The purified enzyme (MW ~65 kDa) catalyzes cocaine very efficiently with Michaelis-Menten kinetics $k_{cat}$=7.2 s$^{-1}$ and Km=640 nM (Turner et al. (2002) Biochemistry 41, 12297-12307; Larsen et al. (2002) Nature Structural Biology 9, 17-21), nearly three orders of magnitude greater than endogenous esterases and, most likely, would act quickly enough to detoxify humans who have overdosed on cocaine (Landry et al. (1993) Science 259, 1899-1901; Mets et al. (1998) National Academy of Sciences of the United States of America 95, 10176-10181). Additionally, the esterase also metabolizes cocaethylene, a potent metabolite of cocaine and alcohol, almost as efficiently as it metabolizes cocaine ($k_{cat}$=9.4 s$^{-1}$ and Km=1600 nM) (Turner et al. (2002) Biochemistry 41, 12297-12307; Larsen et al. (2002) Nature Structural Biology 9, 17-21).

Thus, it would be desirable to provide a stable CocE for anti-cocaine therapeutics.

SUMMARY OF THE INVENTION

Accordingly, the present inventors have succeeded in discovering highly efficient, thermostable, and long-lasting cocaine esterase mutants that can protect against the toxic and reinforcing effects of cocaine in subjects.

One aspect of the invention provides isolated mutant cocaine esterase (CocE) polypeptides of the wild-type CocE amino acid sequence (e.g., SEQ ID NO: 1) but with at least one amino acid residue substituted. The mutant CocE polypeptides have esterase activity with increased thermostability at 37° C. as compared to wild-type CocE.

Various embodiments include mutant CocE polypeptides with at least two, three, four, five, or more substitutions of the wild-type CocE amino acid sequence. Examples of mutant CocE polypeptides within the scope of the invention include those with an amino acid sequence of SEQ ID NO: 3 (L163V); SEQ ID NO: 7 (V225I); SEQ ID NO: 8 (I218L); SEQ ID NO: 9 (A310D); SEQ ID NO: 10 (A149S); SEQ ID NO: 11 (S159A); SEQ ID NO: 12 (S265A); SEQ ID NO: 13 (S56G); SEQ ID NO: 14 (W220A); SEQ ID NO: 16 (S140A); SEQ ID NO: 17 (F189L); SEQ ID NO: 18 (A193D); SEQ ID NO: 19 (T254R); SEQ ID NO: 20 (N42V); SEQ ID NO: 21 (V262L); SEQ ID NO: 22 (L508G); SEQ ID NO: 23 (Y152H); SEQ ID NO: 24 (V160A); SEQ ID NO: 25 (T172R); SEQ ID NO: 26 (Y532F); SEQ ID NO: 27 (T74S); SEQ ID NO: 28 (W285T); SEQ ID NO: 29 (L146P); SEQ ID NO: 30 (D533S); SEQ ID NO: 31 (A194R); SEQ ID NO: 32 (G173Q); SEQ ID NO: 33 (C477T); SEQ ID NO: 34 (K531A); SEQ ID NO: 35 (R41I); SEQ ID NO: 36 (L119A); SEQ ID NO: 37 (K46A); SEQ ID NO: 38 (F84Y), T172R-G173Q (SEQ ID NO: 39); L169K (SEQ ID NO: 40); F189A (SEQ ID NO: 41), N197K (SEQ ID NO: 42), R182K (SEQ ID NO: 43), F189K (SEQ ID NO: 44), V190K (SEQ ID NO: 45), Q191K (SEQ ID NO: 46), and A194K (SEQ ID NO: 47), or a functional fragment(s) thereof. Additional exemplary mutant CocE polypeptides include, F189A/T172R, T172R/A193D, T172R/G173Q-I175-G-G-A186, T172R/G173Q-T176G-G-D185, and the like. Given the naming conventions and polypeptide sequences disclosed herein, one skilled in the art could determine the polypeptide sequences for the above-named mutant CocE polypeptides.

Another aspect of the invention provides pharmaceutical compositions that include among their components a mutant CocE polypeptide within the scope of the invention and a pharmaceutically acceptable carrier or excipient.

Another aspect of the invention provides isolated nucleic acids encoding the mutant CocE polypeptide described herein. In various embodiments, the nucleic acids include those with sequences that hybridize to the nucleic acid encoding wild-type CocE (e.g., SEQ ID NO: 2), or the complement thereto, under high stringency conditions. Such isolated nucleic acid encodes a mutant CocE polypeptide having esterase activity with increased thermostability at 37° C. as compared to wild-type CocE. Various embodiments of the isolated nucleic acid sequence have at least about 85% sequence identity with the nucleic acid sequence of wild-type CocE (e.g., SEQ ID NO: 2). For example, the isolated nucleic acid sequence has at least about 86%, 87%, 88%, 89%, 90%, 91%, 92%, 93%, 94%, 95%, 96%, 97%, 98%, and 99% sequence identity of wild-type CocE (e.g., SEQ ID NO: 2).

In various embodiments, mutant CocE polypeptides (or polypeptides encoded by nucleic acids within the scope of the invention) have increased melting temperatures as compared to wild-type CocE. In various embodiments, mutant CocE polypeptides (or polypeptides encoded by nucleic acids within the scope of the invention) increase mutant CocE polypeptide thermostability over wild-type CocE by at least about 2.0 kcal/mol. For example, the increased thermostability can be at least about 2.1 kcal/mol, at least about 2.2 kcal/mol, at least about 2.3 kcal/mol, at least about 2.4 kcal/mol, at least about 2.5 kcal/mol, at least about 2.6 kcal/mol, at least about 2.7 kcal/mol, at least about 2.8 kcal/mol, at least about 2.9 kcal/mol, at least about 3.0 kcal/mol, at least about 3.1 kcal/mol, at least about 3.2 kcal/mol, at least about 3.3 kcal/mol, at least about 3.4 kcal/mol, at least about 3.5 kcal/mol, at least about 3.6 kcal/mol, at least about 3.7 kcal/mol, at least about 3.8 kcal/mol, at least about 3.9 kcal/mol, at least about 4.0 kcal/mol, at least about 4.1 kcal/mol, at least about 4.2 kcal/mol, at least about 4.3 kcal/mol, at least about 4.4 kcal/mol, or at least about 4.5 kcal/mol.

In various embodiments, mutant CocE polypeptides (or polypeptides encoded by nucleic acids within the scope of the invention) have reduced immunogenicity as compared to wild-type CocE.

In some embodiments, the thermostable mutant CocE polypeptides have less esterase activity than wild-type CocE. For example, thermostable CocE mutants can have about 10%, about 20%, about 30%, about 40%, about 50%, about 60%, about 65%, about 70%, about 75%, about 80%, about 85%, about 90%, about 95%, or about 99% of the esterase activity of wild-type CocE. In other embodiments, the mutant CocE polypeptides have approximately the same, or greater, catalytic efficiency of wild-type CocE polypeptides. For example, thermostable CocE mutants can have about 100%, about 110%, about 120%, about 130%, about 140%, about 150%, or more of the esterase activity of wild-type CocE.

In various embodiments, the mutant CocE polypeptides are pegylated. In various embodiments, the mutant CocE polypeptide is encapsulated in a red blood cell. For example, a pegylated mutant CocE polypeptide(s) (or a pharmaceutical composition including a pegylated mutant CocE polypeptide(s)) can be encapsulated in a RBC.

In some embodiments, the mutant CocE polypeptides are stabilized by a substrate, product, and/or inhibitor.

Another aspect of the invention provides for methods of treating a cocaine-induced condition. In such methods, a therapeutically effective amount of a mutant CocE polypeptide(s) (or a pharmaceutical composition including a mutant CocE polypeptide(s)) within the scope of the invention is administered to a subject in need thereof. In various embodiments, the cocaine-induced condition includes cocaine overdose, cocaine toxicity, cocaine addiction, cocaine dependence, and/or some combination thereof.

Yet another aspect of the invention provides for a high throughput screening method for identification of thermostable mutant CocE polypeptides. In such screening method, a cell is stably transformed with a nucleic acid encoding a mutant CocE polypeptide candidate. The mutant CocE polypeptide is expressed in the cell. The expressed mutant CocE polypeptide is isolated or displayed. The esterase activity of the isolated mutant CocE polypeptide is measured at one or more temperatures to determine thermostability of the isolated mutant CocE polypeptides. Such temperature(s) can be from about 30° C. to about 50° C. Mutant CocE polypeptide with esterase activity at the predetermined temperature(s) are selected.

In some embodiments of the screening method, measuring esterase activty of the isolated mutant polypeptides can be accomplished by contacting the isolated mutant CocE polypeptide with (i) cocaine and a pH indicator or (ii) a thio-derivative of cocaine and a thiol indicator. Any change in the pH indicator or the thiol indicator is then detected. Such a change is correlated with the formation of benzoic acid from the hydrolysis of cocaine or cocaine derivative by the mutant CocE polypeptide.

Some embodiments of the screening method further include conducting several cycles of the screening procedure at increasing temperatures for measuring esterase activity. For example, the the first cycle can employ a temperature for measuring esterase activity of about 30° C. while a subsequent cycle can employ a temperature for measuring esterase activity of about 45° C.

In some embodiments of the screening method, expression of mutant CocE polypeptide occurs at a temperature at which wild type CocE substantially retains catalytic activity. In other embodiments of the screening method, expression of mutant CocE polypeptide occurs at a temperature at which wild-type CocE polypeptide substantially partitions into inclusion bodies. For example, the expression temperature can be at least about 35° C., at least about 36° C., at least about 37° C., at least about 38° C., at least about 39° C., or at least about 40° C.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

FIG. 18A shows lethality as a function of cocaine concentration. FIG. 18B shows minutes until death after cocaine administration as a function of cocaine concentration. For further methodology information, see Example 8.

FIG. 20A is normal RBC without treatment. FIG. 20B is osmotic rupitre-reseal RBC loaded with L-ASNase. FIG. 20C is RBC loaded with LMWP-ASNase. For further methodology information, see Example 12.

FIG. 24A depicts percentage of mice exhibiting cocaine-induced lethality as a function of time of administration of wild type CocE (0.1 mg), T172R (0.1 mg), L169K (0.1 mg), or T172R-G173Q (0.1 mg) before administration of i.p. cocaine 180 mg/kg. FIG. 24B depicts percentage of mice exhibiting cocaine-induced lethality as a function of time of administration of wild type CocE (0.3 mg), T172R (0.3 mg), L169K (0.3 mg), or T172R-G173Q (0.1 mg) before administration of i.p. cocaine 180 mg/kg. FIG. 24C depicts percentage of mice exhibiting cocaine-induced lethality as a function of time of administration of wild type CocE (1 mg), T172R (1 mg), L169K (1 mg), or T172R-G173Q (1 mg) before administration of i.p. cocaine 180 mg/kg. Each data point represents the percentage of mice (n=8 for each dosing condition) exhibiting cocaine-induced lethality.

FIG. 26A depicts the percentage occurrence of lethality as a function of cocaine dosage (mg/kg, i.p.) for Vehicle/PBS, CocE wild type (0.3. mg), and PEG-CocE wild type (0.3 mg). FIG. 26B depicts the percentage occurrence of lethality as a function of cocaine dosage (mg/kg, i.p.) for Vehicle/PBS, T172R-G173Q (0.3. mg), and PEG-T172R-G173Q (0.3. mg).

DETAILED DESCRIPTION OF THE INVENTION

Figure 1:
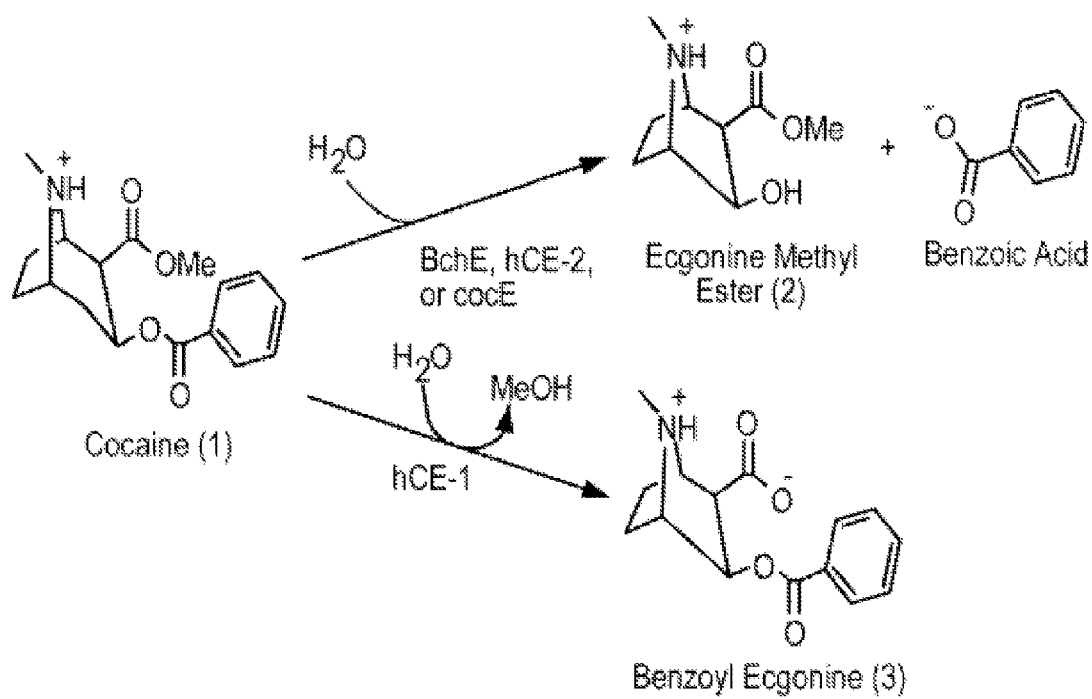
FIG. 1 is a diagram illustrating the metabolism of cocaine by various enzymatic reactions.

Embodiments of the invention disclosed wherein provide compositions and methods for a catalytic degradation approach to anti-cocaine therapeutics. The technology described herein is based in part on the discovery of highly efficient, thermostable, and long-lasting cocaine esterase mutants that can protect against the toxic and reinforcing effects of cocaine in subjects. Such mutants provide treatment options for cocaine-induced conditions such as cocaine overdose and cocaine addiction.

Mutant CocE Polypeptides

Despite the potency of wild-type CocE (see e.g., SEQ ID NO: 1, Accession No. AF173165) in metabolizing cocaine (see e.g., Example 2; Example 4; Example 5), application of wild-type CocE as a therapeutic agent in the treatment of cocaine overdose may be limited because of its low thermal stability at the physiological temperature (se e.g., Example 4; Example 6). Thermo-instability contributes to the short plasma half-life of wild-type CocE. Significant decay (>50%) of CocE activity was observed following incubation of the enzyme in plasma at 37° C., or after its intravenous administration into a mouse. The $t_{1/2}$ of CocE at 37° C. is approximately 15 minutes whereas at 4° C. the $t_{1/2}$ is greater than 6 months. Preliminary studies in rats demonstrated a relatively short duration of anti-cocaine effect of little more than 30 minutes for CocE.

One aspect of the invention thus provides purified mutant CocE polypeptides that exhibit increased thermal stability and plasma half-life as compared to wild-type CocE. The mutant CocE polypeptides of the invention hold significant clinical value because of their capability to efficiently hydrolyze cocaine, while also exhibiting increased thermostability and/or plasma half-life.

The invention provides mutant CocE polypeptides in which at least one amino acid residue of the wild-type CocE is substituted, where the mutant CocE has increased thermostability while retaining relatively high catalytic efficiency. In some embodiments, mutant CocE polypeptides substantially maintain the wild-type CocE polypeptide functional esterase activity (i.e., hydrolysis of cocaine). Mutant CocE polypeptides have a peptide sequence that differs from a native CocE polypeptide in one or more amino acids. The peptide sequence of such mutants can feature a substitution, deletion, or addition of one or more amino acids of a native CocE polypeptide. Amino acid insertions are preferably of about 1, 2, 3, and 4 to 5 contiguous amino acids, and deletions are preferably of about 1, 2, 3, 4, 5, 6, 7, 8, and 9 to 10 contiguous amino acids. In various embodiments, the mutant CocE polypeptide can contain at least one, two, three, four, or more amino acid substitutions, deletions, or additions, where the resulting mutant CocE polypeptide has increased thermostability.

The term amino acid, as used herein, is intended to include naturally occurring amino acids as well as non-naturally occurring amino acids, including amino acid analogs and derivatives. The latter includes molecules containing an amino acid moiety. One skilled in the art will recognize that reference herein to an amino acid includes, for example, naturally occurring proteogenic L-amino acids; D-amino acids; chemically modified amino acids such as amino acid analogs and derivatives; naturally occurring non-proteogenic amino acids, and chemically synthesized compounds having properties known in the art to be characteristic of amino acids. For all the amino acid sequences disclosed herein, it is understood that equivalent nucleotides and amino acids can be substituted into the sequences without affecting the function of the sequences. Such substitution is within the ability of a person of ordinary skill in the art.

The invention also provides purified mutant CocE polypeptides with the following substitutions: L163V (SEQ ID NO: 3); V121D (SEQ ID NO: 4); S167A (SEQ ID NO: 5); Q123E (SEQ ID NO: 6); V225I (SEQ ID NO: 7); I218L (SEQ ID NO: 8); A310D (SEQ ID NO: 9); A149S (SEQ ID NO: 10); S159A (SEQ ID NO: 11); S265A (SEQ ID NO: 12); S56G (SEQ ID NO: 13); W220A (SEQ ID NO: 14); T122A (SEQ ID NO: 15); S140A (SEQ ID NO: 16); F189L (SEQ ID NO: 17); A193D (SEQ ID NO: 18); T254R (SEQ ID NO: 19); N42V (SEQ ID NO: 20); V262L (SEQ ID NO: 21); L508G (SEQ ID NO: 22); Y152H (SEQ ID NO: 23); V160A (SEQ ID NO: 24); T172R (SEQ ID NO: 25); Y532F (SEQ ID NO: 26); T74S (SEQ ID NO: 27); W285T (SEQ ID NO: 28); L146P (SEQ ID NO: 29); D533S (SEQ ID NO: 30); A194R (SEQ ID NO: 31); G173Q (SEQ ID NO: 32); C477T (SEQ ID NO: 33); K531A (SEQ ID NO: 34); R411 (SEQ ID NO: 35); L119A (SEQ ID NO: 36); K46A (SEQ ID NO: 37); F84Y(SEQ ID NO: 38), T172R-G173Q (SEQ ID NO: 39); L169K (SEQ ID NO: 40); F189A (SEQ ID NO: 41), N197K (SEQ ID NO: 42), R182K (SEQ ID NO: 43), F189K (SEQ ID NO: 44), V190K (SEQ ID NO: 45), Q191K (SEQ ID NO: 46), and A194K (SEQ ID NO: 47). For example, the T172R mutant CocE polypeptide (SEQ ID NO: 25) has increased thermostability, increased Vmax and Km at 37° C., increased melting temperature (Tm), increased plasma half-life, greater reductions in lethality due to cocaine toxicity, and longer lasting anti-cocaine effects, as compared to wild-type CocE (see e.g., Example 4, Example 7).

The resulting increase in thermostability of the mutant CocE polypeptide is at least about 2 kcal/mol. Thermostability of a given polypeptide can be assessed by a variety of methods known to the art, including for example circular dichroism (CD) spectroscopy or differential scanning calorimeter. For example, the resulting increase in thermostability can be at least about 2.1, at least about 2.2, at least about 2.3, at least about 2.4, at least about 2.5, at least about 2.6, at least about 2.7, at least about 2.8, at least about 2.9, at least about 3.0, at least about 3.1, at least about 3.2, at least about 3.3, at least about 3.4, at least about 3.5, at least about 3.6, at least about 3.7, at least about 3.8, at least about 3.9, at least about 4.0, at least about 4.1, at least about 4.2, at least about 4.3, at least about 4.4, or at least about 4.5 kcal/mol. Even greater thermostability increases are contemplated. It is thought that lowering the energy by about 2.1 to about 4.5 kcal/mol can extend the half-life time of the protein about 30 to about 1000 fold longer at room temperature.

Generally, the mutant CocE polypeptides have esterase activity with increased thermostability as compared to wild-type CocE. In some embodiments, the thermostable mutant CocE polypeptides can have less esterase activity than wild-type CocE. For example, thermostable CocE mutants can have about 10%, about 20%, about 30%, about 40%, about 50%, about 60%, about 65%, about 70%, about 75%, about 80%, about 85%, about 90%, about 95%, or about 99% of the esterase activity of wild-type CocE. In other embodiments, the mutant CocE polypeptides have approximately the same, or greater, catalytic efficiency of wild-type CocE polypeptides. For example, thermostable CocE mutants can have about 100%, about 110%, about 120%, about 130%, about 140%, about 150%, or more of the esterase activity of wild-type CocE.

Variants of the mutant CocE polypeptides such as fragments, analogs, and derivatives are also within the invention. CocE polypeptide fragments corresponding to one or more particular motifs and/or domains or to arbitrary sizes, for example, at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 75, 100, 125, 150, 200, 250, 300, 400, 500, 600, 700, 800, 900, 1000, 1100, 1150 and 1200 amino acids in length are intended to be within the scope of the invention disclosed herein. Isolated peptidyl portions of CocE polypeptides can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, a CocE polypeptide as described herein can be arbitrarily divided into fragments of desired length with no overlap of the fragments, or preferably divided into overlapping fragments of a desired length.

Another aspect of the invention disclosed herein concerns recombinant forms of the CocE polypeptide. In some embodiments, isolated nucleic acid molecules of the invention include those polynucleotides encoding the above described CocE polypeptides. In other embodiments, the recombinant polypeptides of the invention disclosed herein are encoded by a nucleic acid that has at least 85% sequence identity (e.g., 85%, 86%, 87%, 88%, 89%, 90%, 91%, 92%, 93%, 94%, 95%, 96%, 97%, 98%, and 99%) with the nucleic acid sequence of SEQ ID NO: 2, where the expressed recombinant CocE polypeptide retains substantially the same or more catalytic efficiency of wild-type CocE polypeptide and has increased thermostability as compared to wild-type CocE.

Nucleic acids that hybridize under stringent conditions to the nucleic acids of SEQ ID NO: 2 or the complements of SEQ ID NO: 2 can also be used in the invention. For example, such nucleic acids that hybridize to SEQ ID NO: 2 or the complement of SEQ ID NO: 2 under low stringency conditions, moderate stringency conditions, or high stringency conditions and also encode a mutant CocE polypeptide that has esterase activity with increased thermostability as compared to wild-type CocE, are within the invention. Preferred nucleic acids are those having a nucleotide sequence that is the complement of all or a portion of SEQ ID NO: 2. Other variants of the native CocE gene within the invention are polynucleotides that share at least 65% (e.g., 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity to SEQ ID NO: 2 or the complement of SEQ ID NO: 2. Nucleic acids that hybridize under stringent conditions to or share at least 65% sequence identity with SEQ ID NO: 2 or the complement of SEQ ID NO: 2 can be obtained by techniques known in the art such as by making mutations in the native CocE gene, or by isolation from an organism expressing such a nucleic acid (e.g., an allelic variant).

Nucleic acid molecules encoding mutant CocE fusion proteins are also within the invention. Such nucleic acids can be made by preparing a construct (e.g., an expression vector) that expresses mutant CocE fusion protein when introduced into a suitable host. For example, such a construct can be made by ligating a first polynucleotide encoding mutant CocE protein fused in frame with a second polynucleotide encoding another protein such that expression of the construct in a suitable expression system yields a fusion protein.

The nucleic acid molecules of the invention can be modified at a base moiety, sugar moiety, or the phosphate backbone, e.g., to improve stability of the molecule, hybridization, and the like. Nucleic acid molecules utilized in embodiments of the invention disclosed herein can be in the form of RNA or in the form of DNA (e.g., cDNA, genomic DNA, and synthetic DNA). The DNA can be double-stranded or single-stranded, and if single-stranded can be the coding (sense) strand or non-coding (anti-sense) strand. The coding sequence which encodes a mutant CocE polypeptide can be identical to the claimed nucleotide sequence, or it can also be a different coding sequence which, as a result of the redundancy or degeneracy of the genetic code, encodes the same polypeptide as the polynucleotides of SEQ ID NOS: 3-37.

Design of Mutant CocE

CocE thermostabilizing mutations can be designed to either increase the thermodynamic stability of a polypeptide through lowering ΔG(unfolded→folded) or decrease rate of unfolding through increasing the activation free energy of the unfolding process. The ΔG(unfolded→folded) is the free-energy difference between the unfolded and the folded state. For a thermodynamically stable polypeptide, ΔG(unfolded→folded) should be a negative value. Generally, the lower the ΔG(unfolded→folded) value, the more stable the folded state. The activation free energy of the unfolding process is the free energy difference between the folded state and the transition state of unfolding (Steipe, 1999).

Mutant CocE polypeptides with increased thermostability can be designed and generated by a variety of methods known to the art including, for example, rational design, directed evolution (e.g., random mutagenesis, mutagenesis of the CocE host organism), or a combination thereof. Directed evolution can be achieved through mutation and recombination followed by either screening for the desired trait or by applying a selective pressure to obtain the trait of interest (see e.g., Lehmann and Wyss, 2001). Mutagenesis can be performed either on the specific gene of interest or through mutagenesis and selection of a host organism such that the engineered property is conferred to the protein of interest. Preferably, the thermostability of CocE mutants are engineered through a three-prong approach of (i) rational design through computation-guided site-directed mutagenesis (see e.g., Example 3; Example 4), (ii) random mutagenesis of the CocE gene and high throughput screening (see e.g., Example 4; Example 15); and (iii) mutagenesis of the CocE host organism followed by genetic selection (see e.g., Example 14).

Various rational design concepts are known to those of skill in the art to accomplish lowering ΔG(unfolded→folded) and/or increasing the activation free energy of the unfolding process (see e.g., Lehmann, 2001). For example, one can: decrease the entropy of the unfolded state by introducing additional disulfide bridges or by X→Pro mutations; increase a-helix propensity by Gly→Ala substitutions or by stabilization of a-helix macrodipoles; improve electrostatic interactions between charged surface residues by introducing additional salt bridges or even salt-bridge networks, or by thermostabilizing mutations based on calculations of electrostatic potentials.

Molecular modeling, based on appropriate molecular dynamics (MD) simulations, can rationally guide site-directed mutagenesis so as to design mutant CocE polypeptides possessed of increased thermostability. Classical MD simulation enables the study of time evolution of a large system by taking many small successive time steps under atomic forces determined by a set of parameterized interaction functions (force field), including bonded interactions (bonds, angles, and dihedral angles), non-bonded van der Waals interactions, and electrostatic interactions based or net atomic charges. Due to the simple force field form, the MD simulation may be performed for a sufficiently long simulation time to give meaningful ensemble-averaged properties, even for a very large system involving over a hundred thousand atoms. So, for CocE and each proposed mutant, the MD simulation can lead to a reasonable, dynamically averaged 3D structure of the simulated polypeptide in water.

One approach used successfully herein focuses on the rational design of thermostabilizing mutations that lower the ΔG(unfolded→folded) value of the polypeptide (see e.g., Example 3). Such approach requires only the calculation of ΔG(unfolded→folded), without performing a more time-consuming computation on the structure and energetics of the transition state of the unfolding. Hence, to increase the thermostability of a polypeptide before pegylation, one can use a method implemented in a rational design program (e.g., RosettaDesign) that uses an energy function for evaluating the fitness of a particular sequence for a given fold and a Monte Carlo search algorithm for sampling sequence space.

Such approach is known to produce increased thermostability of other enzymes with no reduction in catalytic efficiency (see e.g., Korkegian, 2005). For example, the fold used in the computation can correspond to that of the available CocE X-ray crystal structure.

The rational design program allows prediction of a set of modified amino acid sequences that potentially have lower energies (e.g., the ΔG(unfolded→folded) values) and, therefore, higher thermostability. Thus, one can use the computational design described herein to predict mutations in the CocE polypeptide core that can lead to thermostabilization of the polypeptide without loss of catalytic efficiency. This approach minimizes experimental test time and greatly increases the success of experimental outcomes. The predicted thermostabilizing mutations can be tested individually by site-directed mutagenesis and then in combination, in an iterative process (see e.g., Example 15).

Directed evolution can also be used to generate thermostable CocE mutants. Directed evolution encompasses a series of experimental techniques that produce accelerated diversity and adaptation through mutation and recombination followed by either screening for the desired trait or by applying a selective pressure to obtain the trait of interest (Lehmann & Wyss (2001) Current Opinion in Biotechnology 12, 371-375). Thus directed evolution involves both a process to generate diversity and an efficient screening or selection method for the detection or enrichment of the desired trait. Directed evolution has previously been successfully applied to the production of thermostable proteins, and the generation of diversity has been achieved through, for example, error prone PCR, saturation mutagenesis, DNA shuffling, chemical mutagenesis, and combinations thereof. Error prone PCR amplifies the gene of interest with non-proofreading polymerases and stressful conditions designed to randomly generate single base pair mutations. After each round the best mutants are selected and are used as parent sequences in the next round of mutagenesis. This technique has been used to generate a number of thermostable protein variants, including propyl endopeptidase (Uchiyama ma., et al. 2000), betaglucuronidase (Flores, H. and A. D. Ellington (2002) Journal of Molecular Biology 315, 325-337) and family 10 xylanases (Andrews et al. (2004) J Biol Chem 279, 54369-79). Saturation mutagenesis also amplifies the gene of interest but incorporates universal bases during amplification to generate a much higher number of mutations. This technique has been used to generate thermostability in a psychrophilic enzyme (Miyazaki et al. (2000) Journal of Molecular Biology 297, 1015-1026). DNA shuffling involves one or more cycles of recombination between a set of homologous sequences to obtain improved variants of a given enzyme. This technique can also be used in tandem with error-prone PCR, where the best mutants obtained by error-prone PCR are combined by DNA shuffling to generate a new subset of mutants. DNA shuffling has been implemented to generate thermostable variants of beta-glucuronidase (Flores, H. and A. D. Ellington (2002) Journal of Molecular Biology 315, 325-337). Chemical mutagenesis involves treating plasmid DNA with chemicals that introduce point mutations into the sequence such as hydroxylamine, nitrosamines or dimethyl sulfate. Plasmid treatment with hydroxylamine has been used to generate thermostable mutants of Bacillus polymyxa beta-glucosidase A (Lopez-Camacho et al. (1996) Biochemistry Journal 314, 833-838) and firefly luciferase (White et al. (1996) Biochemistry Journal 319 (Pt 2), 343-350).

Mutagenesis of the CocE host organism can also be used to generate thermostable CocE mutants. A simple and fast method for the production of thermostable CocE variants can be achieved by utilizing the enzyme's ability to confer metabolism of cocaine as a sole carbon source on its host organism. The CocE gene was originally sequenced from *Rhodococcus* MB1 by subcloning gene fragments into *Rhodococcus erythropolis* CW25, a bacterium unable to metabolize cocaine but able to grow on the cocaine esterase byproducts ecgonine methyl ester and benzoate (Bresler et al. (2000) Applied & Environmental Microbiology 66, 904-908). Another organism previously shown to metabolize cocaine byproducts is *Pseudomonas fluorescens* (MBER), which was able to grow in a symbiotic relationship with another bacterium able to metabolize cocaine via the esterase *Comamonas acidovorans* (MBLF).

While difficult to transform with plasmids at high efficiencies, these bacterial strains can be relatively easily transformed with the native CocE gene cloned into appropriate shuttle vectors and then traditional bacterial mutagenesis can be performed (see e.g., Example 14). Because these bacteria would normally only grow at 25-30° C. on cocaine hydrolysis products, selection for mutants able to metabolize cocaine efficiently at 37° C. would be expected to select for highly active and CocE mutants that are stable at 37° C.

The exposure of bacteria to radiation or chemical agents for the production of mutants carrying new phenotypes is well known in the art (see e.g., Maron, D. M. and Ames, B N (1983) Mutation Research 113, 173-215). Mutagenesis by irradiation can involve both ionizing and non-ionizing radiation; however, non-ionization radiation is the widely used, and UV radiation at 260 nm is most effective as a lethal agent. Mutagenesis is caused by the induction of pyrimidine dimers, increasing the likelihood of incorporating mismatches during replication. Cells are exposed to UV radiation at a dose predetermined to kill 90-95% of the cell population, and mutants are then sought among the survivors. Chemical mutagenesis includes the use of base analogs such as 5-bromouracil and 2-aminopurine which increase copy error during replication, or the use of agents that react directly with DNA such as hydroxylamine or nitrosoguanidine which induce mutations at a higher frequency than base analogs.

Generating Mutant CocE Polypeptides

Embodiments of the invention further pertain to methods of producing the mutant CocE polypeptides. For example, a host cell transfected with a nucleic acid vector directing expression of a nucleotide sequence encoding the mutant CocE polypeptides can be cultured under appropriate conditions to allow expression of the peptide to occur. The cells can be harvested, lysed, and the protein isolated. A mutant CocE polypeptide can be isolated from host cells using techniques known in the art for purifying proteins including ion-exchange chromatography, gel filtration chromatography, ultrafiltration, electrophoresis, and immunoaffinity purification with antibodies specific for such protein (see e.g., Example 1).

For example, after a mutant CocE polypeptide has been expressed in a cell, it can be isolated using any immunoaffinity chromatography. More specifically, an anti-CocE antibody can be immobilized on a column chromatography matrix, and the matrix can be used for immuno-affinity chromatography to purify the mutant CocE polypeptide from cell lysates by standard methods (see, e.g., Sambrook and Russel (2006) Condensed Protocols from Molecular Cloning: A Laboratory Manual, Cold Spring Harbor Laboratory Press, ISBN 0879697717). After immuno-affinity chromatography, the mutant CocE polypeptide can be further purified by other standard techniques, e.g., high performance liquid chromatography. In another embodiment, a mutant CocE polypeptide is expressed as a fusion protein containing an affinity tag (e.g., His×6) that facilitates its purification (see e.g. Example 1).

Pegylation of Mutant CocE Polypeptides

The mutant CocE can be pegylated so as to increase the duration of action and heat stability, and decrease immunogenicity. Pegylation can further enhance the thermostability of the mutant CocE of the invention and increasing serum half life by decreasing renal clearance, proteolysis, macrophage uptake, and immunological response.

Pegylation is the process of attaching repeating units of ethylene glycol (i.e., polyethylene glycol, or PEG) to a polypeptide to reduce the polypeptide's immunogenicity and its rate of renal clearance (see generally (Veronese, F M and Harris, J M (2002b) Advanced Drug Delivery Reviews 54, 457-606, Veronese, F M and Harris, J M (2002c) Advanced Drug Delivery Reviews 55, 1259-1345, reviewing PEGylation technology). Each ethylene glycol unit can bind to two or three water molecules, which effectively increases the size of the peptide, and can protect the peptide from immune responses, enzymatic degradation, and/or rapid renal clearance. The polyethylene glycol can also stabilize against changes in temperature and pH. The net result is that the therapeutic polypeptide can be maintained longer in the blood, and induces a lesser immune response (Harris, J M and Chess, R B (2003) Nature Reviews. Drug Discovery 2, 214-221). PEG possesses a unique set of properties, including absence of toxicity, antigenicity, and immunogenicity, a mass-dependent diminution of renal clearance, and a high flexibility and solubility in water. It imparts these characteristics to the proteins to which it is bound (Veronese, F M and Harris, J M (2002b) Advanced Drug Delivery Reviews 54, 457-606).

A PEG polymer can first be activated with a functional group that encourages covalent binding to an amino acid of the protein. The terminal hydroxyl group of the PEG can be modified by an active carbonate, active ester, aldehyde or tresylate derivative. The PEG can be attached to lysines or to introduced cysteine residues of the mutant CocE. Repeating units of ethylene oxide can be constructed in many configurations having different lengths, with or without branching, and with various molecular weights. Means of incorporation can include site-directed mutagensis or use of maleimide derivatives of transglutaminase.

PEG is FDA approved for use as a vehicle or base in pharmaceuticals, including injectable, topical, rectal and nasal formulations (Harris and Chess, 2003). And PEGylated drugs have been approved for clinical use (see e.g., PEG-interferon alpha-2a (Hamidi, M and Tajerzadeh, H (2003) Drug Delivery 10, 9-20; PEG-interferon alpha-2b (Reddy et al. (2002) Advanced Drug Delivery Reviews 54, 571-586).

Owing to the unparallel spatial dynamic mobility of PEG, modification of the surface of a mutant CocE by the PEG polymer can shield the coated enzyme from actions by the proteolytic enzymes and recognition by the immune system; thereby reducing the immunogenicity and prolonging the circulating half-life of the pegylated mutant CocE. Success of pegylation strategies include PEG-modified liposomes (i.e., stealth liposomes, so termed due to their ability in dodging immune detection and renal clearance to yield a significantly extended circulating time (Lasic, D D (1997) Journal of Controlled Release 48, 203-222), as well as pegylated asparaginase whose in vivo half-life has been drastically improved from 26 hours seen for free asparaginase to 15 days (Avramis et al. (2002) Blood 99, 1986-1994). Further, it is recognized in the art that pegylation can significantly enhance the thermal stability of an enzyme (Kazan, D. and Erarslan, A. (1997) Applied Biochemistry & Biotechnology 62, 1-13; Efremova et al. (1998) Biochemistry (Moscow) 63, 441-447) and reduce activation of the complement system (Chang et al. (2005) Bioconjugate Chemistry 16, 147-155). Thus, PEGylation technology is well suited to improve the pharmacological and pharmaceutical effects of the mutant CocE of the invention (see e.g., Example 11). Pegylation of mutant CocE can also be used in conjunction with RBC encapsulation.

Encapsulating Mutant CocE in RBC

The mutant CocE can be encapsulated into red blood cells (RBC) so as to increase the duration of action and heat stability, and decrease immunogenicity. Cocaine, just as it rapidly crosses the blood-brain barrier, also rapidly transits the RBC plasma membrane, and this uptake has been demonstrated in a study of intravenous cocaine administration in man (Javaid et al. (1978) Journal of Chromatography 15, 105-113). Furthermore, cocaine concentrations in RBC exceed the concentrations in plasma (Javaid et al. (1978) Journal of Chromatography 15, 105-113). As such, RBC encapsulation can be utilized to shield thermostable forms of CocE from clearance.

Erythrocytes have been exploited extensively for their potential applications as drug carriers (Wang et al. (2002) Advanced Drug Delivery Reviews 54, 547-570). Being the most abundant cells of the human body, RBC offers unmatched advantages to function as a drug carrier. First, erythrocytes are completely biocompatible and biodegradable, particularly when the autologous cells are used for drug loading. In addition, the biconcave disk shape of erythrocytes provides them with the highest surface to volume ratio ($1.9\times10^4$ cm/g) (Guyton, A G & Hall, J E (1996) Textbook of Medical Physiology, 425-433) usable for drug encapsulation. Encapsulation in RBC also prevents the loaded drug from inactivation by endogenous factors as well as protects the organisms from toxic effects of the encapsulated drug (Wang et al. (2002) Advanced Drug Delivery Reviews 54, 547-570). Furthermore, RBC encapsulation enables avoidance of undesirable immune responses (i.e. antigenicity and immunogenicity) that may be triggered by foreign bodies (Wang et al. (2002) Advanced Drug Delivery Reviews 54, 547-570). And, erythrocytes possess longer circulation half-life in comparison to other synthetic carriers. For example, the normal lifespan of an erythrocyte in systemic circulation is reported to be about 120 days (Guyton, A G & Hall, J E (1996) Textbook of Medical Physiology, 425-433).

Encapsulation of mutant CocE in erythrocytes can be according to several techniques known in the art, including electroporation, drug (e.g., primaquine)-induced endocytosis, and osmosis (see e.g., Green, R. and Widder, K J (1987) Methods In Enzymology, Vol. 149). These methods can include swelling and disrupting the cell membrane, releasing the interior content including primarily hemoglobin and also cytoskeleton, entrapping the drug, and then resealing the membrane to yield the cup-shaped, spherical, pink or white-colored RBC (generally termed "RBC-Ghost").

Alternatively, membrane-penetrating peptides can be employed to encapsulate mutant CocE in erythrocytes (see e.g., Example 12). Membrane-penetrating peptides, or protein transduction domain (PTD) peptides are a family of small (normally consists of 10-15 amino acid residues) peptides including TAT, LMWP, and other arginine-rich cationic peptides (see generally, Dietz, G P H and Bahr, M (2004) Molecular Cell Neurosciences 27, 85-131). It is known to the art that, by covalently linking PTD to almost any type of molecular species including proteins (MW>150 kDa; more than 60 different proteins have already been tested (Dietz, G P H and Bahr, M (2004) Molecular Cell Neurosciences 27, 85-131) and nano-carriers (e.g. liposomes), PTD can ferry the attached species across cell membrane of all organ types including the brain (Schwarze et al. (1999) Science 285, 1569-1572). PTD is neither toxic nor immunogenic (Schwarze et al. (1999) Science 285, 1569-1572), and the PTD-mediated cell internalization does not induce perturbation or alteration of the erythrocytes cell membrane (Suzuki et al. (2002) Journal of Biological Chemistry 25, 2437-2443). PTD has been used successfully in protein loading RBC, and results in erythrocytes with unaltered physical and chemical attributes (see e.g., Li et al. (2003) American Pharmaceutical Review 6, 22-26). Thus, PTD peptide conjugation to mutant CocE can facilitate RBC encapsulation. RBC encapsulation can also be carried out by using pegylated mutant CocE.

Stabilizing Mutant CocE

Another aspect of the invention is directed toward stabilization of mutant CocE polypeptides using substrates, products, and/or inhibitors of cocaine. Substrates and products useful in embodiments disclosed herein include, for example, but are not limited to, cocaine; cocaine derivatives, such as, for example, (−)-cocaine, (+)-cocaine, tropococaine, and the like; thio-cocaine derivatives, such as, for example, Thiol-1, Thiol-2, and the like; amide-cocaine derivatives; provitamin-cocaine derivatives, such as PABA cocaine, Niacin cocaine, and the like; benzoic acid; 4-nitrophenyl acetate (4NPA); 4-nitrophenol (4NP); and the like. Exemplary inhibitors include, but are not limited to, substrate analogues, such as, phospho-fluorococaine, O-Phospho-cocaine, O-methylphosphococaine, S-Methylphophococaine, and the like; product analogues, such as, Ecgonine and Ecgonine derivatives, such as, boronic acid ecogonine methylester analog; phenylboronic acid; benzoic acid derivatives, such as, 4-tert-Butyl benzoic acid, 1-Naphthoic acid, 2,3,4-trimethyl-benzoic acid methyl ester, and the like. Additional chemicals include, for example, but are not limited to, SDS, glycerol, PEG, and the like.

Preferably, the substrates, products, and/or inhibitors stabilize thermal denaturation of the polypeptides disclosed herein. In some embodiments, the substrates, products and/or inhibitors also prevent thermally-induced aggregation in gel electrophoresis. Generally, use of a substrate, product, and/or inhibitor results in at least about a 10% increase in stability and/or inhibition, respectively. For example the increase can be about 15%, 20%, 25%, 30%, 35%, 40%, 45%, 50%, 55%, 60%, 65%, 70%, 75%, 80%, 85%, 90%, 95%, 100%, 120%, 150%, 200%, 300%, or even 500% or greater. Thus, substrates, products, and/or inhibitors are well suited to stabilize the mutant CocE polypeptides disclosed herein (see e.g., Example 20).

In one embodiment, small molecules are used to thermo-stabilize the mutant CocE polypeptides disclosed herein. In a preferred embodiment, such molecules do not occupy the active site of the polypeptide.

In some embodiments, the polypeptides disclosed herein can be co-infused with a stabilizing molecule. In other embodiments, the stabilizing molecules can be used to stabilize the polypeptide during manufacturing. In still other embodiments, the stabilizing molecules can be used to stabilize the mutant CocE polypeptides until ready for use.

Treatment Methods

Another aspect of the invention is directed toward catalytic degradation approach to anti-cocaine therapeutics. Provided are treatments, both prophylactic and therapeutic, of cocaine-induced conditions through the administration of thermo-stable, esterase active, mutant CocE polypeptides to a subject in need thereof. The cocaine esterase variants of the invention hold significant clinical value because of their increased thermostability and longer plasma half-life than known naturally occurring CocE. It is this increase in thermostability and plasma half-life that enables a much more rapid response to the life-threatening symptoms of cocaine toxicity that sets the CocE variants of the invention apart from other treatment options.

A determination of the need for treatment will typically be assessed by a history and physical exam consistent with the cocaine-induced condition. Cocaine-induced conditions include, but are not limited to, cocaine overdose, cocaine toxicity, and cocaine dependence and/or addiction. For example, the diagnosis of cocaine toxicity can include convulsions, grand-mal seizures, cardiac arrest, myocardial infarction, cardiac arrhythmias, increased blood pressure, stroke, drug-induced psychosis, dissecting aneurysm, and increased myocardial oxygen demand. As another example, in the case of cocaine dependence and/or addiction, withdrawal symptoms include subjective sensations of mild to severe dysphora, depression, anxiety, or irritability. Subjects with an identified need of therapy include those with a diagnosed cocaine-induced condition, an indication of a cocaine-induced condition, and subjects who have been treated, are being treated, or will be treated for a cocaine-induced condition. The subject is preferably an animal, including, but not limited to, mammals, reptiles, and avians, more preferably horses, cows, dogs, cats, sheep, pigs, and chickens, and most preferably human.

An effective amount of the mutant CocE polypeptides described herein is generally that which can reduce the cocaine-toxicity or the severity of a cocaine-induced condition. Reduction in severity includes, for example, an arrest or a decrease in symptoms, physiological indicators, biochemical markers, or metabolic indicators. When used in the methods of the invention, a therapeutically effective amount of mutant CocE polypeptide described herein can be employed in pure form or, where such forms exist, in pharmaceutically acceptable salt form and with or without a pharmaceutically acceptable excipient. For example, the mutant CocE polypeptides of the invention can be administered at a reasonable benefit/risk ratio applicable to any medical treatment, in an amount sufficient to substantially reduce the cocaine concentration in the blood and/or tissues of the subject.

Toxicity and therapeutic efficacy of mutant CocE polypeptides can be determined by standard pharmaceutical procedures in cell cultures and/or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where large therapeutic indices are preferred.

The amount of mutated CocE polypeptide that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses. Agent administration can occur as a single event or over a time course of treatment. For example, an agent can be administered daily, weekly, bi-weekly, or monthly. For some conditions, treatment could extend from several weeks to several months or even a year or more.

The specific therapeutically effective dose level for any particular subject will depend upon a variety of factors including the cocaine-induced condition being treated and the severity of the cocaine-induced condition; activity of the mutant CocE polypeptide employed; the specific composition employed; the age, body weight, general health, sex and diet of the patient; the time of administration; the route of administration; the plasma half-life of the mutant CocE polypeptide; the rate of excretion of the mutant CocE polypeptide employed; the duration of the treatment; drugs used in combination or coincidental with the mutant CocE polypeptide employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4$^{th}$ ed., Lippincott Williams & Wilkins, ISBN 0781741475; Sharqel (2004) Applied Biopharmaceutics & Pharmacokinetics, McGraw-Hill/Appleton & Lange, ISBN 0071375503). It will be understood by a skilled practitioner that the total daily usage of the mutant CocE polypeptide for use in embodiments of the invention disclosed herein will be decided by the attending physician within the scope of sound medical judgment.

Mutant CocE polypeptides described herein can also be used in combination with other therapeutic modalities. Thus, in addition to the therapies described herein, one can also provide to the subject other therapies known to be efficacious for particular cocaine-induced conditions.

The mutant CocE polypeptides described herein can be formulated by any conventional manner using one or more pharmaceutically acceptable carriers and/or excipients (see e.g., Gennaro (2005) Remington the Science and Practice of Pharmacy 21st ed. Lippincott Williams & Wilkins, ISBN 0781746736). Such formulations will contain a therapeutically effective amount of the mutant CocE polypeptide, preferably in purified form, together with a suitable amount of carrier so as to provide the form for proper administration to the subject. The formulation should suit the mode of administration. Mutant CocE polypetides of use with the current invention can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The mutant CocE polypeptide can also be administered in combination with one or more additional agents disclosed herein and/or together with other biologically active or biologically inert agents. Such biologically active or inert agents can be in fluid or mechanical communication with the agent(s) or attached to the agent(s) by ionic, covalent, Van der Waals, hydrophobic, hydrophillic or other physical forces.

Mutant CocE polypeptides described herein can be administered parenterally, including intravenous, intramuscular, subcutaneous, and intraperitoneal injections. Excipients, commonly used in the parenteral delivery of small drug molecules, including solubility enhancers, osmotic agents, buffers, and preservatives, can also be included in biomolecule formulations. Inclusion of antiaggregation and antiadsorption agents, such as surfactants and albumin, when formulating and delivering biomolecules can add increased stability and decrease the risk of the active biomolecule interacting with an interface, which can lead to unfolding, aggregation, and/or precipitation. The mutant CocE polypeptide can be lyophilized for added stability during storage, and re-processed before parenteral administration.

Preferably, the mutant CocE polypeptide is pegylated, thus providing increased stability and lessened immunogenicity (see above).

Pulmonary delivery of macromolecules, such as mutant CocE polypeptides, provide for relatively easy, non-invasive administration to the circulatory system for systemic distribution (see e.g., Cryan (2004) AAPS J. 7(1) article 4, E20-41, providing a review of pulmonary delivery technology). Advantages of pulmonary delivery include noninvasiveness, large surface area for absorption (~75 $m^2$), thin (~0.1 to 0.5 μm) alveolar epitheliuem permitting rapid absorption, absence of first pass metabolism, decreased proteolytic activity, rapid onset of action, and high bioavailablity. Various inhalation delivery devices, such as metered-dose inhalers, nebulizers, and dry-powder inhalers, that can be used to deliver the biomolecules described herein are known to the art (e.g., AErx (Aradigm, CA); Respimat (Boehringer, Germany); AeroDose (Aerogen Inc., CA)). Dry powder inhalation devices are particularly preferred for pulmonary delivery of protein-based agents (e.g., Spinhaler (Fisons Pharmaceuticals, NY); Rotohaler (GSK, NC); Diskhaler (GSK, NC); Spiros (Dura Pharmaceuticals, CA); Nektar (Nektar Pharmaceuticals, CA)).

Controlled-release (or sustained-release) preparations can be formulated to extend the activity of the mutant CocE polypeptide and reduce dosage frequency. Controlled-release preparations can also be used to effect the time of onset of action or other characteristics, such as blood levels of the agent, and consequently affect the occurrence of side effects. Controlled-release preparations can be designed to initially release an amount of mutant CocE polypeptide that produces the desired therapeutic effect, and gradually and continually release other amounts to maintain the level of therapeutic effect over an extended period of time. In order to maintain a near-constant level of mutant CocE polypeptide in the body, the agent can be released from the dosage form at a rate that will replace the amount of agent being metabolized and/or excreted from the body. The controlled-release of an agent can be stimulated by various inducers, e.g., change in pH, change in temperature, enzymes, water, or other physiological conditions or molecules.

Controlled-release systems can include, for example, an infusion pump which can be used to administer the agent in a manner similar to that used for delivering insulin or chemotherapy to specific organs or tumors. The agents of the invention can be administered by other controlled-release means or delivery devices that are well known to those of ordinary skill in the art, including, for example, hydropropylmethyl cellulose, other polymer matrices, gels, permeable membranes, osmotic systems, depots, multilayer coatings, microparticles, liposomes, microspheres, or the like, or a combination of any of the above to provide the desired release profile in varying proportions. Other methods of controlled-release delivery of agents will be known to the skilled artisan and are within the scope of the invention.

Mutant CocE polypeptides can be encapsulated and administered in a variety of carrier delivery systems. Carrier-based systems for biomolecular agent delivery can: provide for intracellular delivery; tailor biomolecule/agent release rates; increase the proportion of biomolecule that reaches its site of action; improve the transport of the drug to its site of action; allow colocalized deposition with other agents or excipients; improve the stability of the agent in vivo; prolong the residence time of the agent at its site of action by reducing clearance; decrease the nonspecific delivery of the agent to nontarget tissues; decrease irritation caused by the agent; decrease toxicity due to high initial doses of the agent; alter the immunogenicity of the agent; decrease dosage frequency, improve taste of the product; and/or improve shelf life of the product.

Examples of carrier delivery systems for with mutant CocE polypeptides described herein include microspheres (see e.g., Varde & Pack (2004) Expert Opin. Biol. 4(1) 35-51), hydrogels (see generally, Sakiyama et al. (2001) FASEB J. 15, 1300-1302), polymeric implants (see generally, Teng et al (2002) Proc. Natl. Acad. Sci. U.S.A. 99, 3024-3029), smart ploymeric carriers (see generally, Stayton et al. (2005) Orthod Craniofacial Res 8, 219-225; Wu et al. (2005) Nature Biotech (2005) 23(9), 1137-1146), and liposomes (see e.g., Galovic et al. (2002) Eur. J. Pharm. Sci. 15, 441-448; Wagner et al. (2002) J. Liposome Res. 12, 259-270). Preferably, the mutant CocE polypeptide is encapsulated in RBC (see above; Example 12).

Screening Methods

Another aspect of the invention is directed toward screening methods for the generation, identification, and purification of thermostable mutant CocE polypeptides. Generally, mutant CocE polypeptides can be initially designed according to the approaches described above. Such designed polypeptides can then be screened for preferred characteristics, such as retention of hydrolytic efficiency, increased thermostability, increased plasma-half-life, and/or reduced antigenicity. Also, random mutant CocE polypeptides can be screened for the desired characteristics.

Detection methods to screen for thermostable mutants encompass a wide variety of techniques. The following is an exemplary summary of a generic protocol. Nucleic acid encoding the mutant CocE polypeptides (generated, for example, through rational design, random mutagenesis, or host mutagensis) is transformed into an appropriate expression host (for example, E. coli cells such as E. coli BL21 Gold (Stratagene)), and expression of the mutant polypeptide is induced according to standard protocols (e.g. by IPTG). Expression is performed at temperatures to produce optimal protein expression (e.g., 16° C. for CocE, see e.g., Example 1) for a pre-determined period of time (e.g., anywhere from 30 minutes to 24 hours or longer). Alternatively, expression is performed at an elevated temperature (for example, the elevated temperature can be at least about 35° C., at least about 36° C., at least about 37° C., at least about 38° C., at least about 39° C., at least about 40° C., or even higher). Preferably, the elevated temperature at which mutated CocE polypeptide is expressed is 37° C. Around this temperature, wild-type CocE polypeptide partitions almost exclusively into inclusion bodies. Cells containing the expressed mutant polypeptides are screened for the presence of thermostable variants of CocE.

Screening for the presence of thermostable variants of CocE generally involves either direct measurement on cultured cells, on cell lysates, or following cellular disruption and isolation of the mutant CocE polypeptide. Cellular disruption can include osmotic shock, chemical lysis, sonication, and/or homogenization, and isolation of the mutant polypeptide can be obtained through numerous methods including either direct absorption to a matrix or affinity absorption through the use of anti-cocaine antibodies or fusion-protein specific capture systems. Suitable matrix for absorption includes nitrocellulose paper, filters, untreated or affinity-treated microtiter plates, agarose or sepharose resins, and/or affinity-coated tips.

The esterase activity of the cultured cells or isolated mutant polypeptide can be subsequently measured at one or more temperatures to determine the thermostability of the mutants. The temperature at which the activity assay is performed determines the degree of thermostability detection. Thus, while the final mutants will preferably have a melting temperature of 45° C. or higher (as determined by, for example, circular dichroism), often, the initial screening at 45° C. will not find active enzymes. Rather, several cycles of mutagenesis and screening at subsequently increasing temperatures can be performed to acheive thermostable mutants. Thus, initial screening can be performed at 30° C., and after further cycles of mutagenesis, screening can be performed with incrementally increasing temperatures (for example, 34° C., 37° C., 40° C., 42.5° C., 45° C., etc.), until a mutant of suitable thermostability is achieved. The incremental temperature increases are determined empirically during the procedure, and are affected by the number of hits at particular temperatures and the determined Tm of the generated mutants.

While under no obligation to do so, and while not wishing to be bound by theory, herein follows what is believed to be a mechanistic explanation of melting of various embodiments of mutant CocE polypeptides described herein. CD spectra data illustrate that the CD melting of cocaine esterase and mutants is irreversible, as cooling to 0 degrees does not reform the original spectra (see, e.g., Example 19). While thermodynamic parameters cannot be ascertained, CD spectra can be used to comparatively determine whether mutants are more or less stable, whether they have different secondary structures or aggregation properties. It is believed that the CocE polypeptides described herein melt via an intermediate step, that is, the polypeptides undergo a 2-step melting process.

Detection of esterase activity can be performed using a variety of methods, where substrates are coupled to a specific detection system. Appropriate substrates for use in determining esterase activity can include cocaine, tritiated (3H) cocaine, cocaine substrate derivatives such as a thio-cocaine derivative (see e.g., FIG. 6), and/or substrates that report general esterase activity such as 4-nitrophenyl acetate. The detection system can be directly coupled to the specifics of the substrate, for example: cleavage of unmodified cocaine can be detected by monitoring changes in cocaine absorbance at 240 nm (see e.g., Example 4), or by monitoring pH changes that result from the accumulation of the acidic benzoic acid product (see e.g., Example 15), or through the use of cocaine aptamers (see e.g., Stojanovic, M. N., de Prada, P. & Landry, D. W. (2001) J Am Chem Soc 123, 4928-4931; Stojanovic, M. N. & Landry, D. W. (2002) J Am Chem Soc 124, 9678-9679) by monitoring changes in fluorescence upon degradation of cocaine (see example 15); cleavage of tritiated (3H) cocaine can be detected by acidification and detection of tritiated benzoic acid product through separation by chromatography (see example 1 and 15); cleavage of cocaine derivatives such as thio-cocaine can be monitored by the detection of reactive sulfhydryl groups, through the addition of Ellman's reagent and determination of absorbance changes at 412 nm (see e.g., Example 15), or by the addition and visualization of precipitating sulfhydryl reacting heavy metals; cleavage of 4-nitrophenyl acetate can be detected by monitoring changes in absorbance at 420 nm (see e.g., Halgasova, N. et al. (1994) Biochem J 298 Pt 3, 751-755; O'Conner, C. J. & Manuel, R. D. (1993) J Dairy Sci. 76, 3674-3682).

Mutant CocE polypeptides identified through the above procedures, or a similar high throughput assay, can be further evaluated using in vitro procedures described herein (e.g., Kcat and Km values, stability at 37°, melting temperature (Tm), endotoxin levels, ability to degrade cocaine in plasma). Mutant CocE polypeptides with thermostable esterase activity and/or reduced immunogenicity, can be further evaluated using in vivo procedures described herein (e.g., potency, duration of action, effects with repeated dosing, and/or immunological evaluation). Preferably, mutant CocE polypeptides magnitudinal decrease of cocaine toxicity is examined first (see e.g., Examples 5, 7, and 8), and those mutants that reduce toxicity by at least about 5-10 fold can be further evaluated for time course of action (see e.g., Example 6). Candidate mutant CocE polypeptides can be further stabilized by, for example, pegylation and/or encapsulation in RBC and re-evaluated in the above described procedures.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate various embodiments of the invention disclosed herein. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

CocE Expression

Figure 3:
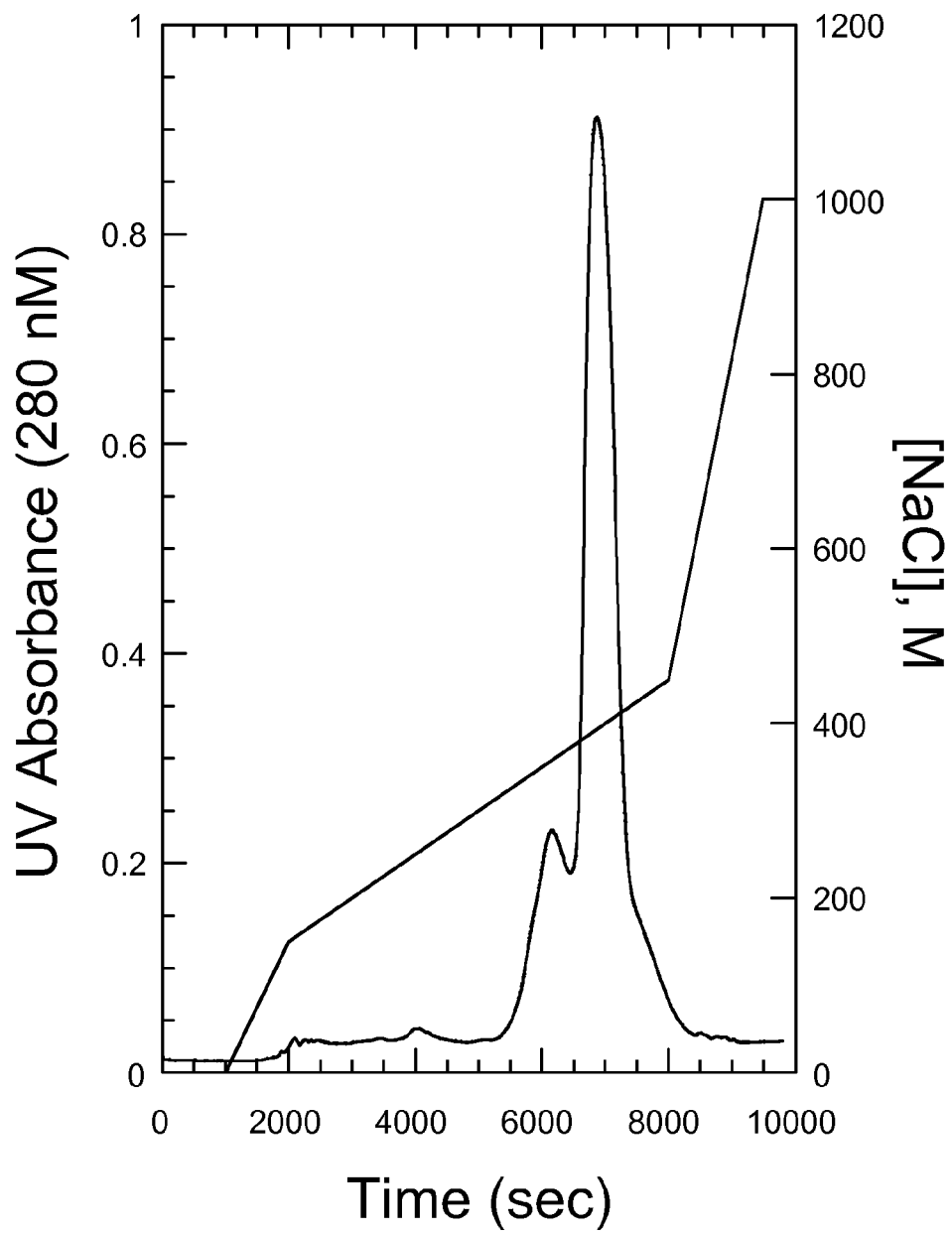
FIG. 3 is a line plot depicting the elution profile for CocE by FPLC (Q-Sepharose), where UV absorbance and sodium chloride concentration is shown over time. For further methodology information, see Example 1.

A method for expression and purification of CocE was established, where CocE is expressed in *E. Coli* as a fusion protein with a carboxyl terminus His×6-tag. The cocaine esterase gene was subcloned into the *E. coli* expression vector pET-22b(+) and high levels of cocaine esterase enzyme containing a C-terminal histidine tag were induced upon the addition of IPTG at 23 C. The recombinant protein accumulated to approximately 10-15% of total protein. CocE was enriched on either a cobalt-chelate column (Talon™ Clontech) or a nickel-chelated agarose column (Pierce) by virtue of the His×6 tag. The eluted protein was approximately 95% pure by SDS-PAGE and Coomassie blue staining, and was subsequently resolved by ion-exchange chromatography FPLC column (Q-Sepharose) using an NaCl gradient. The protein eluted as a single peak was approximately 99% pure, as indexed by SDS-PAGE and Coomassie blue staining (see e.g., FIG. 3).

Enzyme activity was determined through two assays: a radio-ligand activity assay in which tritated cocaine was hydrolyzed and then after acidification, the tritated benzoic acid product was separated from tritiated cocaine hydrochloride by chromatography; and a spectrophotometric asay under similar conditions as described by Turner et al. (2002) Biochemistry 41, 12297-12307. The unique absorption spectra of cocaine (extinction coefficient 6.7 L/mmol/cm, at 240 nm) allows for the observation of remaining cocaine following enzymatic cleavage. The initial linear rates of decay of cocaine, representing velocity, were determined in a SpectraMax 190 plate reader (Molecular Devices) using SOFTmax Pro software (v1.13). The reaction was initiated by adding 150 µL of a 2× enzyme solution to the 150 µL of a 2× cocaine solution. Final CocE concentrations ranged from 100 ng/mL to 20 ng/mL. Final cocaine concentrations were as follows: 250, 126, 62.5, 31.25, 15.63, 7.81, 3.91, and 1.95 µM. For the kinetics of all enzymes, the buffer was phosphate buffered saline, pH 7.4. Initial rates were fitted to the Michaelis-Menten equation, with kcat and Km as adjustable parameters (GraphPad; PRISM, v4).

As determined using the cocaine spectrophotometric assay, the purified wild-type CocE polypeptide hydrolyzes cocaine with a Kcat of approx. 500 $min^{-1}$ and a Km of approx. 2 µM, which is consistent with previously reported values (see e.g., Turner et al. 2000).

Such expression procedures can be utilized for the mutant CocE polypeptides described herein.

Example 2

Ex Vivo CocE Plasma Activity

Ex vivo determination of cocaine levels following cocaine esterase was examined in human plasma (University of Michigan Hospital blood bank). Cocaine was obtained from The National Institute of Drug Abuse (Bethesda, Md., USA). Cocaine was disolved in sterile water. Aliquots (3 ml) of human plasma were maintained at 37° C. in a water bath for 10 minutes prior to the start and for the duration of the experiment. After equilibrating plasma in water bath, cocaine was added to a final concentration of 300 µM and vortexed for 30 seconds. Plasma samples were removed and placed in a microcentrifuge tube containing the internal standard and a saturated sodium fluoride solution to prevent further cocaine metabolism. Immediately after taking the first plasma ample (cocaine alone), 0.05 mg/ml CocE or vehicle CocE was added and vortexed. Plasma samples were collected at 1, 2, 4, 6, 8, 10, 15, 30, 45, 60, and 120 minutes after adding CocE. Levels of cocaine were measured using high performance liquid chromatography tandem mass spectrometry.

Liquid chromotography was performed using a Surveyor HPLC system (ThermoElectron Corp., Franklin, Mass.) with a quanternary pump and autosampler configured with a 10 µl injection loop. Separation was achieved using a Phenomex C18 3 µm 30×4.6 mm column with corresponding guard column (Waters Corp., Milford, Mass.) at a flow rate of 600 µl/min. Solvent A consisted of a 0.1% formic acid solution, and solvent B was 0.1% formic acid in acetonitrile (high purity grade; Burdick and Jackson, Muskegon, Mich.). A 3 minute ballistic gradient was used with cocaine and the internal standard co-eluting at 2.3 min.

For detection and quantification by mass spectrometry, a Finnigan TSQ Quantum Ultra AM triple quadrapole mass spectrometer equipped with an IonMax electrospray ionization source (ThermoElectron Corp., Franklin, Mass.) was used in positive ion, selected reaction monitoring mode. Nitrogen served as the nebulizing gas and argon as the collision gas. Gas flow rates, spray voltages, and collision energies were optimized. Calibration curves were determined for cocaine with 50 nM deuterated cocaine (cocaine $D_3$) as the internal standard in untreated plasma samples. Unknown samples were also spiked with cocaine $D_3$. All samples were evaluated in triplicate. Standard curves and unknowns were analyzed by Quan Browser program in Xcalibur version 1.4 (ThermoElectron Corp., Franklin, Mass.) software. Calibration curves were constructed using linear regression of cocaine peak area/internal standard area ratio as a function of standard concentration with a weighting factor of 1/x. Standard curve fit values were accepted at a value is greater than 0.99, and RSD values for replicate samples are between 0-10%.

Figure 4:
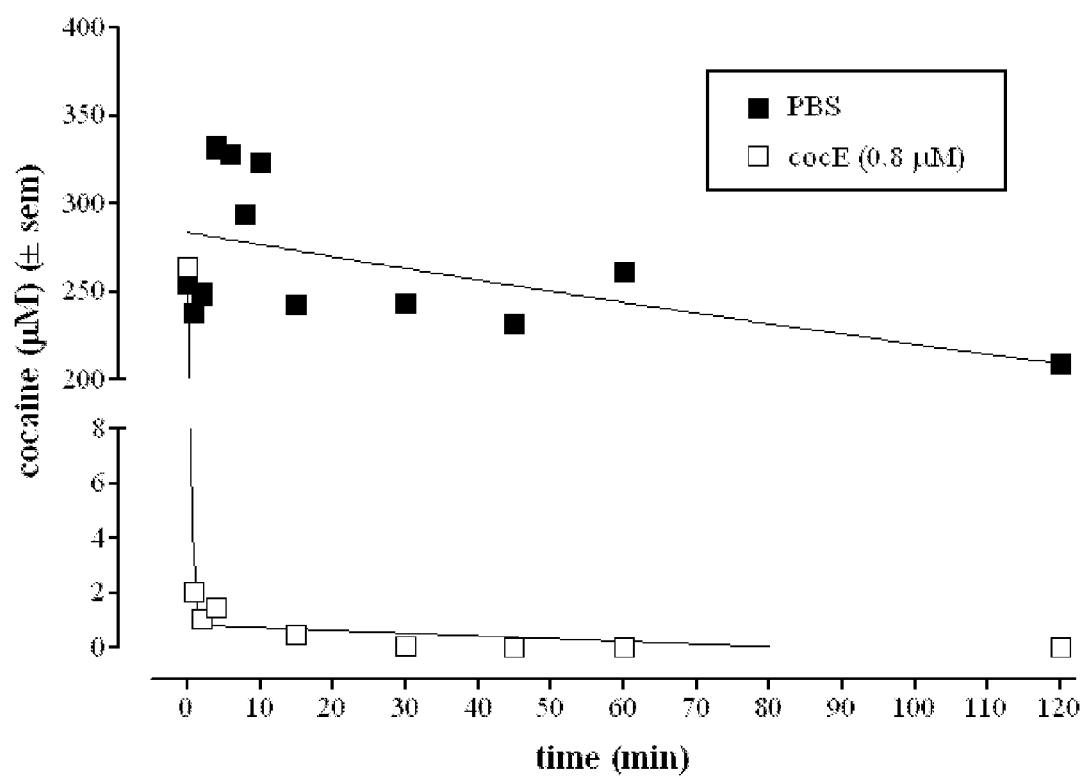
FIG. 4 is a line and scatter plot showing the in vitro degradation of cocaine in the presence of CocE in human plasma. For further methodology information, see Example 2.

Results demonstrate that CocE is able to degrade cocaine very rapidly when the two are mixed briefly in human plasma (see e.g., FIG. 4). The first time point indicates the cocaine concentration prior to the addition of cocaine esterase or esterase vehicle. Prior to esterase treatment, cocaine levels were similar, but within 1 min of cocaine esterase administration, cocaine levels were decreased at least 100-fold to approximately 2 µM as compared with the vehicle-treated plasma sample. Cocaine levels continued to decrease in the esterase-treated plasma samples, falling below 1 microM by the 2-minute timepoint.

The therapeutic efficiency of the enzyme was demonstrated by the increasing dose of cocaine required to produce toxic effects after a single intravenous injection of CocE. The wild-type enzyme demonstrated rapid kinetics for cocaine degradation ex vivo in rat and human serum. Two inactive mutants of CocE failed to protect the rats from the toxic effects of cocaine, confirming the protective effects are due to hydrolytic activity. Furthermore, CocE did not change the lethality of WIN-35065-2, a cocaine analog that lacks the benzoyl ester moiety targeted by CocE. The in vivo and ex vivo characterization of CocE supports the role of the enzyme as a suitable antidote to toxicity in humans.

Example 3

Predicted Thermostable Mutant CocE

Figure 2:
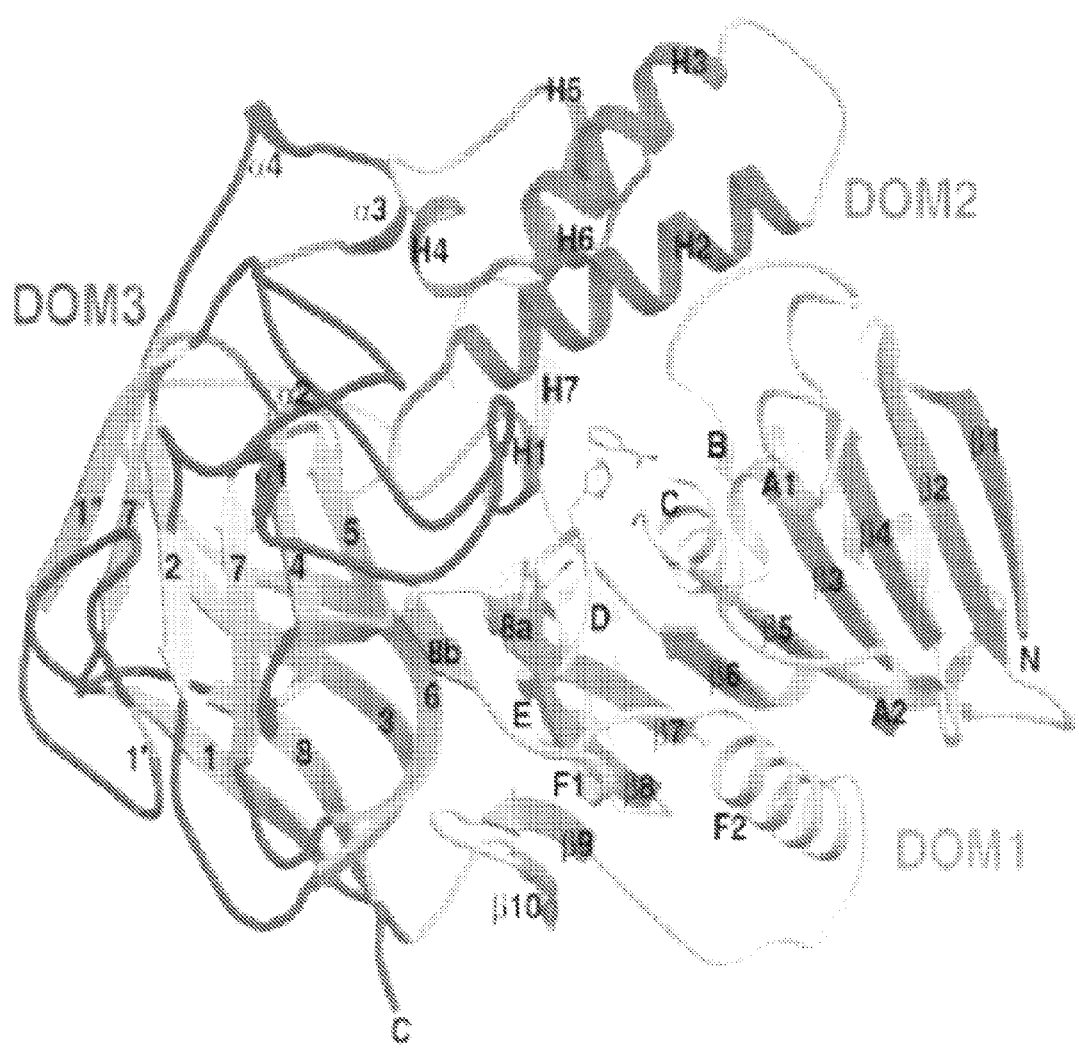
FIG. 2 is a ribbon diagram illustrating the CocE structure. Domain 1 (DOM1), domain 2 (DOM2), and domain 3 (DOM 3) are indicated, along with the active site located at the intersection of the three domains. A benzoic acid molecule is shown in the active site.

Rational design of mutant CocE described herein was based upon molecular dynamics (MD) simulations. A computational model of CocE was constructed using the published crystal structure of wild-type CocE (see e.g., FIG. 2). Such models can be used to identify certain amino acid modifications that increase the theoretical melting temperature of the protein without disrupting the structure at the active site. Classical MD simulation enables the study of time evolution of a large system by taking many small successive time steps under atomic forces determined by a set of parameterized interaction functions (force field), including bonded interactions (bonds, angles, and dihedral angles), non-bonded van der Waals interactions, and electrostatic interactions based or net atomic charges. Due to the simple force field form the MD simulation may be performed for a sufficiently long simulation time to give meaningful ensemble-averaged properties, even for a very large system involving over a hundred thousand atoms. So, for CocE and each proposed mutant, the MD simulation will lead to a reasonable, dynamically averaged 3D structure of the simulated polypeptide in water.

Based on the X-ray crystal structure (PDB code 1JU3) of the bacterial cocaine esterase (CocE) (Larson et al. (2002) Nature 9, 17), a complete 3D model of CocE binding with (−)-cocaine suitable for computational modeling its thermodynamic stability was built. To increase the thermostability of CocE, a computational method was implemented in RosettaDesign program (Kuhlman and Baker (2000) PNAS 97, 10383) capable of predicting thermostabilizing mutations within a given fold while minimizing any shift in the backbone that might structurally disrupt the active site structure or quench its flexibility. The method implemented in the RosettaDesign program uses an energy function for evaluating the fitness of a particular sequence for a given fold and a Monte Carlo search algorithm for sampling sequence space. A similar method has been successfully used by other researchers to increase thermostability of an enzyme with no reduction in catalytic efficiency (Korkegian et al. (2005) Science 308, 857). The partial atomic charges for the non-standard residue atoms were calculated by using the standard RESP protocol implemented in the Antechamber module of the Amber7 (or 8) program package (Case, 2002). The computational modeling using the RosettaDesign program allowed prediction of a set of CocE mutations calculated as having lower energy and, therefore, increased thermostability (see e.g., Table 2). For this example, computation considered only possible mutations on the amino acid residues having a distance of between 6-25 Å from the cocaine substrate molecule.

Identified single mutation CocE polypeptides calculated to stabilize CocE by about 2.1 to about 4.5 kcal/mol included: L163V (SEQ ID NO: 3); V121D (SEQ ID NO: 4); S167A (SEQ ID NO: 5); Q123E (SEQ ID NO: 6); V225I (SEQ ID NO: 7); I218L (SEQ ID NO: 8); A310D (SEQ ID NO: 9); A149S (SEQ ID NO: 10); S159A (SEQ ID NO: 11); S265A (SEQ ID NO: 12); S56G (SEQ ID NO: 13); W220A (SEQ ID NO: 14); T122A (SEQ ID NO: 15); S140A (SEQ ID NO: 16); F189L (SEQ ID NO: 17); A193D (SEQ ID NO: 18); T254R (SEQ ID NO: 19); N42V (SEQ ID NO: 20); V262L (SEQ ID NO: 21); L508G (SEQ ID NO: 22); Y152H (SEQ ID NO: 23); V160A (SEQ ID NO: 24); T172R (SEQ ID NO: 25); Y532F (SEQ ID NO: 26); T74S (SEQ ID NO: 27); W285T (SEQ ID NO: 28); L146P (SEQ ID NO: 29); D533S (SEQ ID NO: 30); A194R (SEQ ID NO: 31); G173Q (SEQ ID NO: 32); C477T (SEQ ID NO: 33); K531A (SEQ ID NO: 34); R41I (SEQ ID NO: 35); L119A (SEQ ID NO: 36); K46A (SEQ ID NO: 37); and F84Y (SEQ ID NO: 38)

TABLE 2

Summary of computational modeling using the RosettaDesign program with consensus approach

| R1 | R2 | R3 | R4 | R5 | R6 | R7 | R8 | R9 | R10 | Consensus mutation | Energy Change (kcal/mol) |
|---|---|---|---|---|---|---|---|---|---|---|---|
| 163 | 163 | 163 | 163 | 163 | 163 | 163 | 163 | 163 | 163 | L163V | −4.5 |
| 121 | 121 | 121 | 121 | 121 | 121 | 121 | 121 | 121 | 121 | V121D | −3.9 |
| 167 | 167 | 167 | 167 | 167 | 167 | 167 | 167 | 167 | 167 | S167A | −3.9 |
| 123 | 123 | 123 | 123 | 123 | 123 | 123 | 123 | 123 | 123 | Q123E | −3.8 |
| 225 | 310 | 310 | 225 | 225 | 225 | 225 | 310 | 225 | 218 | V225I | −3.6 |
| 218 | 225 | 218 | 218 | 218 | 218 | 218 | 225 | 218 | 225 | I218L | −3.5 |
| 310 | 218 | 225 | 310 | 310 | 310 | 310 | 218 | 310 | 152 | A310D | −3.4 |
| 149 | 149 | 152 | 149 | 149 | 149 | 149 | 149 | 310 | 149 | A149S | −3.3 |
| 159 | 159 | 140 | 159 | 159 | 159 | 159 | 159 | 149 | 159 | S159A | −3.3 |
| 189 | 265 | 149 | 265 | 265 | 265 | 265 | 189 | 265 | 265 | S265A | −3.3 |
| 265 | 140 | 265 | 56 | 56 | 56 | 56 | 220 | 265 | 159 | S56G | −3.2 |
| 56 | 220 | 159 | 220 | 220 | 220 | 220 | 122 | 56 | 220 | W220A | −3.2 |
| 220 | 122 | 220 | 122 | 122 | 122 | 122 | 140 | 220 | 56 | T122A | −3.1 |
| 122 | 189 | 122 | 140 | 140 | 140 | 140 | 189 | 122 | 122 | S140A | −3.1 |
| 140 | 193 | 189 | 189 | 189 | 189 | 189 | 193 | 140 | 140 | F189L | −3.1 |
| 254 | 42 | 193 | 193 | 193 | 193 | 193 | 42 | 254 | 189 | A193D | −3.1 |

TABLE 2-continued

Summary of computational modeling using the RosettaDesign program with consensus approach

| R1 | R2 | R3 | R4 | R5 | R6 | R7 | R8 | R9 | R10 | Consensus mutation | Energy Change (kcal/mol) |
|---|---|---|---|---|---|---|---|---|---|---|---|
| 262 | 262 | 42 | 254 | 254 | 254 | 254 | 254 | 42 | 193 | T254R | −3.1 |
| 508 | 508 | 262 | 42 | 42 | 42 | 42 | 262 | 262 | 262 | N42V | −3.0 |
| 152 | 152 | 508 | 262 | 262 | 262 | 262 | 508 | 508 | 508 | V262L | −3.0 |
| 160 | 160 | 198 | 508 | 508 | 508 | 508 | 152 | 152 | 198 | L508G | −2.9 |
| 74 | 198 | 160 | 152 | 152 | 152 | 152 | 160 | 160 | 254 | Y152H | −2.9 |
| 172 | 74 | 74 | 160 | 160 | 160 | 160 | 198 | 198 | 74 | V160A | −2.8 |
| 193 | 172 | 172 | 198 | 198 | 74 | 198 | 74 | 172 | 160 | T172R | −2.8 |
| 532 | 532 | 532 | 532 | 74 | 172 | 74 | 172 | 74 | 172 | Y532F | −2.7 |
| 146 | 146 | 56 | 74 | 172 | 532 | 172 | 532 | 193 | 532 | T74S | −2.7 |
| 285 | 285 | 285 | 172 | 532 | 146 | 532 | 146 | 532 | 285 | W285T | −2.6 |
| 533 | 290 | 146 | 285 | 146 | 285 | 146 | 285 | 285 | 290 | L146P | −2.6 |
| 173 | 254 | 533 | 146 | 285 | 533 | 285 | 533 | 146 | 146 | | |
| 194 | 533 | 173 | 533 | 533 | 173 | 533 | 173 | 533 | 533 | D533S | −2.5 |
| 477 | 56 | 194 | 173 | 194 | 194 | 173 | 194 | 173 | 173 | A194R | −2.4 |
| 531 | 173 | 200 | 194 | 200 | 290 | 194 | 200 | 194 | 194 | G173Q | −2.4 |
| 42 | 194 | 477 | 200 | 290 | 477 | 200 | 290 | 200 | 200 | C477T | −2.4 |
| 119 | 200 | 531 | 290 | 477 | 531 | 477 | 477 | 290 | 477 | K531A | −2.4 |
| 200 | 477 | 305 | 477 | 531 | 200 | 531 | 531 | 477 | 531 | | |
| 41 | 531 | 41 | 41 | 41 | 41 | 41 | 41 | 531 | 42 | R41I | −2.2 |
| 46 | 41 | 119 | 119 | 119 | 119 | 119 | 119 | 41 | 119 | L119A | −2.2 |
| 84 | 119 | 46 | 46 | 173 | 46 | 46 | 46 | 119 | 41 | K46A | −2.1 |
| 305 | 46 | 84 | 84 | 46 | 84 | 84 | 56 | 46 | 46 | F84Y | −2.1 |
| 478 | 57 | 158 | 478 | 84 | 478 | 305 | 84 | 84 | 57 | | |
| 57 | 84 | 307 | 57 | 478 | 57 | 478 | 307 | 478 | 84 | | |
| 87 | 478 | 478 | 142 | 57 | 87 | 57 | 478 | 57 | 158 | | |
| 142 | 87 | 57 | 263 | 87 | 142 | 87 | 57 | 142 | 478 | | |
| 263 | 142 | 142 | 307 | 142 | 263 | 142 | 142 | 263 | 142 | | |
| 307 | 263 | 263 | 78 | 263 | 307 | 263 | 263 | 307 | 263 | | |
| 78 | 307 | 78 | 257 | 307 | 78 | 307 | 78 | 78 | 78 | | |
| 257 | 78 | 257 | 531 | 48 | 257 | 78 | 257 | 257 | 257 | | |
| 290 | 257 | 290 | 49 | 78 | 49 | 257 | 49 | 49 | 49 | | |
| 291 | 201 | 49 | 201 | 257 | 305 | 201 | 201 | 201 | 201 | | |
| 49 | 49 | 201 | 305 | 45 | 291 | 290 | 412 | 305 | 307 | | |
| 176 | 291 | 291 | 412 | 49 | 176 | 291 | 291 | 412 | 291 | | |
| 45 | 305 | 412 | 291 | 201 | 45 | 49 | 176 | 291 | 176 | | |
| 54 | 176 | 176 | 176 | 305 | 54 | 176 | 45 | 45 | 305 | | |
| 406 | 45 | 254 | 45 | 291 | 406 | 45 | 413 | 176 | 45 | | |
| 50 | 54 | 45 | 413 | 176 | 50 | 54 | 54 | 413 | 54 | | |
| | 406 | 54 | 54 | 54 | | 406 | 305 | 54 | 406 | | |
| | 50 | 413 | 50 | 406 | | 50 | 406 | 406 | 50 | | |
| | | 406 | 406 | 50 | | | 50 | 50 | | | |
| | | 50 | | | | | | | | | |

Example 4

Kinetic Parameters of T172R and S159A Mutant CocE

Wild-type CocE and the T172R and S159A mutant CocE polypeptides were tested for catalytic efficiency.

Site directed mutagenesis (QuickChange™, Invitrogen) of CocE was performed to generate the S159A (SEQ ID NO: 11) mutant CocE polypeptide. Cloning and expression techniques used to produce the S159A were the same as in Example 1, except as indicated otherwise. The CocE gene was amplified through Polymerase Chain Reaction (PCR) in the presence of primers that contain the specific mutation required (Integrated DNA Technologies, Inc.). The specific mutation was subcloned back into the expression plasmid and the nucleotide sequence of these plasmids determined to verify the presence of the mutation.

Mutant T172R was generated by overlapping PCR using 5' and 3' primers containing the specific T172R mutation, as well as an additional Sac II restriction enzyme site for easy detection of the mutated gene. Primer pairs CocE 20-5'F-Nde I (5' GATATACATATGGTGGACGGGAATTAC 3') and T172R-3'R (5' CAGACCTCGACGTGATGAGCCCGCG-GCCTATGAGAGCTGACCAGC 3') as well as CocE-1800-3'R (5' GTGGTGCTCGAGTCGCTTGATAATCG 3') and T172R-5'F (5' GCTGGTCAGCTCTCATAGGC-CGCGGGCTCATCACGTCGAGGTCTG 3') were PCR-amplified using the high-fidelity Pfu enzyme (Stratagene) with an annealing temperature of 55° C. Resultant PCR products were combined and re-amplified, generating a full-length CocE gene encoding the T172R mutation. The gene was digested with Nde I and Xho I; subcloned into the expression vector, and sequenced in its entirety to verify both the presence of the mutation and the absence of additional PCR-copy error mutations.

Plasmids containing the mutations were transformed into E. coli BL21 cells and IPTG-induced enzyme was purified on Ni-Agarose. Expressed proteins were then tested for enzymatic activity and for thermostability at 37° C. Enzyme activity was measured using the spectrophotometric asay as described in Example 1. Thermostability was also tested via the spectrophotometric assay by pre-incubation of both wild-type and mutants at 37° C. for various times. Additionally, the nature of the thermo-instability of both the wild-type and T172R mutant was analyzed by polyacrylamide gel electrophoresis under denaturing and non-denaturing conditions. Briefly, mutant and wild-type enzyme at 0.1 mg/ml were incubated at 37° C. for various time-points, cooled to 4° C., mixed with SDS-loading dye containing β-mercaptoethanol and run on 10% SDS-PAGE gels (denaturing conditions) or run on native 10% polyacrylamide gels (non-denaturing conditions) at 4° C. Gels were fixed with 10% methanol, 7% acetic acid for 30 minutes, and then stained with Sypro-Ruby protein gel stain (Molecular Probes, Invitrogen) for 3 hours. Protein staining was visualized under UV-light using an Alphalmager™ 3400 (Alpha Innotech). Finally, the exact melting temperature of both the wild-type and T172R muant were determined by circular dichroism using a JASCO-810 spectropolarimeter driven by a JASCO V500/FP-750 analysis program for Windows. The CD spectra were measured in millidegrees and normalized against PBS buffer.

Figure 5:
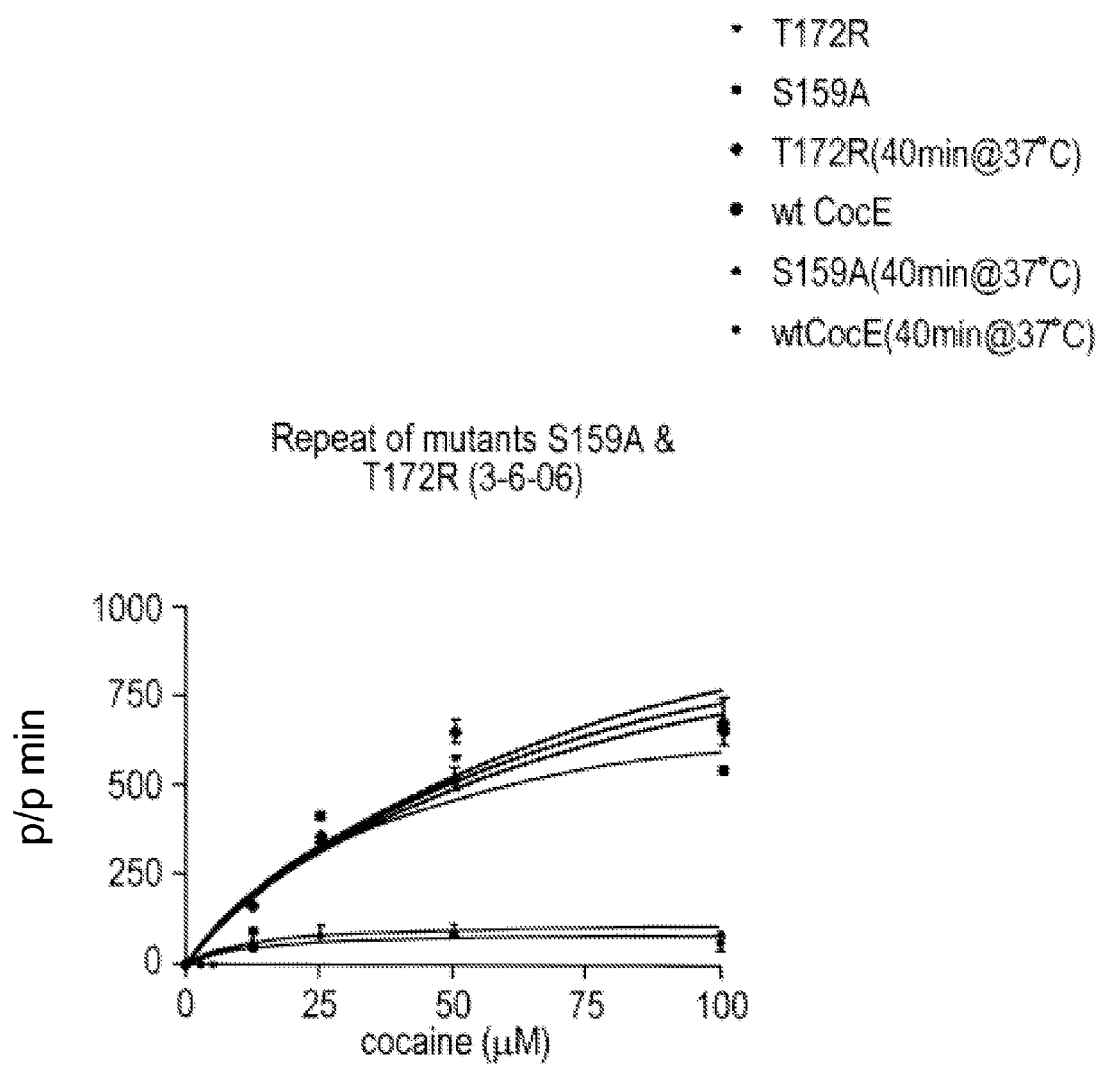
FIG. 5 is Michaelis-Menten enzyme kinetics plot for wild-type CocE, the T172R mutant CocE (SEQ ID NO: 26), and the S159A mutant CocE (SEQ ID NO: 11) for reactions carried out at 30° C. and 37° C. For further methodology information, see Example 4.

Results from the spectrophotometric assay showed that T172R had an increased Vmax and Km at room temperature and a greatly increased Vmax and Km at 37° C. as compared to wild-type CocE (see e.g., Table 3; FIG. 5). In fact, the T172R Vmax and Km at 37° C. was comparable to the Vmax and Km of wild-type CocE at room temperature. The S159A mutant CocE showed a slightly increased Vmax and Km at 37° C., but a decreased Vmax and Km at room temperature, as compared to wild-type CocE. Electrophoresis under denaturing conditions (FIG. 6a) indicated a single protein band for both the wild-type and T172R of approximately 65000 Da, regardless of incubation temperature, indicating the proteolytic degradation does not adequately describe the mechnanism for thermoinstability. The non-denaturing gels (FIG. 6b) showed a single protein band for the wild-type enzyme prior to incubation at 37° C., however upon incubation at 37° C., higher molecular weight species are seen to appear as the original band fades. These putative protein aggregates can also be observed for the T172R mutant, however the time to aggregation upon 37° C. incubation is longer, and in this procedure the T172R mutant was approximated to have a 8× longer half-life at 37° C. than the wildtype. Analysis of the protein melting temperature by circular dichrosim (FIG. 7) indicated temperature sensitive changes in protein tertiary structure were occurring in the near-UV range of the spectrum (between 260 nm and 320 nm). Curve-fitting of temperature-sensitive changes in this region of the spectrum indicated the wild-type CocE has a melting temperature of 36.15° C., with detectable denaturation beginning at approximately 30° C. The T172R mutant was determined to have a melting temperature of 41.43° C., with detectable denaturation beginning at approximately 28° C. Thus the single amino acid change from Tyrosine to Arginine at Amino acid 172, with an estimated 2.8 kCa/mol increase in thermostability, was determined to have a full 5 degrees increased melting temperature compared to the wild-type CocE.

TABLE 3

Kinetic parameters for T172R, S159A, and wt CocE.

| | S159A | S159A (40 min @ 37° C.) | T172R | T172R (40 min@ 37° C.) | wt CocE | wt CocE (40 min@ 37° C.) |
|---|---|---|---|---|---|---|
| Vmax | 876.6 | 130.7 | 1466 | 1267 | 1264 | 94.06 |
| Km | 43.65 | 15.69 | 88.20 | 78.80 | 71.81 | 12.30 |

Example 5

In Vivo Wild-Type CocE Prevention of Cocaine Lethality in Rats

To determine CocE's esteratic activity in vivo, a rodent model of acute cocaine toxicity was implemented. When treated with high doses of cocaine, rats first exhibit convulsions followed by cessation of respiration and movement. The lowest toxic dose of cocaine, when administered intraperitoneally, will produce fatality within 15 minutes of treatment.

Protection against cocaine-induced lethality by wild-type CocE was determined and compared to the protective effects of human BChE. The esteratic activity of CocE was established by assessing the activity of two mutant enzymes, each lacking one of three amino acids in the active site. Additionally, activity of a modified wild-type enzyme by a covalent modification of Ser17 within the active site, by phenylmethyl sulphonate fluoride (PMSF) was determined. Esteratic degradation of cocaine was shown to be the mechanism of CocE's protective effects by verifying if the enzyme protected against toxicity induced by WIN 35065-2 (Madras et al. (1989) J Pharmacol Exp Ther 251, 13-141), a cocaine analog which lacks the ester bridge at the proposed site of enzymatic hydrolysis.

Male Sprague-Dawley rats (300 grams) (Harlan Sprague Dawley, Indianapolis, Ind.) were housed three animals per cage. Following surgical implantation of a jugular catheter, all rats were individually housed until termination of the experiment. Rats were maintained on a 12-h light/dark cycle, with lights turned on at 7:30 a.m. and food and water were available ad libitum. After rats were anesthetized with ketamine hydrochloride (100 mg/kg, i.p.) and xylazine (10 mg/kg, i.p.), intravenous catheters (Micro-renethane tubing, 15 cm, MRE-040, Braintree Scientific Inc., Braintree, Mass.) were implanted into the right jugular vein. Approximately 3 cm of the catheter was inserted into the vein; the remaining tubing was passed subcutaneously to the back, where it exited from an incision made between the shoulder blades. The exposed tubing was capped with a 1 cm piece of stainless steel (0.28 diamter, Small Parts Inc., Miami, Fla.). Catheters were flushed daily with 0.5 ml of heparinized saline (50 U/ml) to maintain catheter patency. Following surgery, rats were allowed one week to recover. Each rat was used for a single experiment, and all experimental groups consisted of 6-8 rats.

To determine the lowest effective dose of CocE that blocked cocaine-induced convulsions and death, 0.1, 0.32, or 1.0 mg CocE or vehicle (phosphate buffered saline, PBS) was administered intravenously one minute after 180 mg/kg cocaine (i.p.). To determine the catalytic limits of CocE, increasing doses of cocaine were administered (100, 560, 1000 mg/kg, i.p.) one minute prior to 1.0 mg CocE (i.v.). Mutants and PMSF-blocked CocE were administered (1 mg, i.v.) one minute before 180 mg/kg cocaine (i.p.). CocE (1.0 mg, i.v.) was also administered one minute after the lowest dose of WIN-35065-2 (560 mg/kg, i.p.). CocE (1.0 mg, i.v.) was given before and after cocaine (100 mg/kg, i.p.) to determine the in vivo half-life of the esterase. All intravenous injections were followed by a heparinized saline flush (0.5 ml). After treatment, rats were observed for convulsion; and death. Number of convulsant episodes, duration of each episode, and type of convulsion were recorded. Death was defined as cessation of observed movement and respiration. Percent of animals in each experimental group exhibiting convulsions and lethality were calculated. Percent standard error mean was then calculated for each data point.

Figure 9:
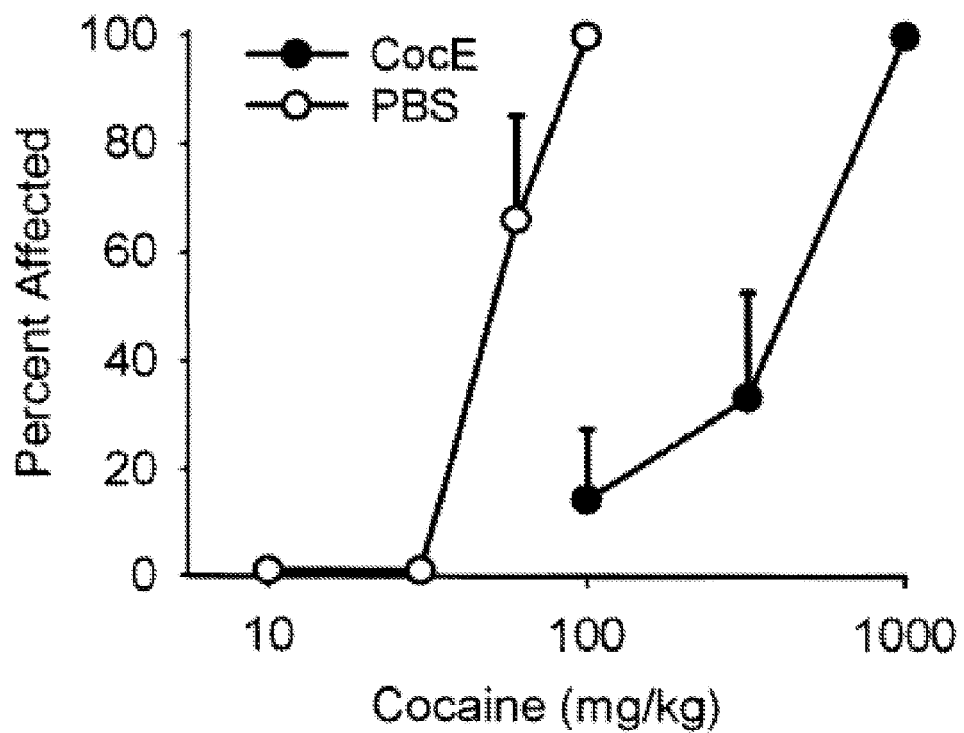
FIG. 9 is a line and scatter showing the effect of 1.0 mg CocE (closed circles) or PBS (vehicle, open circles) on cocaine-induced lethality when administered one minute after increasing doses of cocaine (n=6-7). Data presented are expressed as percent and its standard error. For further methodology information, see Example 5.

Results showed that, in the rodent model of acute toxicity, cocaine dose-dependently induced convulsions and death in rats; death was observed in less than 15 minutes after administration in 100% of animals given 100 mg/kg cocaine (see e.g., FIG. 9). CocE (1.0 mg) infused after cocaine administration produced a ten-fold shift in the cocaine-toxicity dose effect curve (see e.g., FIG. 9), such that 1000 mg/kg cocaine was required to surmount the protective, catalytic properties of CocE. This treatment regimen closely resembles human toxicity situations, where the antidote to overdose is given only after cocaine has been ingested, inhaled, or injected.

Wild-type CocE showed superior catalytic efficiency over human BChE. Given one minute before 180 mg/kg cocaine, 1 mg CocE offered 100% protection against cocaine-induced lethality (see e.g., FIG. 10), while a 10-times molar equivalent dose of human BChE (13 mg) offered no protection, similar to a ten-fold lower dose of CocE (0.1 mg) (see e.g., FIG. 10).

Figure 11:
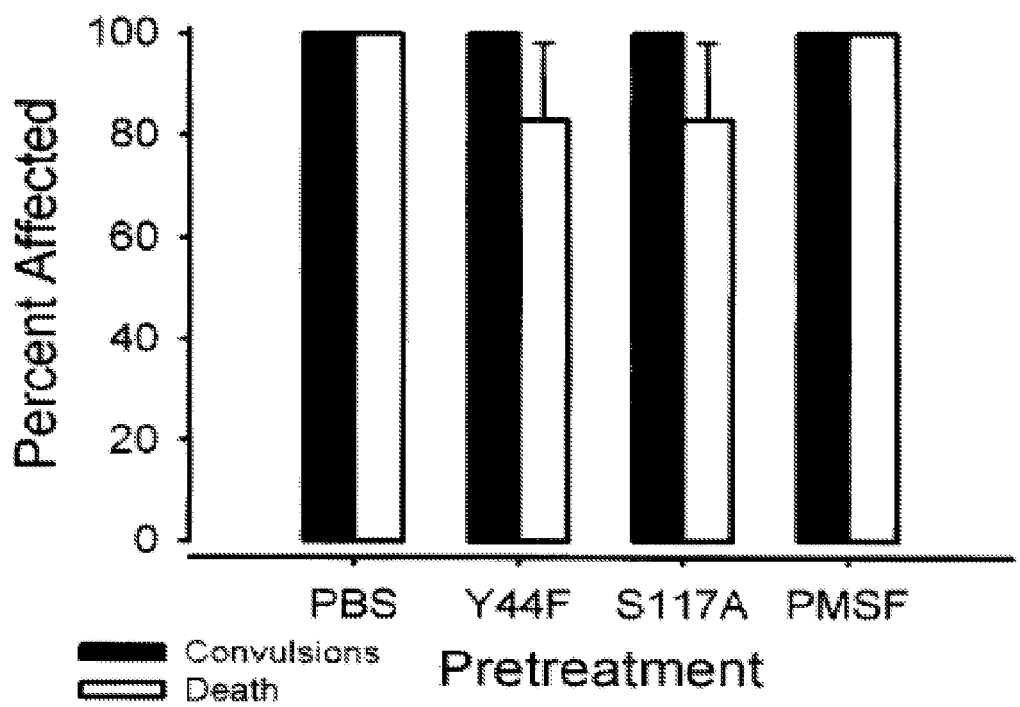
FIG. 11 is a bar graph showing the effect of CocE mutants S117A and Y44F, or PMSF treated CocE on cocaine-induced convulsions and lethality when administered 1 minute before 180 mg/kg cocaine (n=5-6). For further methodology information, see Example 5.
Figure 12:
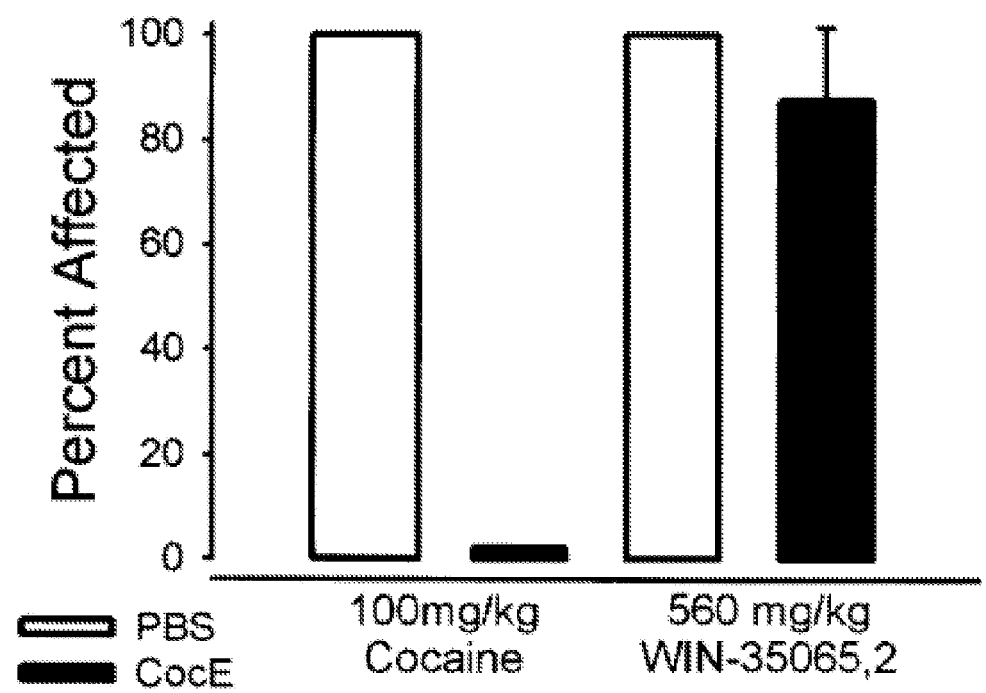
FIG. 12 is a bar graph showing the effect of 1.0 mg CocE or PBS administered one minute after the 560 mg/kg WIN-35065-2, the determined LD100 of the compound (n=6-8). For further methodology information, see Example 5.

Both mutations of CocE (Ser117Ala or Tyr44Phe) lacked in vivo activity and, therefore, had no protective effects (FIG. 11b). Furthermore, PMSF-treated enzyme also eliminated CocE's protective effect against cocaine (FIG. 11b). Additionally, the lethal effect of the nonhydrolyzable cocaine analog, WIN 35065-2, was not overcome by treatment with CocE (FIG. 12). Based upon in vivo protection studies performed with catalytically inactivated preparations of the enzyme (PMSF-treated and CocE inactive mutants), it is clear that the protective effects of the enzyme are due to its ability to hydrolyze cocaine. Taken together, these data comply with in vitro assessments of CocE's esteratic activity and confirm the enzyme's mechanism of protection against cocaine-induced lethality in vivo.

Example 6

Time-Dependent Effects of Wild-Type CocE

The effects of administering wild-type CocE prior to cocaine dosage was examine. The rat toxicity model was as described in Example 5. Wild-type CocE was administered 100, 30, 10, 3, and 1 minute before and 1 and 6 minutes after cocaine administration. Compound extractions from human plasma samples were performed in 100% acetonitrile (3× volume), incubated for approximately 15 min, centrifuged at 13,000 rpm for 4.5 min, and the resulting supernatant was collected. The extracts were concentrated on a Savant Speed Vac (ThermoElectron Corp., Franklin, Mass.) to remove the acetonitrile. Extracted samples were reconstituted in water and further diluted 10-1000 times.

Human plasma samples were spiked with 300 µM cocaine and maintained at 37° C. One aliquot of plasma was sampled prior to the addition of cocaine esterase or esterase vehicle, and another aliquots was collected 1 min following esterase administration. Plasma aliquots were mixed immediately with the internal standard (cocaine-$D_3$) and a saturated sodium fluoride solution to prevent further cocaine metabolism. Tissue extractions were performed and levels of cocaine and internal standard were quantified by HPLC with tandem mass spectrometry.

For time-dependent inactivation of CocE in vitro, purified CocE enzyme (at 250 ng/ml) was incubated in assay buffer in the absence of cocaine at 37° C. for various times. Following incubation at 37° C. the samples were placed on ice. To assess the effect of temperature on CocE activity, samples were incubated with (−) cocaine at various concentrations as indicated at a final enzyme concentration of 125 ng/ml. The rate of decay of (−)-cocaine at A240 was measured on a multiplate reader. The data were fitted to a single exponential decay using Kaleidagraph™ (Synergy software) yielding a $t_{1/2}$ of 13.2.

Figure 13:
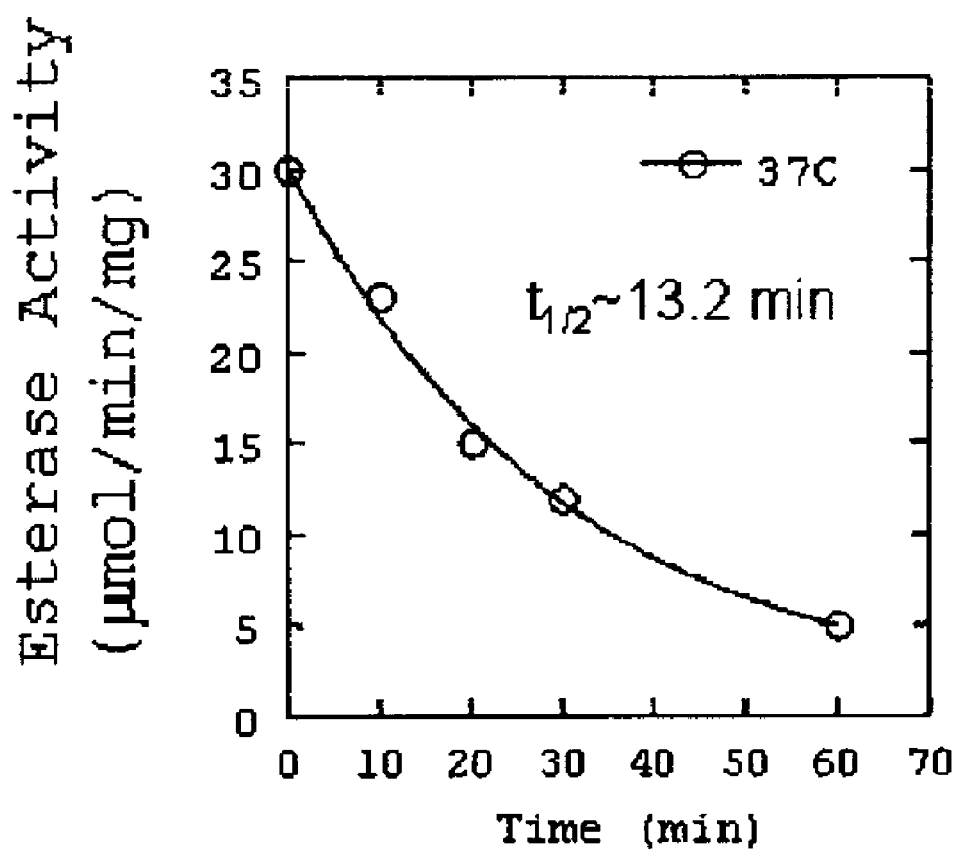
FIG. 13 is a line and scatter plot showing time-dependent inactivation of CocE (125 ng/ml) in vitro. Exponential decay $t_{1/2}$ was calculated as 13.2. For further methodology information, see Example 6.
Figure 14:
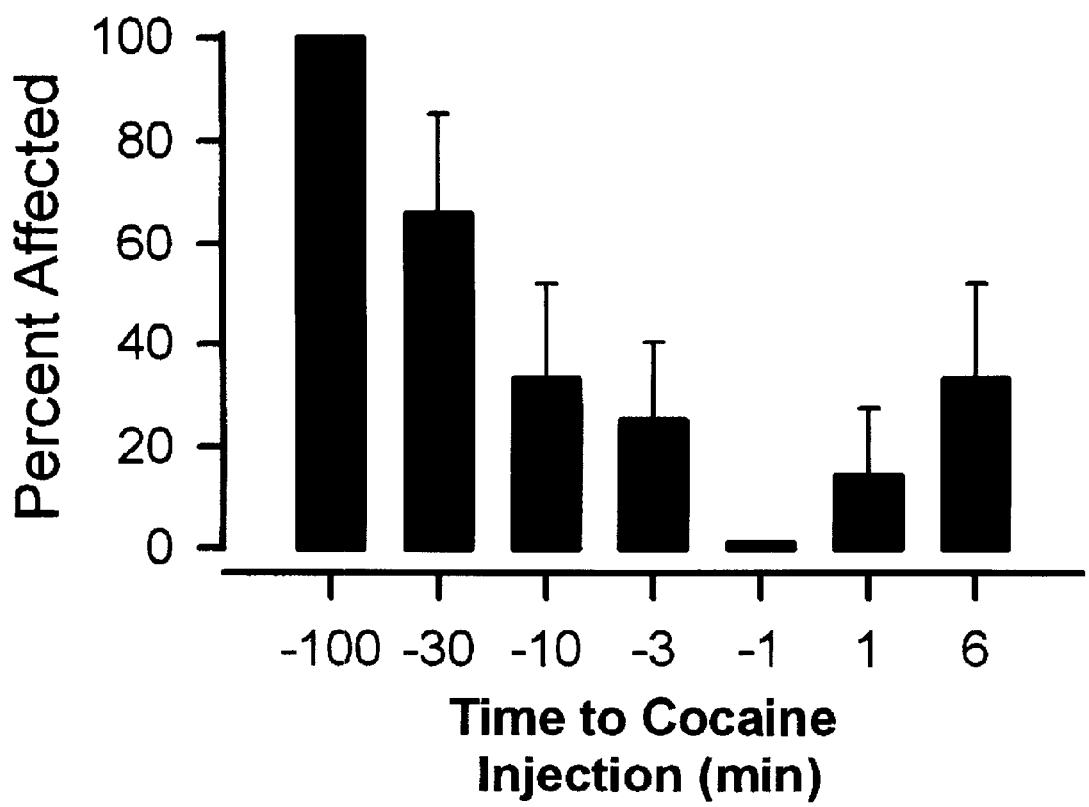
FIG. 14 is a bar graph showing time-dependent protective effects of 1 mg CocE when administered at various times before and after 100 mg/kg cocaine (n=6-8). For further methodology information, see Example 6.

Wild-type CocE was found to have time-dependent protective effects; 100% of rats were saved when treated with CocE (1 mg) 1 minute before cocaine, while only 66% and 32% of rats survived when treated with CocE 30 and 1 minutes before cocaine, respectively (see e.g., FIG. 14). CocE's protective effects were eliminated when rats were treated 100 min prior to cocaine. This time-dependent effect is most likely due to the thermal deactivation of the enzyme in vivo. In rat plasma, CocE was found to have a remarkably short half-life (about 10 minutes, FIG. 13), most likely due to sensitivity to changes in pH and temperature. Additionally, preliminary in vitro data with the purified enzyme suggests that CocE undergoes a temperature-dependent inactivation with a $t_{1/2}$ of approximately 15 min at 37° C.

Given these data, it can be approximated that a 1 mg of CocE dose administered 30 minutes prior to cocaine, will decay approximately 3 half-lives, leaving 0.25 mg of wild-type enzyme in the general circulation when cocaine is administered.

Figure 10:
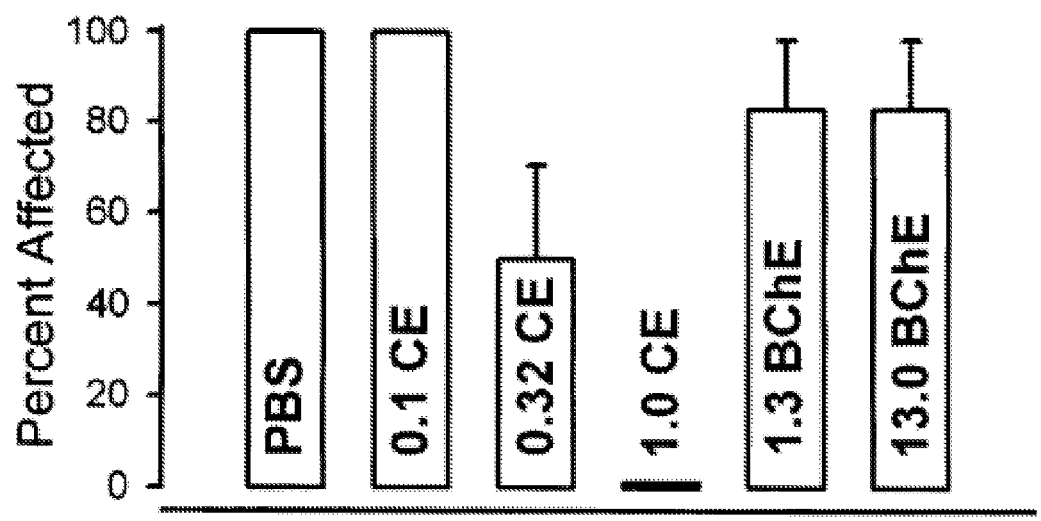
FIG. 10 is a bar graph showing the effect of increasing doses of CocE (CE) or human BChE (BChE), or PBS, on cocaine-induced lethality when administered one minute before 180 mg/kg cocaine (n=6-7). Data presented are expressed as percent and its standard error mean. For further methodology information, see Example 5.

Previous studies have suggested that lethal blood concentrations of cocaine in the rat vary between 50-128 µM (Mets B and Virag L (1995) Anesth Analg 81, 1033-1038; Mets et al. (1999) Life Sci 65, 1317-1328), and peak plasma levels of cocaine occur about 13 minutes after an intraperitoneal injection (Sun et al. (2002) J Pharmacol Exp Ther 302, 710-716). Based on reported kinetics of intraperitoneal cocaine administration (Sun et al. (2002) J Pharmacol Exp Ther 302, 710-716), it is estimated that 100 and 320 mg/kg cocaine yield peak cocaine blood concentration of 35 µM and 113 µM, respectively. Lethal concentrations of cocaine are of a similar magnitude in humans (20-200 µM) (Finkle B S and McCloskey K L (1978) J Forensic Sci 23, 173-189; Wetli and Wright (1979) J Am Med Assoc 241, 2519-2522). As 1 mg of wild-type CocE saved rats treated with these doses of cocaine (FIG. 9), it can be justifiably predicted that the enzyme would protect against cocaine-toxicity in the human. Furthermore, cocaine levels measured using high performance liquid chromatography tandem mass spectrometry in human plasma spiked with 300 µM cocaine, a concentration that exceeds reported toxic levels of cocaine, and then treated with CocE (a molar equivalent of our in vivo 1.0 mg dose), reduced the cocaine concentration to approximately 2 µM in less than a minute (FIG. 10).

Protection against an LD50 dose of cocaine in rats requires a 10 mg/kg treatment of BChE (Lynch et al. (1997) Toxicol Appl Pharmacol 145, 363-371), assuming that the enzyme is distributed similarly in the human, a 70 kg individual would require a 700 mg dose of exogenous BChE to protect against an overdose. Furthermore, there is no evidence that BChE can act to reverse cocaine-toxicity when administered after cocaine, a necessary characteristic of an antidote for cocaine toxicity.

Figure 15:
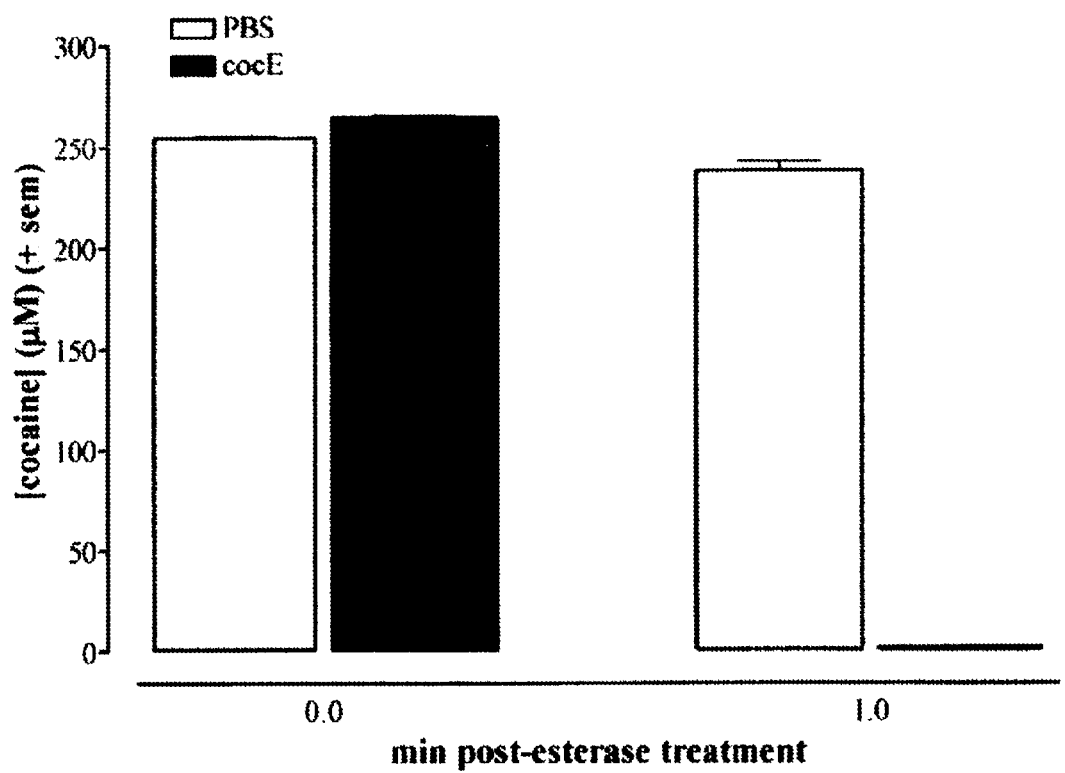
FIG. 15 is a bar graph showing the cocaine concentrations in human plasma treated with 0.8 µM cocaine esterase or esterase vehicle at zero and one minute following esterase administration. For further methodology information, see Example 6.

It is thus demonstrated that a dose of 1 mg wild-type CocE in a 300 gram rat is sufficient to protect against a dose of cocaine that exceeds the LD100 (FIG. 9). Additionally, the enzyme given both before, and more importantly, up to 6 minutes after the LD100 dose of cocaine, provided protection from toxicity (FIG. 14). CocE metabolized cocaine concentrations in serum by 150-fold in less than one minute (FIG. 15).

Given these data, it is predicted that a 250 mg of CocE administered to a 70 kg human after toxic cocaine ingestion would rescue the individual from certain death. The above demonstrates that wild-type CocE is an efficient anti-cocaine molecule but that the short activity time of the enzyme under physiological conditions limits it therapeutic value. Such results point to the importance of extending the thermostability of the wild-type CocE.

Example 7

In Vivo T172R Mutant CocE Prevention of Cocaine Lethality in Rats

The hydrolytic activity of wild-type CocE and T172R mutant CocE was characterized and confirmed in vivo by assessing its ability to prevent cocaine-induced lethality in rats.

Animal treatment was as described in Example 5. Increasing doses of cocaine were administered (i.p.) to rats, and one minute after, wild-type CocE (0.32 mg), mutant CocE T172R (0.32 mg), or vehicle was administered intravenously. All intravenous injections were followed by a heparinized flush (0.5 ml). After treatment, rats were observed for death. Time until death was recorded for the 1 g/kg cocaine dosage. Wild-type and T172R CocE (0.32 mg) was administered at various times preceding (1, 10, 30, and 60 minutes) administration of 320 mg/kp i.p. of cocaine, with rats then monitored for death.

Figure 16:
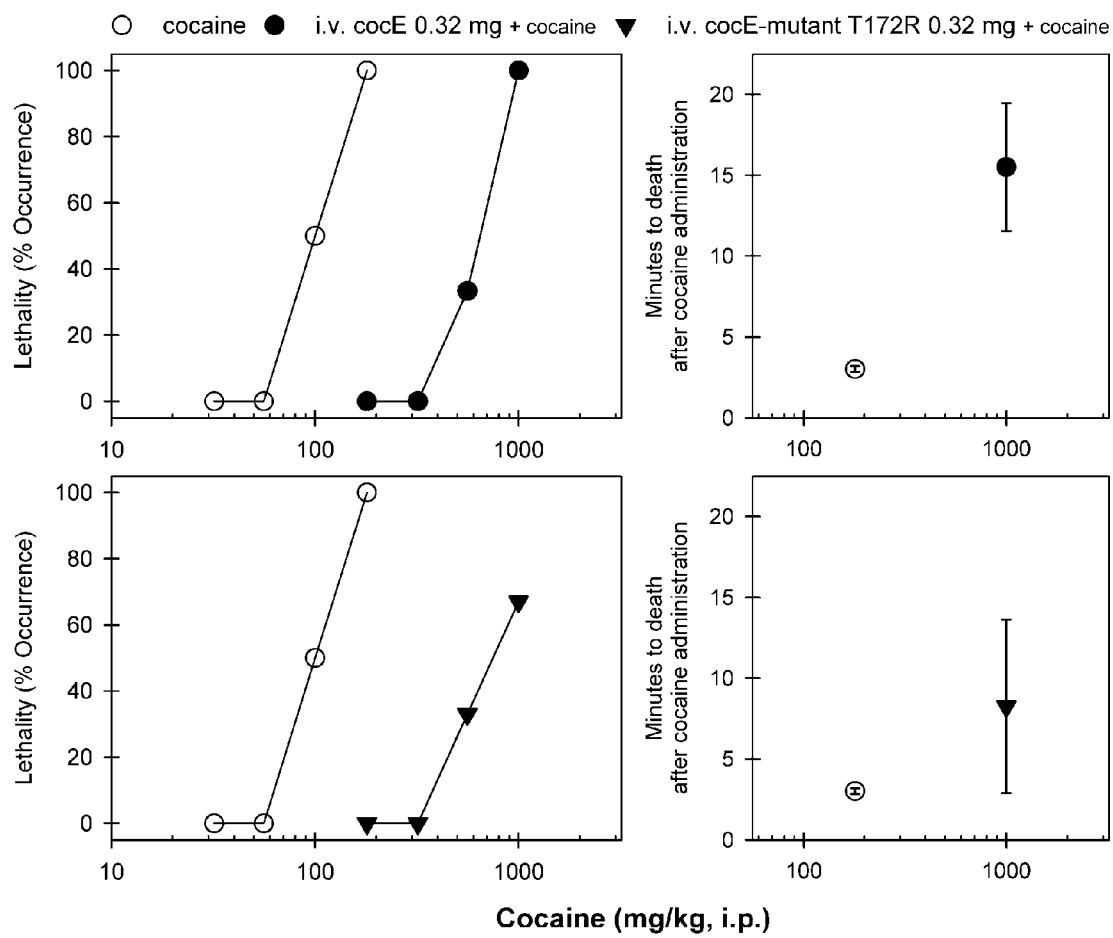
FIG. 16 is a series of line and scatter plots showing the effect of 0.32 mg CocE (closed circles), 0.32 mg of T172R mutant CocE (close triangles), or PBS (vehicle, open circles) on cocaine-induced lethality when administered one minute after increasing doses of cocaine (left panel) and minutes to death after cocaine administration (right panel). For further methodology information, see Example 7.
Figure 17:
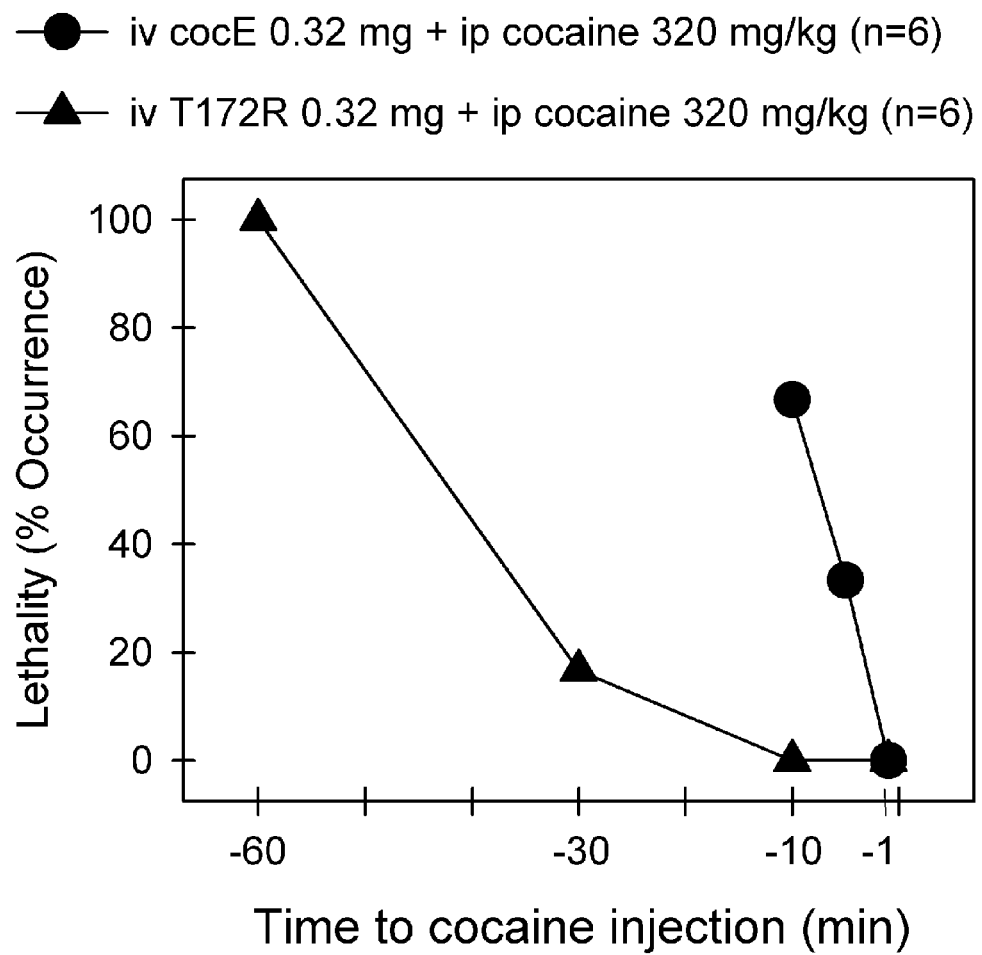
FIG. 17 is a line and scatter plot showing the effect of 0.32 mg/kg of CocE (closed circles) or T172R mutant CocE (closed triangles) on cocaine-induced lethality when administered at 1, 10, 30, and 60 minutes before administration of 320 mg/kg cocaine (n=6). For further methodology information, see Example 7.

Results demonstrate the ability of intravenous CocE and, especially, mutant CocE to reverse or prevent the lethal effects produced by cocaine. Wild-type CocE administered one minute after cocaine administration prevented lethality at cocaine dosages that killed control rats and 100% lethality did not occur until cocaine dosages of 1 g/kg (see e.g., FIG. 16). The T172R mutant CocE treated rats were able to tolerate even higher dosages, with the 1 g/kg of cocaine resulting in only about 70% lethality. And the prophylactic effects of T172R mutant CocE was longer lasting than the wild-type CocE (see e.g., FIG. 17).

Example 8

In Vivo Repeated CocE Dose in Mice

Additional studies were done on the effect of CocE on toxicity in the mouse, particularly with respect to repeated doses.

The animal toxicity model was similar to that described previously, except as described. Male NIH Swiss mice were used. For tail intravenous injection, mice are placed in a small restraint chamber that exposes their tail. A heat lamp with an infrared, 250 w bulb is placed about 4 inches from the tail, and left for a couple of minutes. The tail is then cleansed with an alcohol wipe and a 30 G ½ precision glide needle (Fisher Scientific), is inserted into one of the side veins for infusion. To verify whether the needle is in the vein a small amount of drug is infused, if in the correct location the solution should infuse easily without any indication of an incorrect subcutaneous location, which appears white at the site of injection. For intravenous catheterization, Male NIH Swiss mice are anesthetized with ketamine 100 mg/kg and xylazine 10 mg/kg co-administered i.p. When mice are no longer responsive to paw pressure, the neck is shaved and prepped by alternating Betadine and alcohol wipes. Under clean conditions, a right transverse neck incision is made and the external jugular vein is isolated. A catheter is inserted into the vein with the aid of a dissecting microscope to the level of the right atrium, and is secured in the vein with nylon, 4-0 sutures and tissue adhesive, 3M Vetbond (3M Animal Care Products, St. Paul, Minn.). The catheters are a short length of Tygon tubing with an inner diameter of 0.010 in. and an outer diameter of 0.030 in. (Small Parts, Inc., Miami Lakes, Fla.). A small incision is made in the middle of the animal's back, and a trocar inserted subcutaneously to exit at the ventral incision site. The catheter is then pulled through the trocar and brought out the animal's back where it is held in place with nylon suture material and the tissue adhesive. A short piece of steel wire with a diameter of 0.011 in. (Small Parts, Inc., Miami Lakes, Fla.) is inserted into the end of the catheter. The ventral incision is closed with 4-0 Vicryl suture material and the mouse placed under a heat lamp for recovery. Approximately an hour later, the mouse is returned to its home cage.

Mice that survived a first administration of the combination of 0.32 mg CocE and 320 mg/kg cocaine were given this combination again, 14 days following the initial administration. All of the mice survived this second administration. All mice also survived a third administration 21 days following the first dose combination. The effectiveness of repeated administration suggests that a strong immune response is not being mounted to CocE in this preparation, perhaps because of its rapid clearance.

Figure 18:
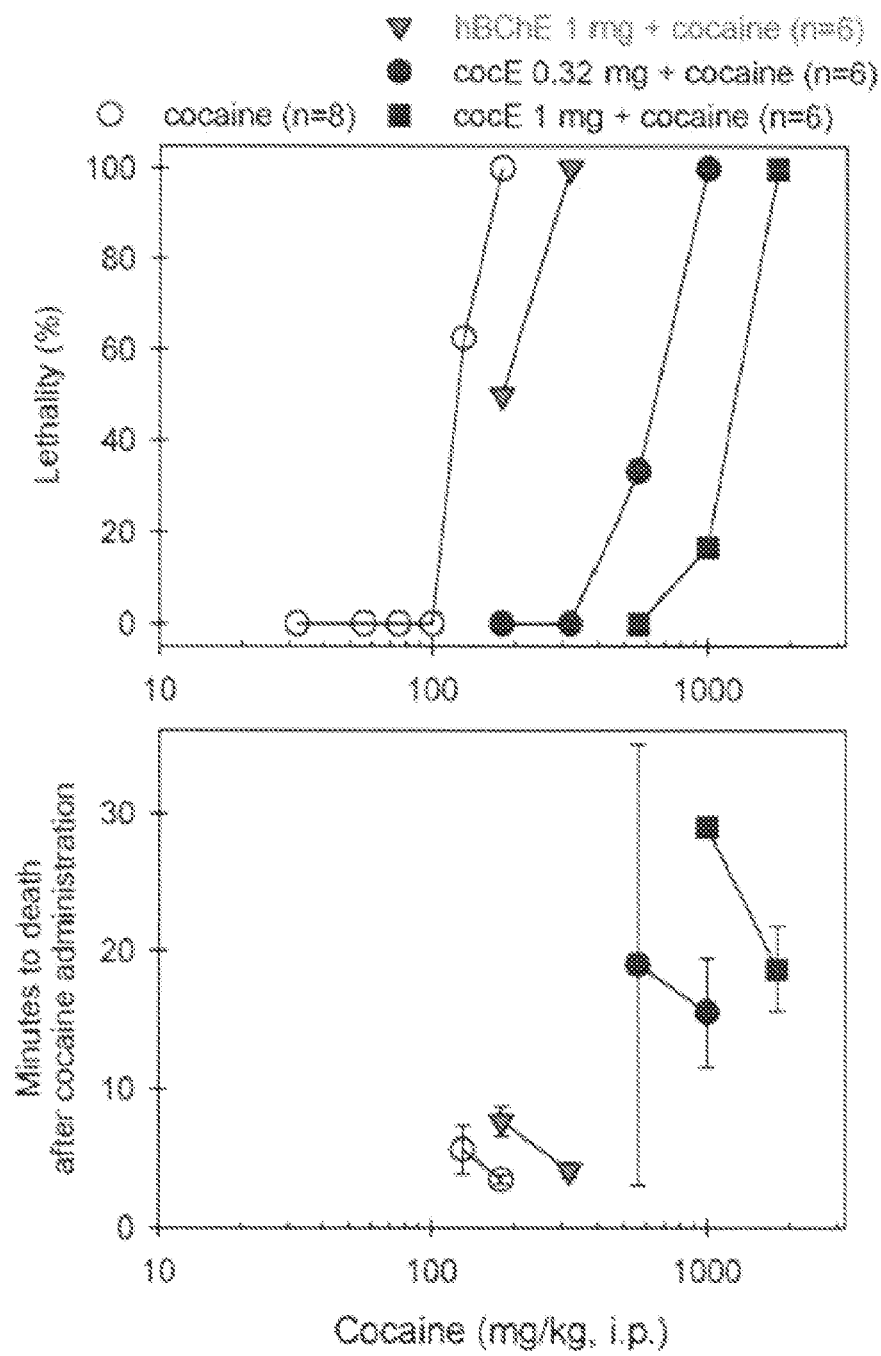
FIG. 18 is a series of line and scatter plots showing the effect of 1 mg of hBChE (closed triangle), 0.32 mg CocE (closed circle), or 1 mg of CocE (closed square) on cocaine-induced lethality.

Results showed that a dramatic shift to the right in the potency of cocaine in producing death was afforded by both 0.32 and 1.0 mg/kg cocaine (see e.g., FIG. 18). The latency to death was markedly extended by CocE: following 180 mg/kg i.p. cocaine, mice typically died in about 3 min. After a dose of 1.0 gm/kg cocaine plus 1.0 mg of CocE, death occurred at 28 minutes on average. Data was also examined for the ability of hBChE to block the toxicity of cocaine. At a dose of 1 mg, hBChE produced a slight increase in the dose of cocaine necessary to kill the mice (see e.g., FIG. 18). This enzyme is markedly less effective than CocE. Although larger doses of cocaine were necessary to kill the mice following administration of hBChE, the time to death was not modified by this enzyme.

Example 9

In Vivo Half-Life and Biodistribution Tests

The in vivo half-life and biodistribution of the mutant CocE polypeptides are examined in BALB/c mice. In brief, $^{125}$I is labeled to the tyrosine residues of mutant CocE by using the well-established chloramine-T iodination method (Hunter, W M and Greenwood, F C (1962) Nature 194, 495-496). BALB/c mice are injected via their tail veins with 0.1 mL of either 0.5 μCi $^{125}$I-labeled mutant CocE or the mutant CocE-PEG conjugates. Each experimental group consists of 24 mice. Three mice are sacrificed by cervical dislocation at the 15-, 30-, 90-minute, 3-, 12-, 24-, 48-, and 72-hour time intervals following the drug injection. Blood samples as well as tissue samples of liver, lung, heart, kidney, and spleen are collected, weighed, and measured for radioactivity using a gamma counter. The blood samples are also centrifuged, and the supernatants will be collected and counted for estimation of plasma-associated radiolabels. The ratio of the peak to that of the internal standard is used as the assay parameter. PK parameters are calculated by using the KINFT (Kaltenbach, M L and Vistelle, R (1994) Anticancer Research 14, 2375-2377) nonlinear least-squares computer program by fitting the plasma radioactivity data to a biexponential equation (Gibaldi, M. and Perrier, D. (1982) Pharmacokinetics):

$$A(t)=A_1 e^{-k_1 t}+A_2 e^{-k_2 t}$$

Where A(t)=% ID/mL plasma and ID=injected dose. $k_2$ will be used to calculate the first-order elimination time $t_{1/2}$. The area under the curve (AUC) of the plasma concentration-time curve, the steady-state volume of distribution (Vss), total plasma clearance (Cl), and the mean residence time (MRT) are calculated from $A_1, A_2, k_1, k_2$, and the body weight (kg) of the mouse as described by Gibaldi and Perrier, 1982). The organ permeability-surface area (PS) product is calculated as:

$$PS=[V_d-V_o]Cp_{(60\ min)}/AUC_{(0-60\ min)}$$

Where $CP_{(60\ min)}$ is the terminal plasma concentration (dpm/µL) at 60 min after injection, $V_d$ is the tissue volume of distribution determined from the ratio of disintegrations per minute per gram of tissue to $Cp_{(60\ min)}$, and $V_o$ is the organ plasma volume. The organ delivery of the samples is determined as:

$$\%\ ID/g=PS \times AUC_{(0-60\ min)}$$

Where % ID/g is the percent injected dose taken up by gram of organ.

Example 10

Immunology

CocE can be used in incomplete Freund's adjuvant (IFA) to immunize mice (see Table 4). A direct ELISA specific for CocE antibodies was set up by a standard protocol. CocE was used (1 ug/ml) to coat a 96-well micro-titer plate using a borate buffered saline (1.5 M NaCl, 0.5 M H3BO3, 1.0 M NaOH) to resuspend the cocaine esterase (50 uL/well). The coating plates was left overnight at 4 C. The coating buffer was removed the following morning and the plates blocked with 2% normal goat serum in PBS for 1 hr at 37 C and washed 3 times. Serum from the various groups of mice was serially diluted in 50 µL of PBS in the wells in a range of $10^2$ to 10' and run in duplicate. The plates were covered and incubated for 30 minutes at 37 C. Subsequently, the plates were washed 3 times and 50 µL/well of Goat anti-mouse IgG peroxidase labeled antibody diluted 1:400. The plates were then washed 3 times and 100 µL peroxidase substrate solution (OPD dissolved in citratelphosphate buffer) was added to each well. After a 5-10 minute incubation (based upon color development in the positive controls) the reaction was stopped using 3M H2SO4 (50 µL/well). The plates were read at 490 nm and titer determined by the highest dilution that showed increases over background absorbance. Positive controls were derived by immunizing Balb/c mice with 100 µg in 100 µL of Cocaine esterase emulsified in incomplete Freund's adjuvant (IPA) by intraperitoneal (IP) injection. In Positive 1 group the serum was isolated from 2 week immunized mice. In Positive 2 group immunized mice were boosted using 100 µg in 100 µL by IP injection at 2 weeks post-primary immunization and the serum collected after an additional week (3 week post-primary).

High titers were derived from the two positive control groups immunized with CocE, $10^5$ and $10^6$, respectively. The antibody titers from animals given CocE i.v. during cocaine challenges demonstrated detectable but relatively low titers compared to the positive control animals immunized by CocE plus IFA. Serum collected from animals immunized once with CocE/IFA demonstrated high titer of $10^5$, while serum from animals given an additional boost were had a higher titer of $10^6$ (3 mice/group). The serum collected from these animals will serve as positive controls for all subsequent titering experiments.

TABLE 4

CocE titers of immunized mice

| Group | Protocol | Titer (log10 dilution +/− SE) |
|---|---|---|
| Positive 1 (n = 3) 2 weeks | Immunized (IFA/IP) | 5 |
| Positive 2 (n = 3) 3 weeks | Immunized/Boost (IFA/IP) | 6 |
| Challenged and Treated (3×) | CocE given with cocaine | 3.33 +/− 0.333 |
| Challenged and Treated (4×) | CocE given with cocaine | 3.5 +/− 0.5 |

Example 11

CocE Pegylation

Conjugation of one to two PEG polymers per enzyme molecule is generally sufficient to yield the desired protective effects (Avramis et al. (2002) Blood 99, 1986-1994). Because each wild type CocE molecule is reported to contain 8 lysine residues, with none in the active site but only 2 being close to the active site (Turner et al. (2002) Biochemistry 41, 12297-12307), targeting lysine for pegylation is unlikely to inactivate the enzyme. The mutant CocE is mixed with various monomethoxy-PEG (m-PEG) polymers (MW ranging from 3-12 KDa); all contain an activated N-end functional hydroxysucciniyl ester group (mPEG-NHS; from Shear Water Inc., Birmingham, Ala.). PEG with a molecular weight of 5.5 KDa will be first attempted, because the inventors' results and those of other investigators (see e.g., Veronese, F M and Harris, J M (2002) Advanced Drug Delivery Reviews 54, 453-456; Avramis et al. (2002) Blood 99, 1986-1994) demonstrated that this molecular weight yields the beneficial protection. Different molar ratios of $[NH_2]:[mPEG]$ (the former is calculated based on the total moles of lysine residues of mutant CocE) ranging from 1:2 to 1:10 are tested to obtain optimal conditions. Conjugation proceeds for about 40 minutes at 4° C. with gentle agitation. The reaction products are then purified by ultrafiltration (MWCO 10,000) at 4° C. Activities of the pegylated mutant CecE products are determined by measuring the initial rates of cocaine hydrolysis using the previously established procedure (Turner et al. (2002) Biochemistry 41, 12297-12307). In addition, MALDi-TOF mass spectraphotometry is performed on these products to analyze the degree of pegylation and their molecular weight. The pegylated products are stored at −40° C. and thawed immediately prior to their uses.

Standard characterization, including determination of the optimal pH, temperature, ionic strength, as well as kinetic parameters (e.g. Km, Vm), of the mutant CocE-PEG conjugates are conducted in PBS. Furthermore, thermal stability of the pegylated products and their stability against proteolytic degradation are examined in the presence of human plasma or blood. In vivo functional tests of the mutant CocE-PEG products are conducted as described above. The in vivo half-life and biodistribution of the mutant CocE-PEG conjugates, as compared to free CocE are conducted as described above (see Example 9).

Statistical analysis is performed on the results obtained from the pegylation experiments. Random block two-way ANOVA with Dennett's post-test is performed on data sets with two variables using GraphPad (San Diego, Calif.) Prism for Windows and GraphPad Software. Paired t-test is performed for experiments with two conditions.

Conjugation of mutant CocE to high molecular weight (e.g., up to 60 KDa) branched PEG can also be performed (see e.g., Reddy et al. (2002) Advanced Drug Delivery Reviews 54, 571-586).

Additionally, site specific PEGylation can be a viable alternative to reduce functional and structural heterogeneity. The removal of cysteine residues near the active site or incorporation of cysteine residues on the protein surface can serve as better PEGylation substrates (through maleimide coupling). Similarly, amine-coupling of PEG to CocE can be employed through, for example, the conservative substitution of arginine residues for any of mutant CocE's (nine lysines total in wild-type CocE, seven of which are surface lysines).

Figure 19:
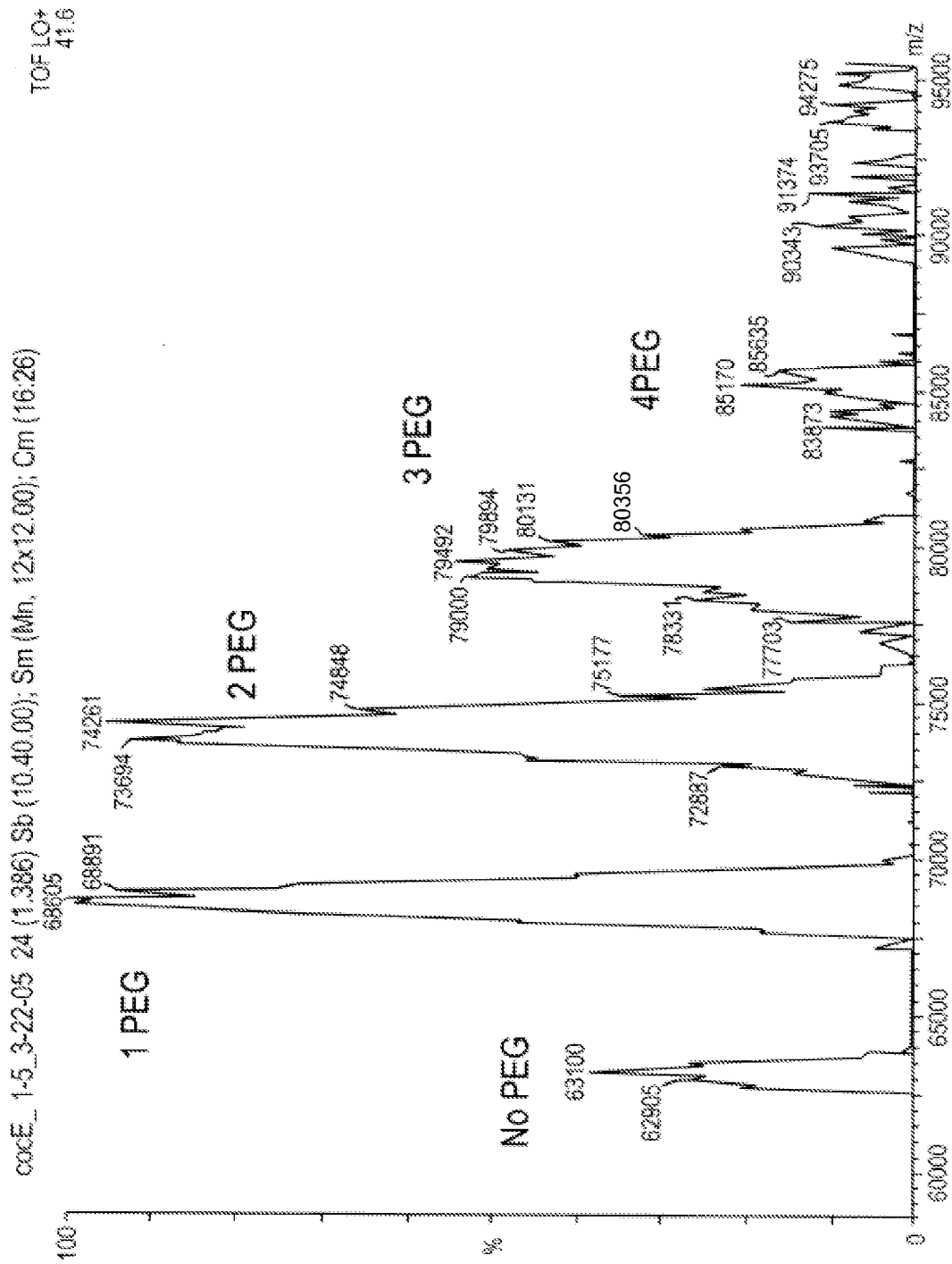
FIG. 19 is a trace of the MALDI-TOF mass spectrum of pegylated CocE. Mass difference between peaks corresponds to ~5500 Da; equivalent to the molecular weight of a single PEG chain. For further methodology information, see Example 11.

Preliminary findings have shown that wild-type (WT) CocE was successfully linked with monomethoxy-PEG (m-PEG) polymars (MW: 5.5 KDa) containing an activated succinimidyl functional group at one end, using the procedures described above. A high yield of the initial CocE activity (>70%) was recovered after the pegylation reaction. MALDI-TOF mass spectra revealed four primary peaks for the PEG-CocE products, indicating the presence of a heterogeneous mixture of the conjugates containing different numbers of the PEG chains (ranging from 1 to 4, respectively) (see e.g., FIG. 19). It has been suggested in the literature that conjugation of merely 1-2 PEG chains per protein molecule would be able to yield PEG-induced protective effects (Veronese, F M and Harris, J M (2002b) Advanced Drug Delivery Reviews 54, 457-606; Avramis et al (2002) Blood 99, 1986-1994). To this regard, the pegylation method employed here apparently satisfies such a requirement.

Example 12

RBC Encapsulation

RBC encapsulation of CocE can be accomplished via a linked PTD peptide. LMWP is selected as the PTD peptide to ferry mutant CocE into RBC, because of its potency in translocating proteins across cell membrane (Park et al. (2005) FASEB Journal, in press) and its lack of toxicity (Chang et al. (2001) AAPS Journal 3, Article #17, #18 and #19). To ensure that the encapsulated mutant CocE is permanently embedded in RBC, the linkage between CocE and LMWP can degrade automatically and rapidly once the mutant CocE-LMWP conjugates enter RBC. A linker such as a disulfide (S—S) bond that will be degraded quickly inside the RBC due to the presence of elevated cytosolic glutathione and reductase activity (Trouet et al. (1982) Proceeding of the National Academy of Science 79, 626-629), ensures that CocE will stay in the RBC.

To produce mutant CocE-LMWP conjugates linked with S—S bonds, the amine group at the N-end of LMWP (this is the only —NH$_2$ group on LMWP) is first activated with SPDP, and the activated LMWP then mixed with mutant CocE in the presence of dithiothretol (DTT) to allow for the formation of the S—S bond with one of the (four in wild-type) free cysteine residues on mutant CocE (Turner et al. (2002) Biochemistry 41, 12297-12307); according to a modified procedure previously developed (Liang et al. (2000) AAPS Pharmaceutical Science 2, Article 7). CocE is stable when being stored in DTT (Turner et al. (2002) Biochemistry 41, 12297-12307), suggesting that use of these free cysteine groups for conjugation is not likely to impair the catalytic activity of this enzyme (already performed mutation of each cysteine in wild-type CocE to a serine resulted in no diminution of activity). The final LWMP-CocE products is then purified via a heparin column, and is stored by lyophilization.

Encapsulation is achieved by incubating RBC with mutant CocE-LMWP for 30-60 minutes. Because PTD-mediated cell entry is temperature-independent (Schwarze et al. (1999) Science 285, 1569-1572), encapsulation is conducted at 4° C. to maximally preserve the functionality of RBC. The process and extent of mutant CocE entrapment in RBC is monitored by confocal microscopy and flow cytometry analysis using FITC-labeled mutant CocE. The morphology of mutant CocE-entrapped RBC is also be examined by SEM.

Basic characterization—including assessment of the functionality of both RBC (e.g. oxygen-transfer activity) and mutant CocE (e.g. cocaine-hydrolyzing activity, kinetic properties such as Km, Vm, etc.), leakage of mutant CocE from RBC (i.e. by incubating mutant CocE-loaded RBC in buffer and then measuring enzyme activity in the supernatant), and stability of the entrapped mutant CocE against proteolytic degradation—is conducted either in buffer or in plasma. Results obtained for the RBC-encapsulated mutant CocE are compared with those obtained for the free enzyme. In vivo functional tests of the mutant CocE-encapsulated RBC are conducted as described above.

Human RBC (from American Red Cross, Detroit, Mich.) are used for in vitro studies. For in vivo animal studies including the functional tests and pharmacokinetic studies, however, autologous RBC from the same animal species are be used to avoid cell incompatibility and possible toxic effects.

Circulation half-life ($t_{1/2}$) of mutant CocE-entrapped RBC is determined by injecting $^{125}$I-labeled mutant CocE (i.e. prior to its loading into RBC) into mice, according to the same procedures described above. Each set of experiments consists of 24 mice. Mice (3) are sacrificed at 3-, 6-, 12-, 24-hour and 3-, 6-, 10-, and 15-day time intervals. Blood and tissue samples are collected, weighed, and measured for radioactivity. PK parameters including the elimination $t_{1/2}$, as well as tissue distribution are calculated by using the KINFT program as described above. Pharmacokinetic results obtained for the RBC-encapsulated mutant CocE are compared with those obtained for free mutant CocE.

Statistical analysis is performed on the results obtained from the RBC encapsulation experiments. Random block two-way ANOVA with Dennett's post-test is performed on data sets with two variables using GraphPad (San Diego, Calif.) Prism for Windows and GraphPad Software. Paired t-test is performed for experiments with two conditions.

To examine if the previously suggested could fulfill the latter two requirements, preliminary studies of PTD-mediated RBC encapsulation were conducted using L-asparaginase as a model enzyme. LMWVP, a PTD peptide previously developed in Dr. Yang's laboratory (Chang et al. (2001) AAPS Journal 3, Article #17, #1, and #19) with proven, potent membrane-penetrating activity (Park et al. (2005) FASEB Journal, in press), was linked to asparaginase using a procedure similar to that described above. The LMWP-ASNase conjugates were then incubated with RBC (collected from DBA/2 mice) for 2 hrs at 4° C. For comparison, RBC-Ghosts containing encapsulated ASNase were also prepared according to the previously established procedures (Updike et al. (1976) Science 193, 681-683). Preliminary results demonstrated that loading efficiency of the LMWP-mediated method was at least comparable to, if not better than, the conventional, osmosis-based cell rupturing technique. A major advantage of the PTD-mediated method, however, is that it only requires a single step for processing; unlike the other cell entry methods that all require multiple steps of the loading and washing procedures.

Figure 20:
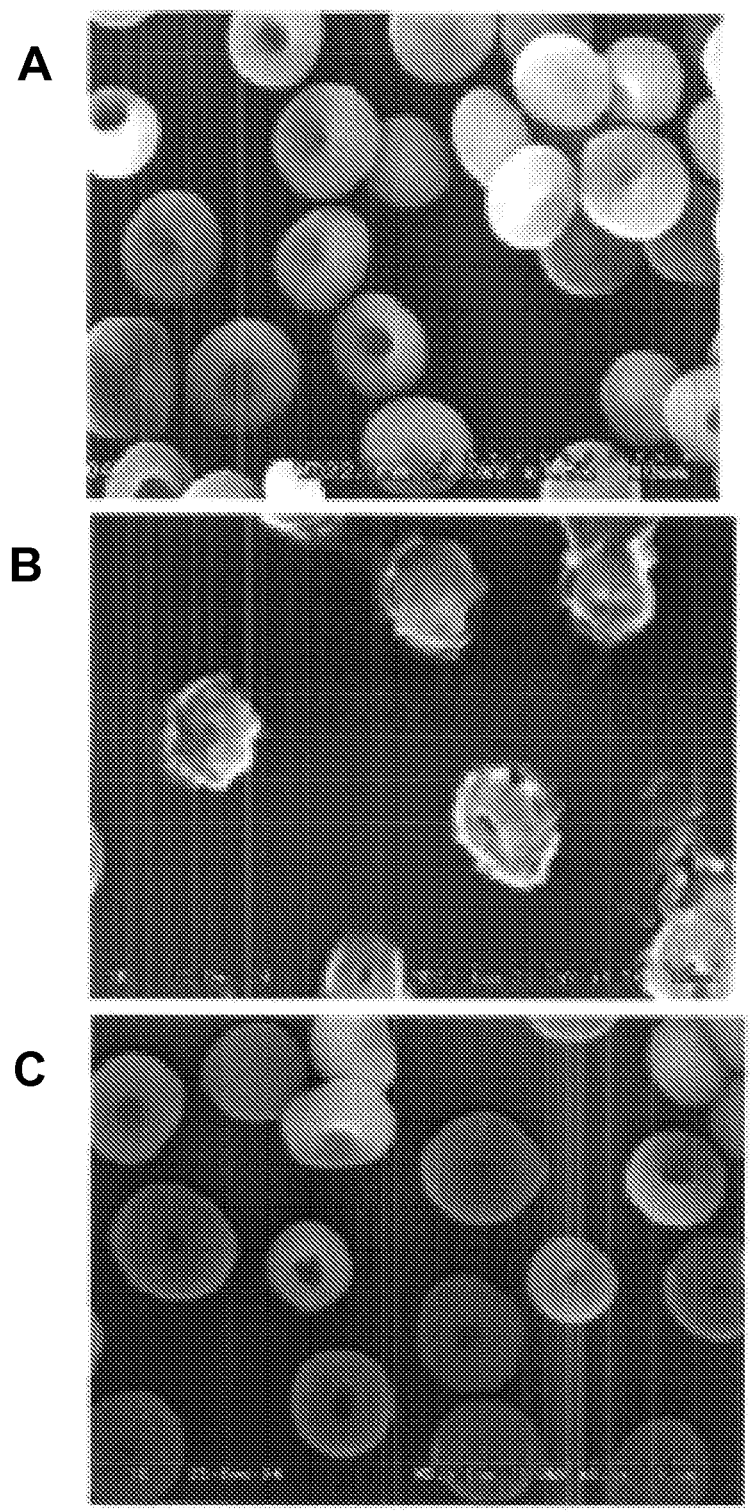
FIG. 20 is an SEM image of gluteraldehyde fixed red blood cells.

FIG. 20 presents scanning electron microscopy (SEM) images taken from samples of normal RBC, ASNase-loaded RBC-Ghost, and LMWP-ASNase-loaded RBC. As seen, while the ASNase-loaded RBC from osmotic rupture/resealing method (i.e. RBC-Ghost) exhibited significant change in shape and morphology, the LMWP-ASNase-loaded RBC showed virtually indistinguishable shape and morphology (i.e. biconcave disk) from those of normal RBC. These findings are in agreement with those reported by many other investigators that PTD-mediated cell encapsulation does not cause any significant perturbation or alteration of the cell membrane (Dietz, G P H and Bahr, M (2004) Molecular Cell Neurosciences 27, 85-131; Schwarze et al. (1999) Science 285, 1569-1572; Suzuki et al. (2002) Journal of Biological Chemistry 25, 2437-2443).

Figure 21:
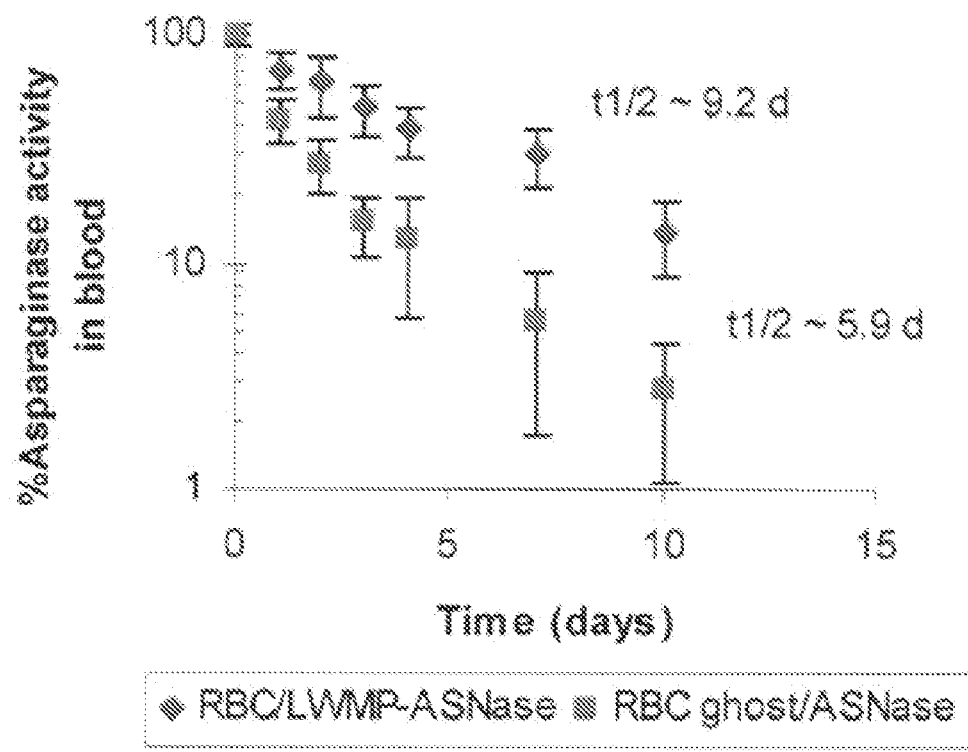
FIG. 21 is a scatter plot showing percent Asperaginase activity in blood as a function of time (days) for RBC/LMP-ASNase or RBC ghost/ASNase. For further methodology information, see Example 12.

To further evaluate these two RBC-encapsulation systems, preliminary clearance studies were carried out. The half-life of ASNase activity in plasma was evaluated after intravenous injection of: (1) ASNase-loaded RBC-Ghost, and (2) LMWP-ASNase-loaded RBC. Each animal group consisted of 4 DBA-2 mice, and each mouse was given 8 units of loaded ASNase activity. Blood samples were withdrawn at different time intervals from the tail vein, and the amount of ASNase activity in the whole blood was measured by direct Nesslerization of produced ammonia (Ho et al. (1970) Journal of Biological Chemistry 245, 3708-15). Results demonstrated that there was almost a two-fold increase in the circulation half-life for the LMWP-ASNase-encapsulated RBC ($t_{1/2}$: 9.2 days) compared to that ($t_{1/2}$: 5.9 days) for the RBC-Ghost (see e.g., FIG. 21). It is currently unknown what the difference between the half-lives of the encapsulated RBC and the normal, untreated RBC. Nonetheless, these results of 2-fold increase of $t_{1/2}$ over RBC-Ghost demonstrate the merit of this approach, as it was reported in the literature that even by utilizing the RBC-Ghost encapsulation method, the in vivo ASNase activity had already been prolonged from 26 hours for the free ASNase to 29 days for the RBC-Ghost-encapsulated ASNase (Kravtzoff et al. (1996) European Journal of Clinical Pharmacology 49, 465-470): already a 10-fold increase. Hence, another 2-fold increase of this $t_{1/2}$ by the encapsulation method described herein is particularly effective.

Figure 22:
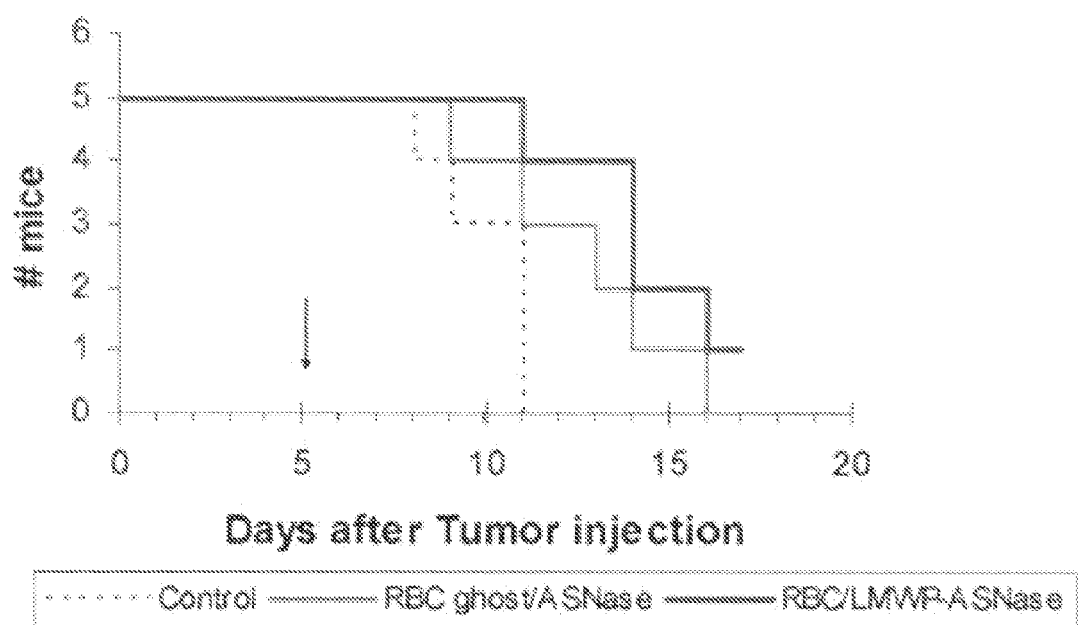
FIG. 22 is a line plot showing survival of DBA/2 mice bearing L5178Y lymphoma cells. Enzyme or saline were given on day 5, at which time symptoms were present. For further methodology information, see Example 12.
Figure 23:
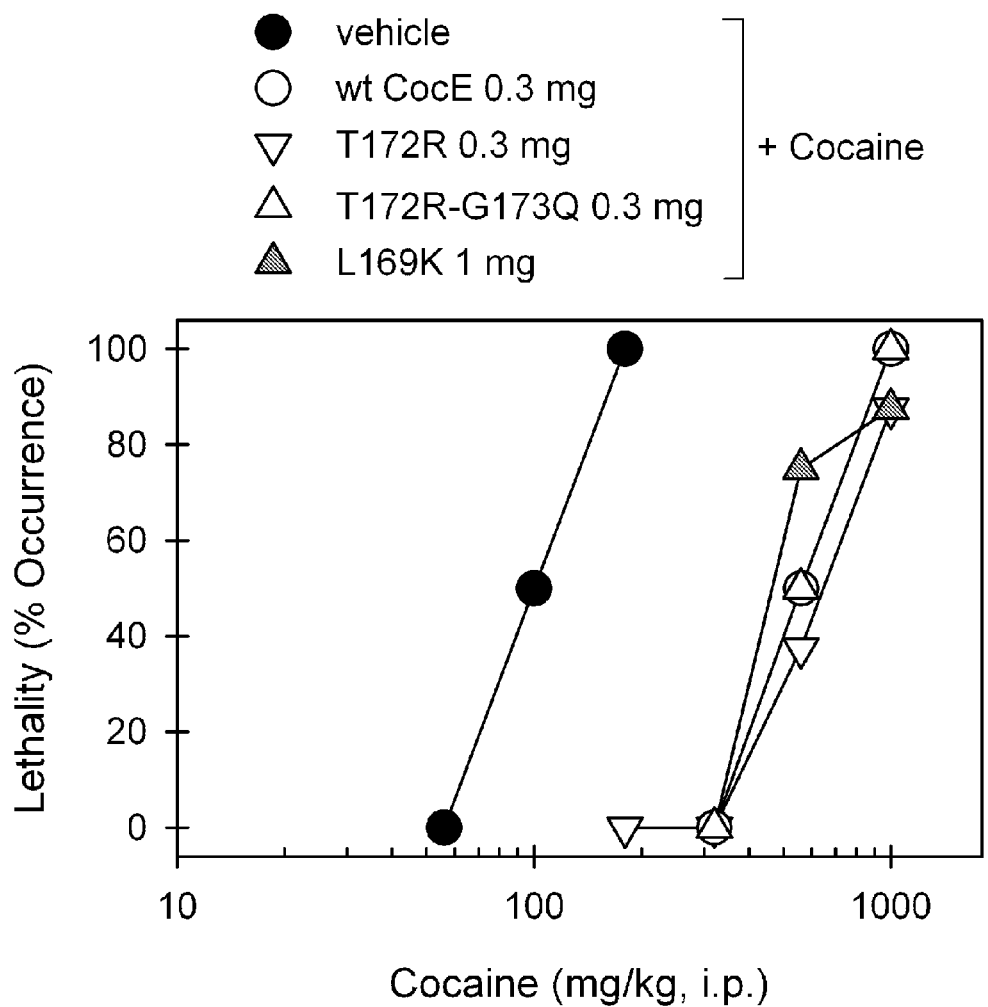
FIG. 23 is a line and scatter plots demonstrating protective effects of CocE and its mutants against cocaine-induced toxicity. The figure depicts percentage of mice lethality exhibiting cocaine-induced lethality as a function of injected cocaine concentration in mice administered wild type CocE (0.3 mg), T172R (0.3 mg), T172R-G173Q (0.3 mg), or L169K (1 mg). CocE or mutants (mg) was administered intravenously 1 minute before cocaine administration (mg/kg, i.p.). Different symbols represent dose-response curves of cocaine-induced lethality in the absence or presence of CocE or mutants. Each data point represents the percentage of mice (n=8 for each dosing condition) exhibiting cocaine-induced lethality.
Figure 24:
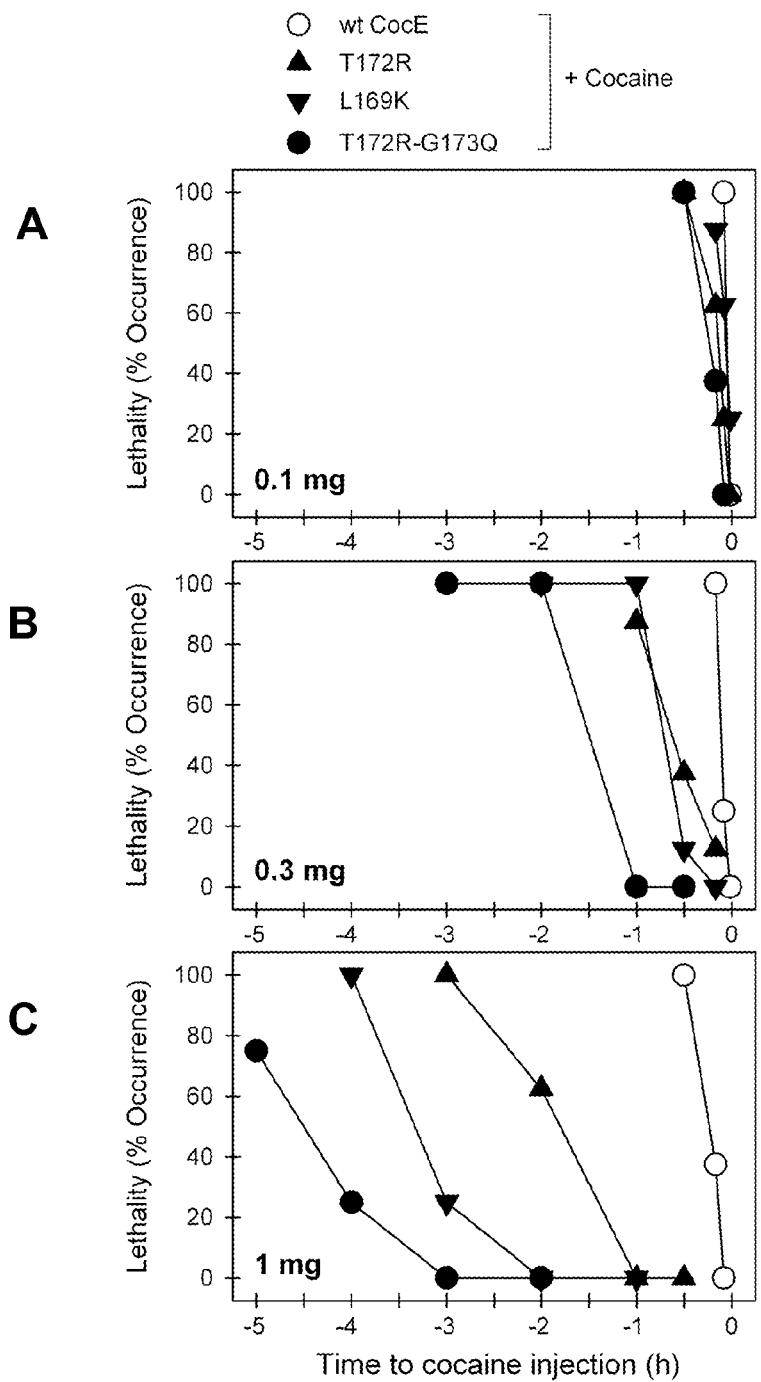
FIG. 24 is a series of line and scatter plots demonstrating time course of protective effects of CocE against cocaine toxicity. CocE or mutants (0.1, 0.3, and 1 mg, i.v.) was administered at different time points before administration of i.p. cocaine 180 mg/kg.
Figure 25:
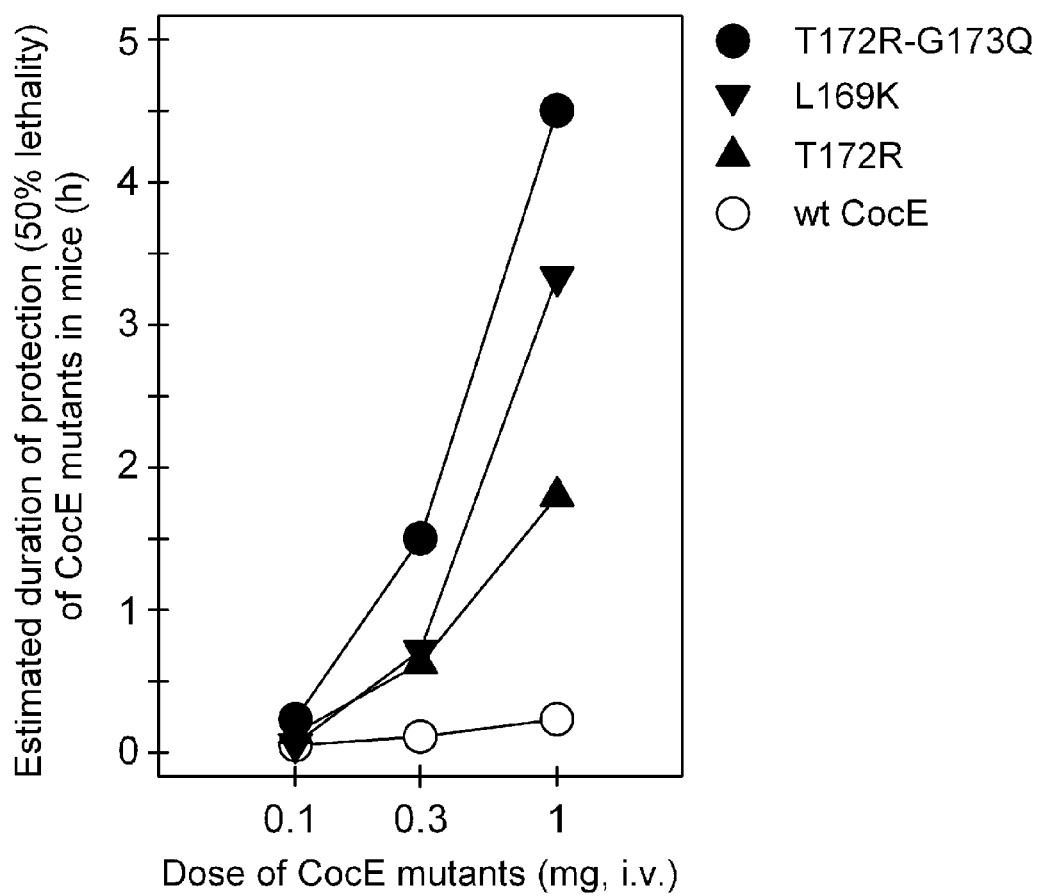
FIG. 25 is a line and scatter plot demonstrating estimated duration of protection for 50% lethality: The figure depicts the estimated duration (hours) of protection (50% lethality) of CocE mutants in mice as a function of dosage (mg, i.v.) of T172R-G173Q, L169K, T172R, and wild type CocE. The time required to reach 50% lethality was determined from FIG. 24.
Figure 26:
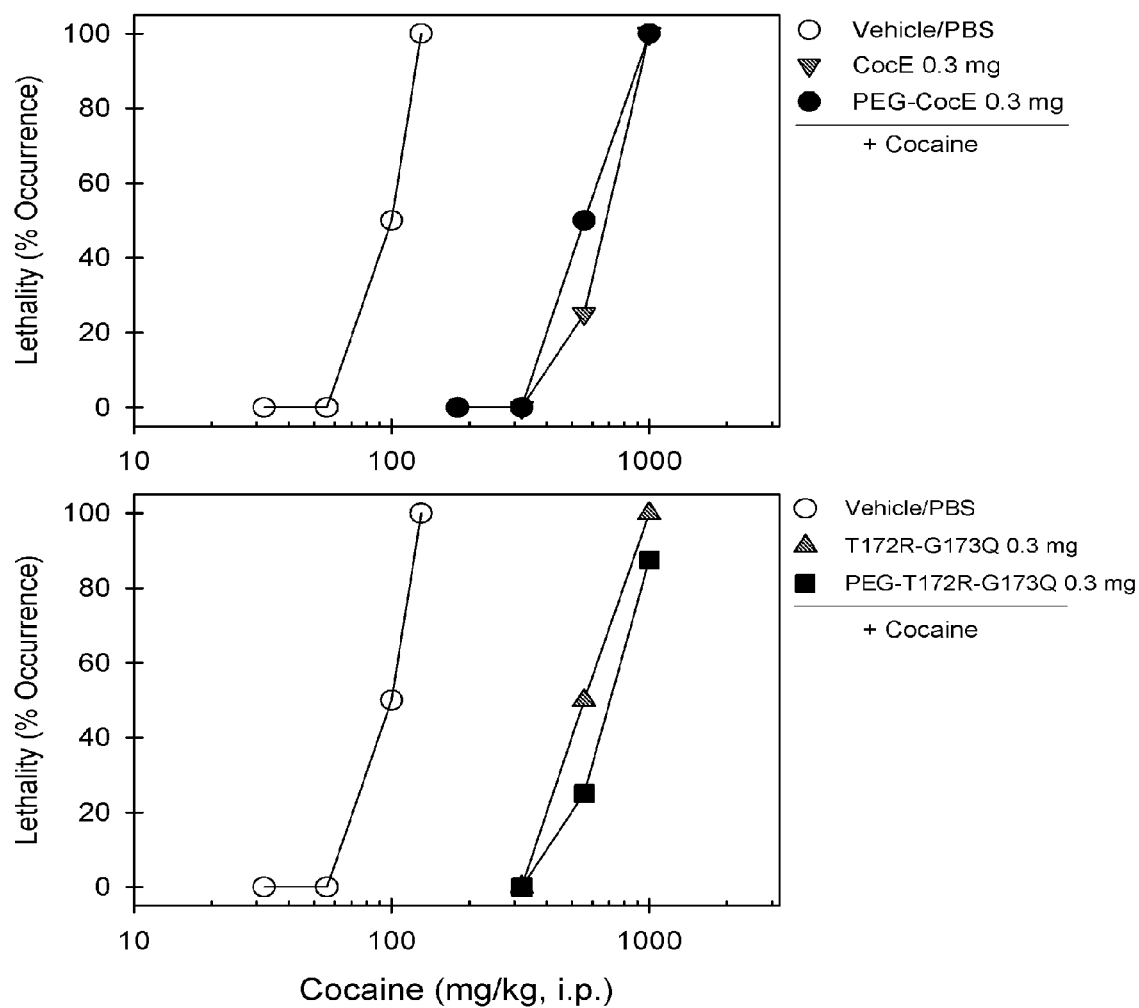
FIG. 26 is a series of line and scatter plots demonstrating protective effects of CocE, T172R-G173Q, and their pegylated forms against cocaine-induced toxicity. Each enzyme (0.3 mg) was administered intravenously 1 min before cocaine administration (mg/kg, i.p.). Different symbols represent dose-response curves of cocaine-induced lethality in the absence or presence of the enzyme. Each data point represents the percentage of mice (n=8 for each dosing condition) exhibiting cocaine-induced lethality.

To confirm that the RBC-encapsulated ASNase could still retain its original biological functions, anti-tumor effects by both the RBC-Ghost-ASNase and the RBC-ASNase were examined on tumor-bearing mice. L5178Y mouse lymphoma cells were cultured, and to each DBA/2 mouse $7 \times 10^5$ cancer cells were injected intraperitonially. Five days after tumor implantation, mice with similar bodyweights were selected and divided into three groups: (1) Control group given saline only; (2) ASNase-loaded RBC-Ghost; and (3) LMWP-ASNase-loaded RBC. Each group consisted of 5 mice, and each experimental mouse was given 0.1 mL of the drug-encapsulated RBC (or Ghost). Results showed that the average survival times for the untreated control, ASNase-RBC-Ghost-treated, and LMWP-ASNase-RBC-treated groups were 10.0, 12.6, and 14.4 days, respectively (see e.g., FIG. 22). It should be noted that although the survival time among the three groups differed by only about 2 days, the effects of the treatment by the RBC-encapsulated ASNase was still quite dramatic; considering the fact that only 0.1 mL of the RBC suspension, which was equivalent to merely 5% of the total blood volume of the mouse, was given to each mouse for the anti-tumor treatment. Overall, these findings with the ASNase model enzyme demonstrated that the RBC-encapsulated enzyme was still therapeutically active. It is noted that cocaine is more permeable across the RBC membrane than the asparaginase substrate.

Thus, utilization of RBC-encapsulated CocE in treating cocaine-related conditions is an effective approach because cocaine readily crosses the RBC membrane (and actually somewhat concentrates in RBC) (Javaid et al. (1978) Journal of Chromatography 15, 105-113), PTD-mediated encapsulation does not alter the physical and/or chemical properties of the RBC, and the RBC-encapsulated enzyme functions as if free.

Example 13

Endotoxin Removal

Endotoxin contamination of CocE mutants can be performed in several ways. Ideally, endotoxin decontamination decreases the concentration to levels less than 10 EU/mg protein. Methods of decontamination include alternative ion-exchange column chromatography conditions, size exclusion, polyethyleneimine (PEI) and hydrophobic column chromatography, ultrafiltration and detergent extraction. An endotoxin detection system (PYROGENT 5000, Cambrex) is used to determine the endotoxin content of preparations. The assay is based on the anti-LPS factor from Limulus amebocyte lysate (LAL). The sensitivity of the assay is between 0.01 and 100 EU/ml, well within the levels required. The spectrophotometric assay is designed in a 96-well microtiter-plate format. Fractionation of endotoxin and CocE and/or mutant CocE by the following procedures can be assayed for both endotoxin level and cocaine esterase activity. Cocaine esterase activity is measured utiliizing a spectrophotometric assay that takes advantage of the intrinsic absorption of cocaine at 240 nm. Upon hydrolysis, the absorption spectra reveals a dramatic reduction in the 240 nm peak (Turner et al. (2002) Biochemistry 41, 12297-12307).

Anion exchange chromatography: Current conditions involve the use of fast performance liquid chromatography (FPLC)on a Q-Sepharose column at pH 8.0 for endotoxin decontamination. The buffer conditions (pH) can be optimized to maximize the both the adsorption of CocE and/or mutant CocE and separation of endotoxin. Fluted fractions are assessed by activity measure of CocE or mutant CocE activity (spectroscopic assay of the hydrolysis of cocaine, absorption at 240 nm). Endotoxin levels are assessed using PYROGENT 5000 (above).

Size Exclusion Chromatography and Ultrafiltration: Endotoxin can exist as monomeric forms (MW~1-2×10$^4$) or in micellar form (MW~4×10$^5$ to 1×10$^6$), depending on the buffer conditions. The presence of detergents such as cholate favors the monomeric form whereas divalent cations (e.g. Ca$^{2+}$) favor the micellar form (Hirayama, C and Sakata, M (2002) Journal of Chromatography B Analytical Technology Biomedical Life Science 781, 419-432). This property of endotoxin is used to separate the micellar (i.e. in the presence of divalent cations such as Mg$^{2+}$ or Ca$^{2+}$) from CocE and/or mutant CocE by Gel filtration chromatography using either a Sephadex 75 or Sephadex 200 (Pharmacia) column resin. Micellar endotoxin should not be retained on the column and should pass through the void whereas CocE and/or mutant CocE should elute as a monodispersed protein corresponding to a 65 kDa protein. Similarly, the capacity of ultrafiltration units to separate the micellar forms of endotoxn from CocE and/or mutant CocE will be assessed. Ultrafiltration units are now available with molecular weight cutoffs of 3×10$^5$ to 1×10$^6$, well within the range required to retain micellar endotoxin but not CocE itself.

Polyethyleneimine Chromatography: Mitzner et al. (1993) and Morimoto et al. (1985) have used PEI-immobilized on cellulose beads or on cellulose fiber, respectively to remove endotoxin from BSA preparations. PEI-chromatography column is a very weak anion exchanger that may in fact take advantage of some hydrophobic properties of endotoxin and thus preferentially adsorb it. Various PEI-silica bead preparations are available from Sigma, depending on the bead size. While silica-based beads are more classically associated with HPLC applications we will pack columns for lower pressure work and will select the 200 um mesh sizes.

Triton X-114 Extraction: Triton X-114 phase separation has been successfully used to separate endotoxin from albumin and catalase (Aida, Y and Pabst, M J (1990) J Immunological Methods 132, 191-195). Adia and Pabst report a 1000-fold decrease in endotoxin concentration following a single Triton X-114 extraction step. CocE and mutant CocE samples are incubated with equal volumes of Triton 114 and allowed to incubate first on ice and then at 37° C. for 15 minutes. The Triton X-114 phase that contains the endotoxin is removed by centrifugation. As noted earlier it has been demonstrated that CocE is considerably thermal labile, but may be protected somewhat by the presence of the substrate, cocaine. If incubation of CocE with Triton X-114 at 37° C. results in significant CocE inactivation, the enzyme will be stabilized by including excess substrate during the extraction.

Example 14

Mutagenesis of the CocE Host Organism

There exists several bacterial strains that exhibit temperature sensitive growth on cocaine esterase byproducts, including several *Pseudomonas* strains, and these organisms can be adapted for temperature sensitive growth on cocaine by addition of the CocE gene encoded within suitable plasmid vectors. For example, the CocE gene was originally sequenced from *Rhodococcus* MB1 by subcloning gene fragments into *Rhodococcus erythropolis* CW25, a bacterium unable to metabolize cocaine but able to grow on the cocaine esterase byproducts ecgonine methyl ester and benzoate (Bresler et al. (2000) Applied & Environmental Microbiology 66, 904-908). The CocE gene has been subcloned into shuttle vectors pJAK-14 and pMMB67EH (see e.g., Example 1). These plasmids are capable of expression in any gram-negative bacterium including *Pseudomonas*, and additionally the pMMB67EH plasmid enables high levels of expression and ease of transformation by bacterial conjugation with the use of helper plasmid pRK2013. Transformation of either plasmid into bacteria that exhibit temperature sensitive growth on cocaine esterase byproducts (e.g., *Pseudomonas* strains), enables temperature sensitive growth on plates containing cocaine as a sole source of carbon. Mutagenesis of both the original *Rhodococcus* MB1 and the CocE plasmid-containing *Pseudomonas* strains is performed using UV-light radiation at 260 nm. Exposure is titrated such that 90-95% of cells are killed. The remaining cells are recovered in nutrient media for 1 hr at 26° C., collected and enriched in the presence of cocaine as previously described (Britt, et al. (1992) Journal of Bacteriology 174, 2087-2094). Enrichment is performed at 37° C. to select for thermostable variants of the CocE. Finally, cells are plated onto minimal media agar plates containing 10 mM cocaine and incubated at 37° C. Single colonies are grown and tested for CocE activity at 37° C. PCR amplification of the CocE gene is performed on mutants found to produce active and soluble CocE at 37° C., and the amplification products are subcloned into the pET-22B(+) plasmid for further characterization. As a prelude to CocE mutagenesis, it may be necessary to mutagenize the native *Pseudomonas* strains in order to preselect for no temperature sensitivity at 37° C. when grown on cocaine hydrolysis products, and then demonstrate temperature sensitivity on cocaine at 37° C. after cloning in CocE.

Example 15

High Throughput Screening Method for Identification of Thermostable CocE Mutants Several high throughput screening methods for identification of thermostable CocE variants were implemented. Because the wild-type enzyme is known to have thermal-instability at temperatures above 30° C., after transformation into *E. coli* BL21 cells, colonies are subcultured and protein expression induced at 16° C. Expressed proteins are then tested for esterase activity at temperatures 30° C. and above. After several rounds of mutagenesis and testing at increasing temperatures thermostable mutants are achieved. Each individual mutant CocE is then prepared, purified, and tested for activity and thermostability at 37° C., as described above (see Examples 1 and 4)

Bacterial colonies containing mutant polypeptides are screened from directly from agar plates by nitrocellulose filter imprint of replica plates followed by lysis of the bacteria and protein fixation. Determination of enzymatic activity at various temperatures is achieved by monitoring the accumulation of benzoic acid, the acidic by product of (−)cocaine. A moist nitrocellulose imprint is placed onto a dried filter paper previously saturated with a mixture of cocaine at pH 7.4 with no buffer and a pH indicator that transitions from colorless to color upon acidification e.g., methyl red. Active enzyme is identified by color change and colonies are appropriately harvested. The detection method based on acidification through the formation of benzoic acid is employed for the detection of cell expression of catalytic antibodies that hydrolyze cocaine at the benzoyl ester group, the same site cleaved by CocE. Alternatively, detection by nitrocellulose imprint is achieved by exposure to a cocaine thiol-derivative and subsequent detection of sulfhydryl groups via a precipitating heavy-metal (e.g., mercury-based) indicator system.

Figure 6:
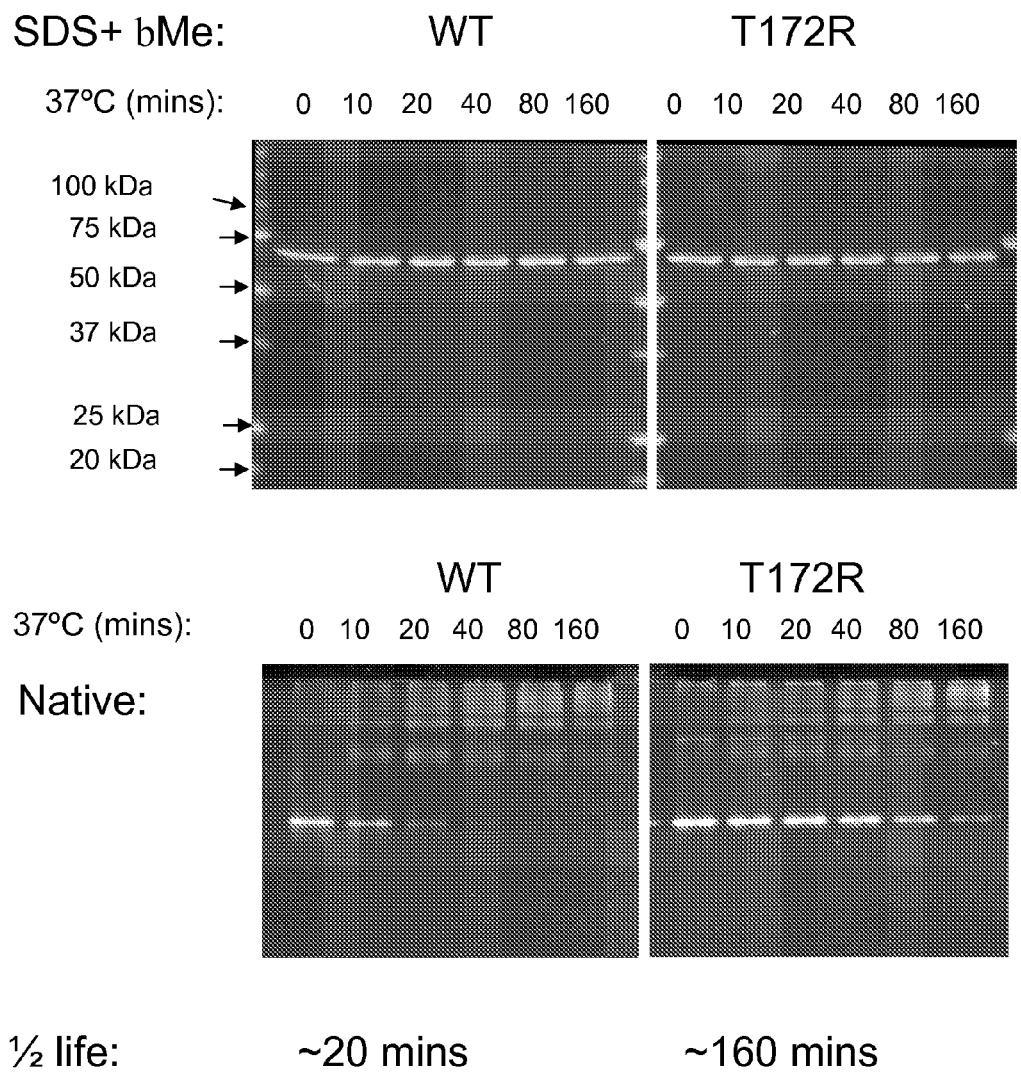
FIG. 6 is a set of photographs of the total protein staining after PAGE separation of wild-type and T172R mutant CocE using denaturing (SDS+βMe) or non-denaturing (Native) conditions after incubation at 37 C for various time points. For more information see Example 4.
Figure 7:
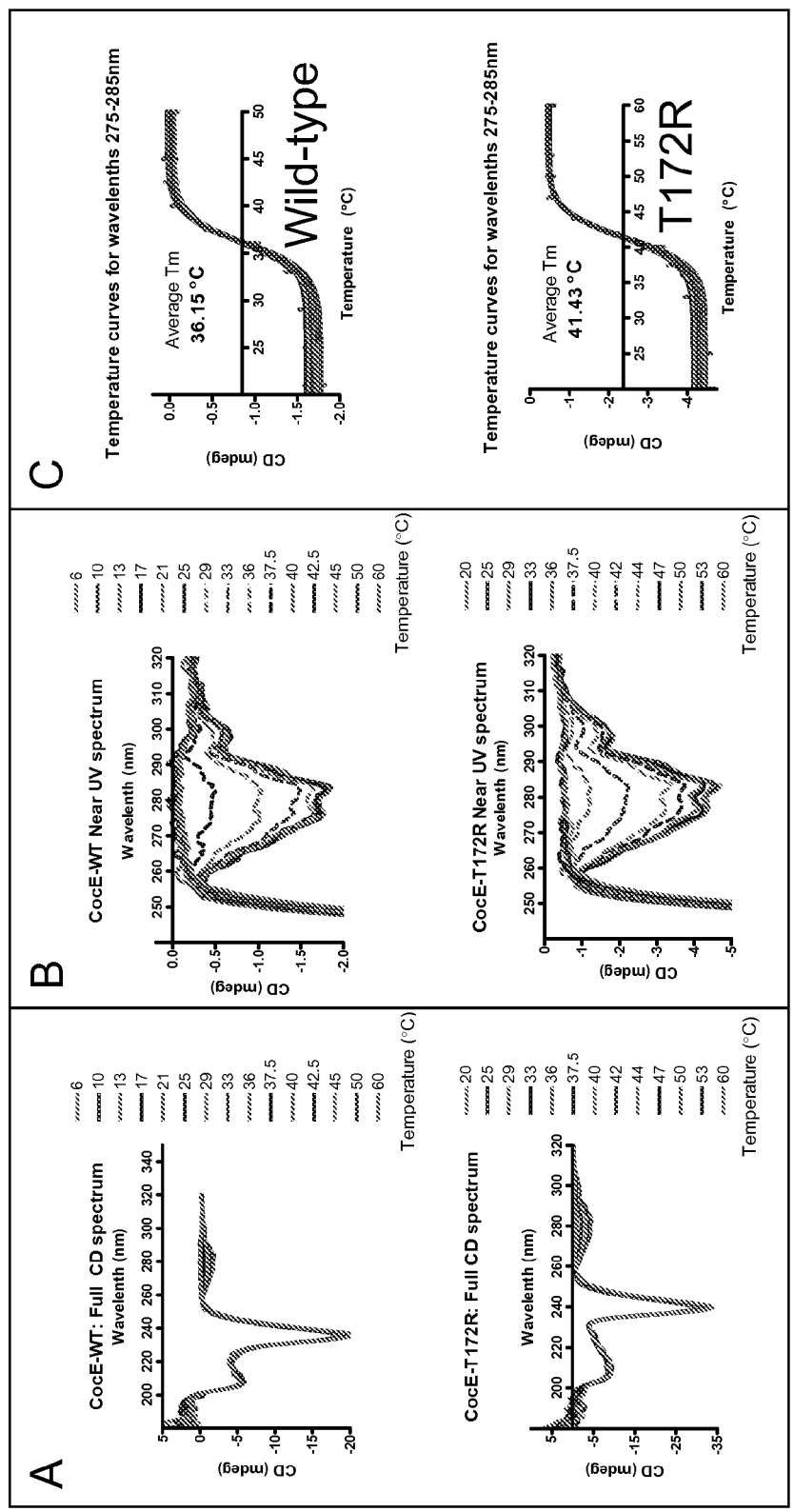
FIG. 7 is a line plot depicting the circular dichroism determined melting temperatures of wild-type and T172R CocE. The full spectrum is shown in A, the near-UV spectrum is shown in B, and the estimated melting temperature for each mutant is shown in C. For more information see Example 4.
Figure 8:
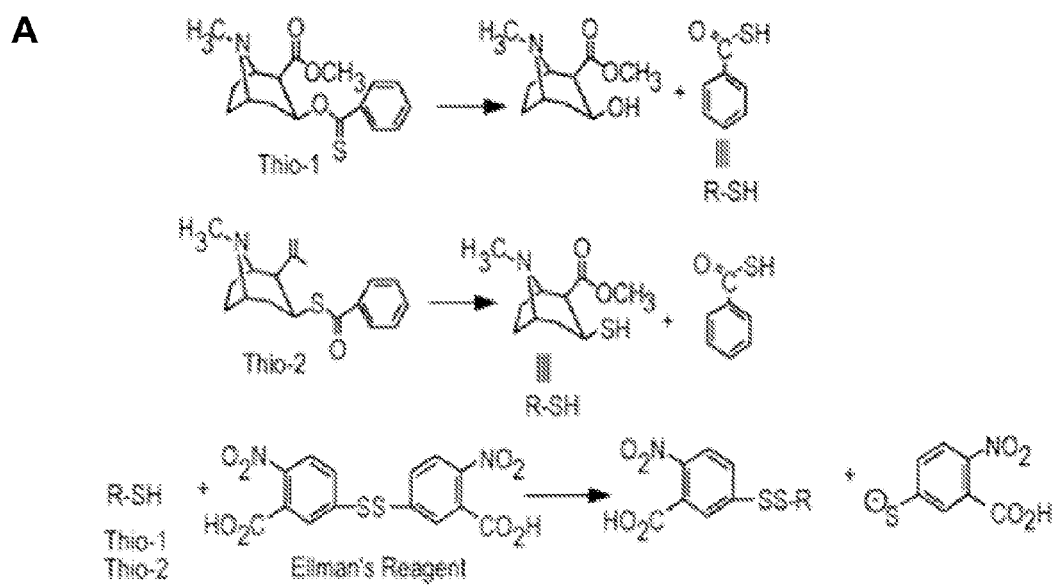
FIG. 8 contains (A) a drawing of the hydrolysis of the benzoylthioester derivative of cocaine (thio-1) and the descarbomethoxy cocaine (thio-2) followed by reaction of the released thiols (R—SH) with Ellman's reagent; and (B) a line plot showing the colorimetric reaction of control BL21 cells and BL21 cells containing CocE incubated with the benzoylthioester derivative (thio-1) and Ellman's reagent. For more information see Example 15.
Figure 8:
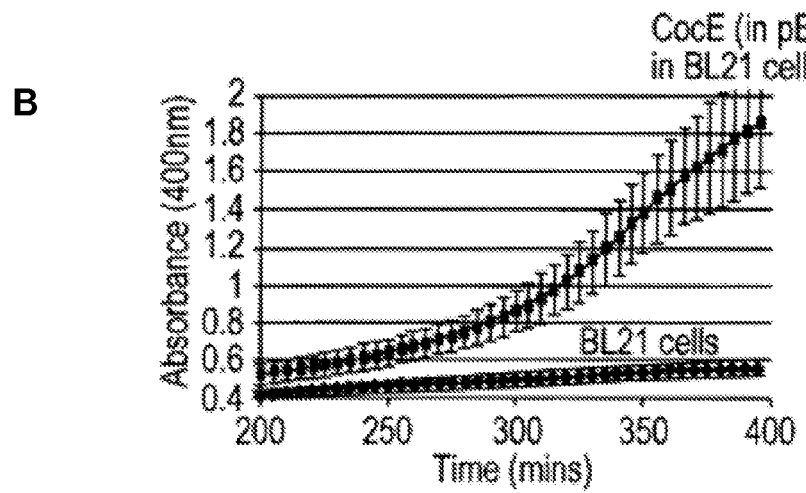

Bacterial colonies containing mutant polypeptides are also screened by subculturing into liquid medium and testing directly for cocaine esterase activity using a cocaine thiol-derivative and detection using the colorimetric thiol indicator, Ellman's reagent (see e.g., FIG. 6). Ellman's reagent rapidly forms a disulfide bond with free thiol-groups and releases a colored thiolate ion which absorbs at 412 nm. Cultures incubated overnight at 16° C. in the presence of IPTG to induce protein expression (20 μl) are mixed with 1 mM benzoylthioester cocaine derivative, and 500 uM Ellman's reagent in 100 mM sodium phosphate pH 7.4 to a final volume of 200 μl. Results (see e.g., FIG. 6) indicate that cells containing the wild-type CocE enzyme are able to cleave the benzoylthioester at much higher levels than cells alone.

Finally bacterial colonies containing mutant polypeptides are screened by subculturing into liquid medium followed by lysis and isolation of mutant polypeptides using an affinity medium. For example, lysed cells are washed through nickel-agarose filter-plates allowing collection and subsequent elution of 6× HIS tagged proteins (for example, Ni-NTA Super-flow 96-Bio-robot kit (Qiagen). Alternatively, cells are lysed within nickel-coated microtiter plates allowing binding of 6× HIS fusion proteins and subsequent removal of contaminants (for example, immobilizer nickel chelate plates (Nunc) or NEN Nickel-chelate flash plates (Perkin Elmer)). Similarly, lysed cells are incubated with nickel coated microbeads (such as Ni-NTA magnetic agarose beads (Qiagen)), followed by subsequent removal of contaminating proteins. Isolated esterase protein activity are then tested using any of the assays previously mentioned (such as the spectrophotometric activity assay (Examples 1 and 4), the tritiated cocaine activity assay (Example 1), the benzoic acid pH indication activity assay, the thiol-derivative cocaine detection systems, the use of cocaine aptamers (Stojanovic, M. N., de Prada, P. & Landry, D. W. (2001) J Am Chem Soc 123, 4928-31; Stojanovic, M. N. & Landry, D. W. (2002) J Am Chem Soc 124, 9678-9) by monitoring changes in fluorescence upon degradation of cocaine, or by the use of a generic esterase substrate such as 4-nitrophenyl acetate and monitoring of colorimetric changes at 420 nm as described previously (Halgasova, N. et al. (1994) Biochem J 298 Pt 3, 751-5; O'Conner, C. J. & Manuel, R. D. (1993) J Dairy Sci. 76:3674-3682).

Example 16

Preliminary Analysis of N197K Mutant Polypeptide

Preliminary analysis of the N197K mutant polypeptide (SEQ ID NO: 42) showed good stability after 1 hour at 37° C. on day 0. Vmax and Km values are shown in Table 5. A recheck on day 3 showed similar stability. Vmax and Km values are shown in Table 6. Higher Km values on day 3 were due to reuse of old cocaine. Gel filtration of samples incubated at 37° C. showed formation of aggregates.

TABLE 5

N197K initial test (Day 0)

| Equation 1 Best-fit values | N197K (0) | N197K (60) |
|---|---|---|
| VMAX | 2928 | 2187 |
| KM | 34.77 | 24.24 |

TABLE 6

N197K repeat test (Day 3)

| Equation 1 Best-fit values | N197K (0) | N197K (60) |
|---|---|---|
| VMAX | 3357 | 3085 |
| KM | 102.2 | 113.5 |

Example 17

Identification of Thermally Stable Mutant CocE Polypeptides

Figure 27:
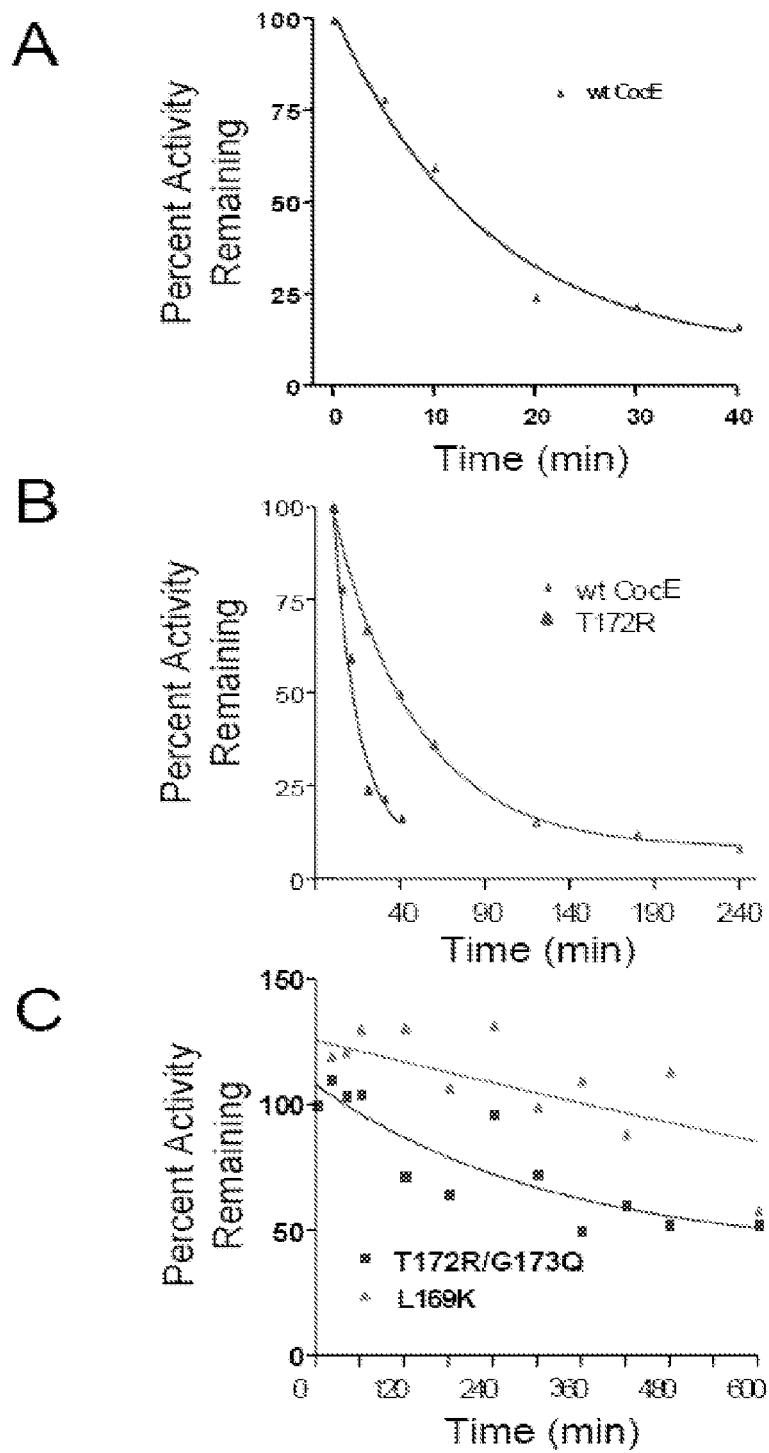
FIG. 27 is a series of line and scatter plots showing the thermal stability of cocaine esterase and mutants: (A) wild-type CocE, (B) T172R, (C) T272R/G173Q and L169K. For further methodology information, see Example 17.

Thermally stable mutant CocE polypeptides were identified by determining $\tau_{1/2}$ of the mutant CocE polypeptides. Briefly, enzymes were preincubated at 37° C. for varying times. Activity measurements were determined at RT (25° C.). Mutant enzymes with $\tau_{1/2}$ of greater than 12 minutes (the $\tau_{1/2}$ of wild type CocE) were considered thermally stable (See, e.g., FIG. 27 and Table 7). As demonstrated by the combination mutant CocE polypeptide T172R/G173Q, in various embodiments, the combination of two single mutations with lower or no stability can result in a thermally stable combination.

TABLE 7

Thermally stable mutant CocE polypeptides

| Mutant | Stability @ 37° C. ($t_{1/2}$) |
|---|---|
| T122A | No |
| Q123E | No |
| S159A | No |
| S140A | No |
| S167A/W52L | No |
| T172R | ~46 min |
| V121D | No |
| L163V | No |
| F189A | No |
| F189A/T172R | ~40 min (Similar to T172R) |
| C107S | No |
| W220A | No |
| F189L | No |
| A193D | No |
| T172R/A193D | ~40 min (Similar to T172R) |
| G173Q | ~25 min |
| T254R | No |
| N42V | No |
| T172R/G173Q | ~326 min |
| G171Q/T172R/G173Q | No |
| G171A | No |
| G173A | No |
| wt-I175-G-D185 | No |
| wt-T176-G-G-D185 | No |
| T172R/G173Q-I175-G-D185 | |
| T172R/G173Q-I175-G-A186 | ~75 min |
| T172R/G173Q-T176-G-G-D185 | ~75 min |
| S177Q | No |
| D45R | No |
| F47R | No |
| L169K | ~274 min |
| L174R | No |
| A181K | No |
| S179R | No |
| F189K | 25 min |
| V190K | No |
| A194K | No |
| R182K | No |

Example 18

Protection of Aggregation of Thermal Stable Cocaine Esterase Mutants

Figure 28:
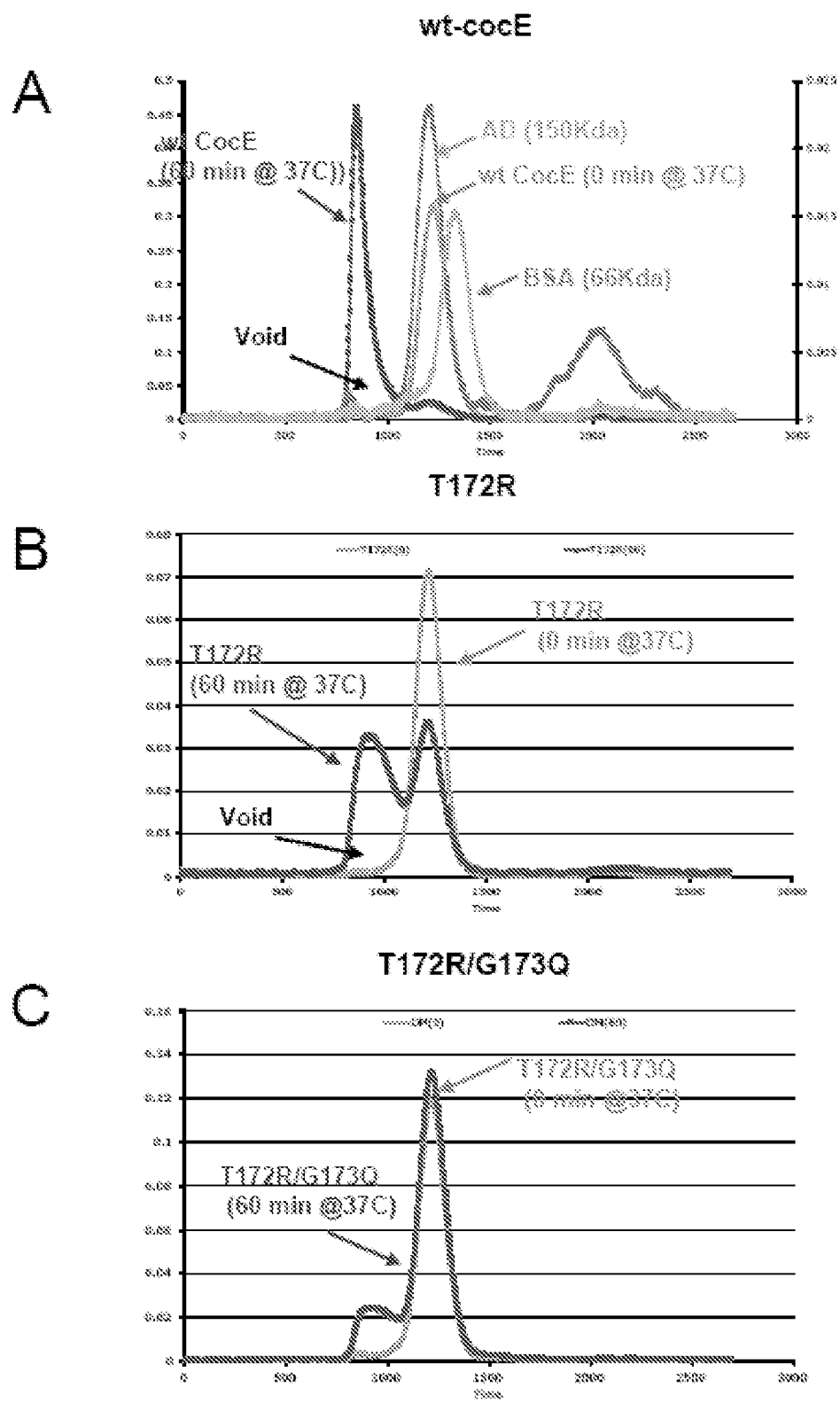
FIG. 28 is a series of chromatograms showing enzymes preincubated at 37° C. for 0 minutes or 60 minutes and resolved by size exclusion chromatography (A) wild-type CocE, (B) T172R, (C) T172R/G173Q. Molecular weight standards, BSA (66 Kda) and AD (150 Kda) are included in A. For further methodology information, see Example 18.

Protection from aggregation of thermal stable CocE mutants was assessed using size exclusion chromatography. Briefly, enzymes were preincubated at 37° C. for 0 minutes or 60 minutes and resolved by size exclusion chromatography. Results for wild-type CocE, T172R and T172R/G173Q are shown in FIG. 28.

Example 19

Low-UV Spectra

Low-UV CD spectra data were obtained using an Aviv Spectropolarimeter Mode 400, with the help of Norma Greenfield, UMDNJ, using a 5-cell holder and 0.2 mg/ml protein concentrations. Raw data values obtained were blanked on control PBS, smoothed, and deconvoluted using the CCA algorithm as described by A. Perczel, K. Park, and G. D. Fasman, [Analysis of the circular dichroism spectrum of proteins using the convex constraint algorithm: a practical guide. Analytical Biochemistry 203, 83-93 (1992).] This algorithm finds the minimum number of curves needed to reconstruct a data set, and expresses the percentage each curve contributes to the data set as a function of temperature.

Below is presented a low UV CCA denconvolution analysis of CocE WT and 4 mutants, obtained in a single CD spectra melt using a 5-cell holder. The experiment was performed over the period of 8 hours, from 0-80° C.

Figure 29:
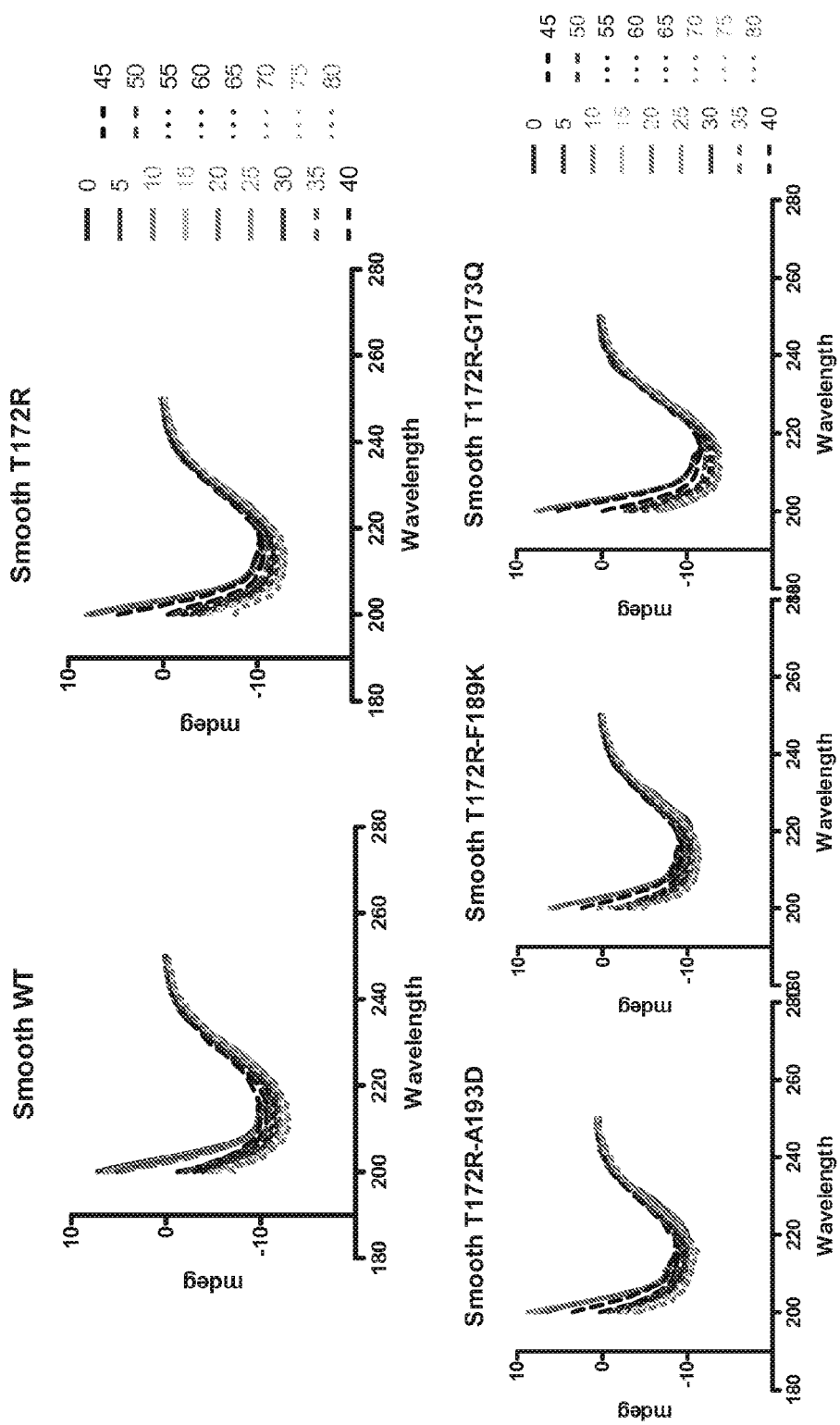
FIG. 29 is a series of smoothed CD spectra of wild-type CocE and four mutants showing tempature dependent melting observed between 200 and 250 nm. For further methodology information, see Example 19.
Figure 30:
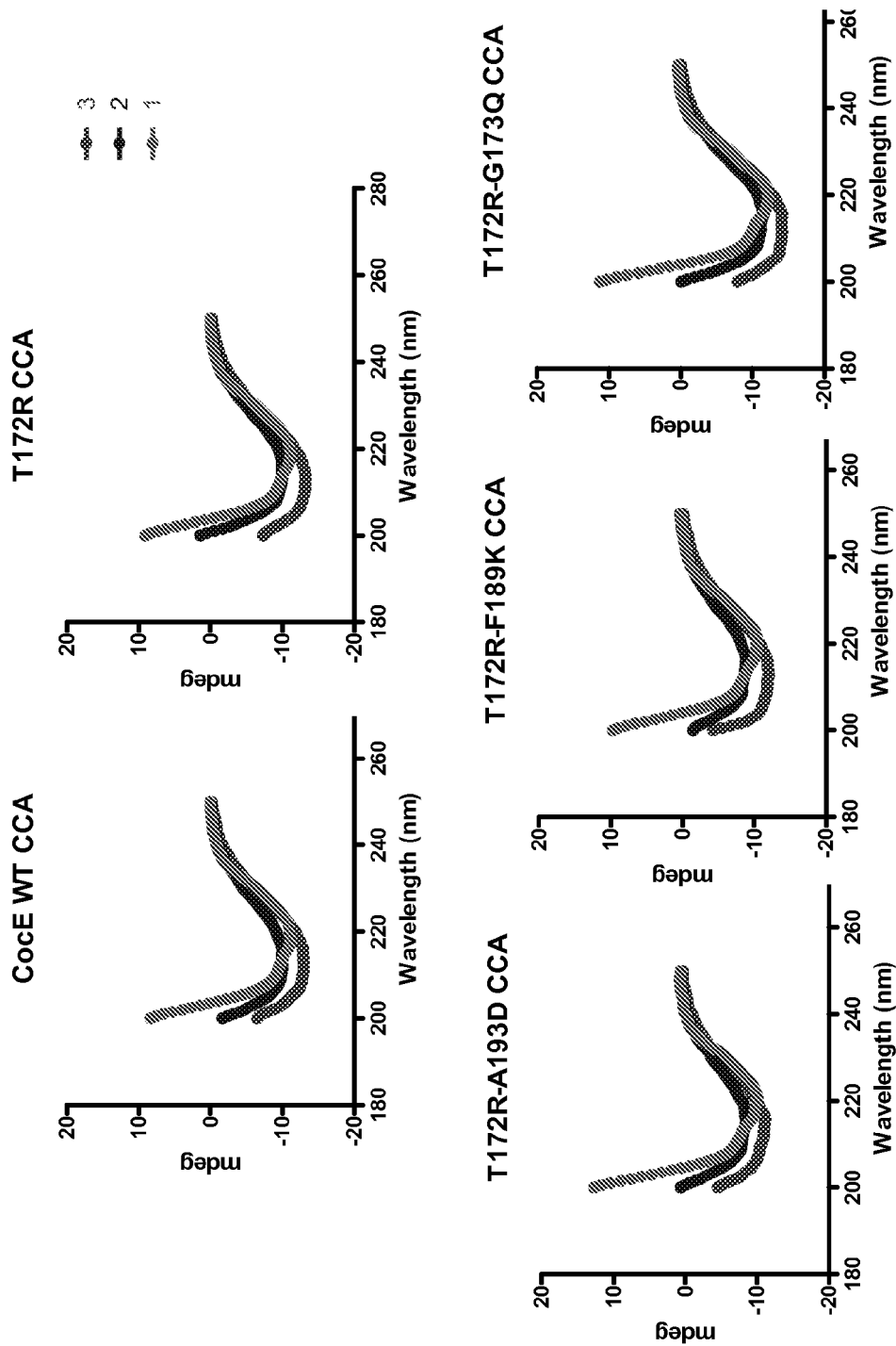
FIG. 30 is a series of spectra for wild-type CocE and four mutants deconvoluted to 3 curves via the CCA algorithm suggesting that the melting of CocE is at least a two-step process moving from the original curve (curve 1) to an intermediate unfolding step (curve 2) to a fully denatured protein (curve 3). For further methodology information, see Example 19.
Figure 31:
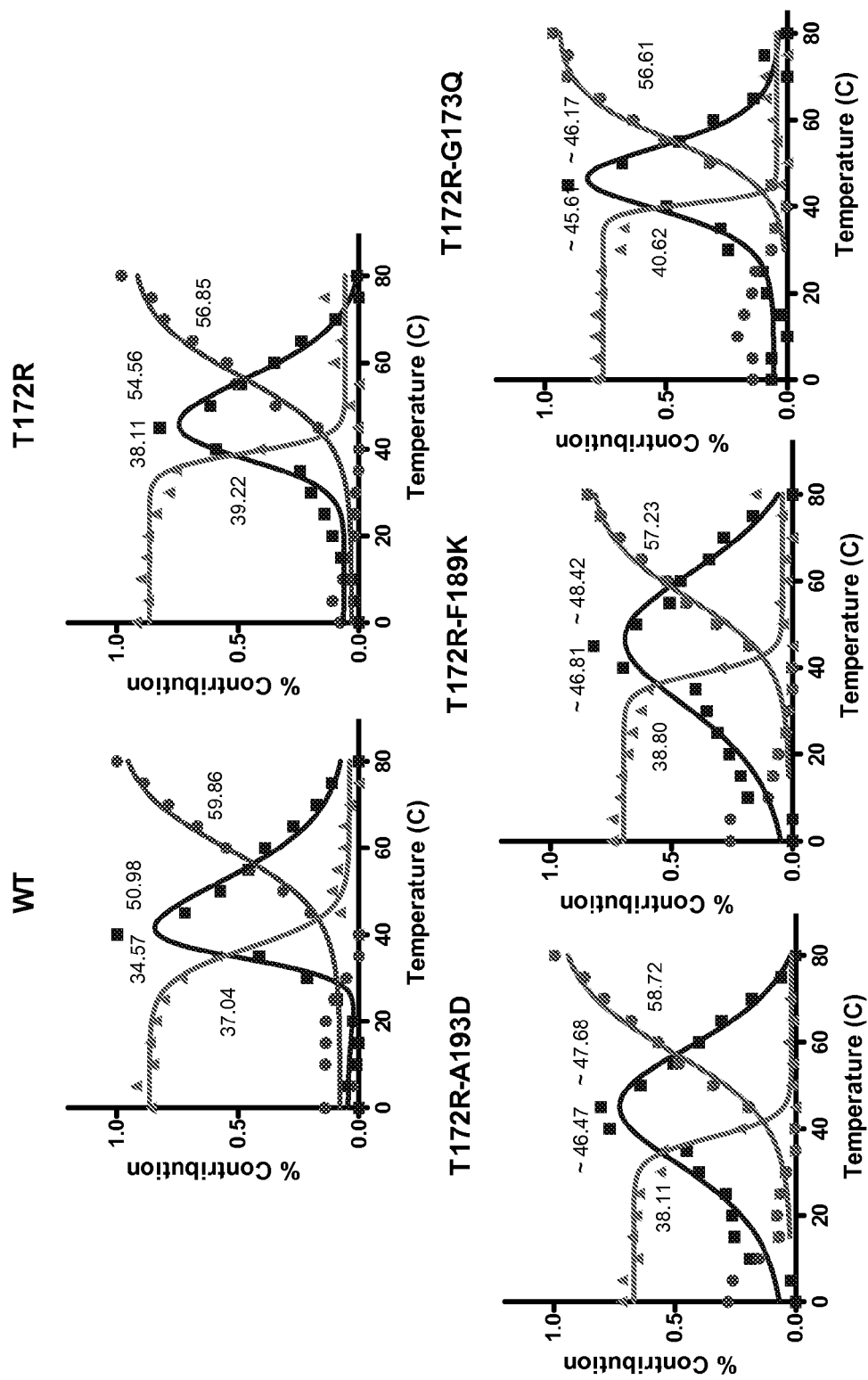
FIG. 31 is a series of line and scatter plots showing percentage contribution of each temperature in describing the 3 deconvoluted CCA curves shown in FIG. 30. For further methodology information, see Example 19.
Figure 32:
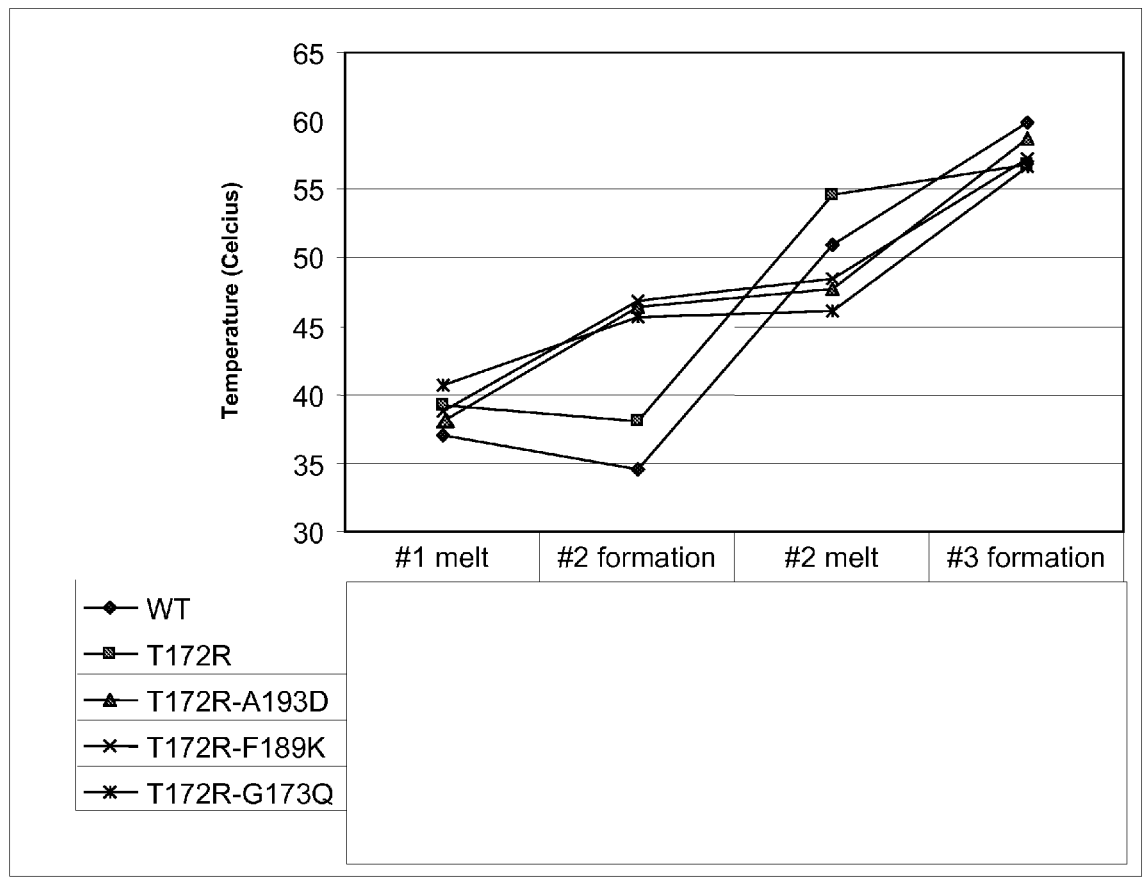
FIG. 32 is a line and scatter plot showing melting and formation temperatures for (1) the initial spectra melts, (2) the formation and melt of the intermediate state, and (3) the accumulation of the fully melted protein. For further methodology information, see Example 19.

Temperature dependent melting was observed between the wavelengths tested (200-250 nm), and the smoothed spectra for each mutant are shown in FIG. 29. Deconvolution via the CCA algorithm indicated that each spectra was best described by a set of three curves, as shown in FIG. 30. This suggests that the melting of CocE is at least a two step process, moving from an original curve (curve 1) to an intermediate unfolding step (curve 2), and finally fully denatured protein (curve 3). The % contribution that each temperature played in describing these three curves is shown in FIG. 31. Dose response analysis was used to approximate the temperature at which the initial spectra melts (1), the formation and melt of the intermediate state (2), and the accumulation of the fully melted protein (3). These numbers were collected and plotted in FIG. 32 and shown in Table 8.

TABLE 8

Melting points of each step

|  | #1 melt | #2 formation | #2 melt | #3 formation |
|---|---|---|---|---|
| ♦ WT | 37.04 | 34.57 | 50.98 | 59.86 |
| ■ T172R | 39.22 | 38.11 | 54.56 | 56.85 |
| T172R-A193D | 38.11 | 46.47 | 47.68 | 58.72 |
| ✕ T172R-F189K | 38.8 | 46.81 | 48.42 | 57.23 |
| ✻ T172R-G173Q | 40.62 | 45.61 | 46.17 | 56.61 |

The most thermostable mutant T172R-G173Q (as determined in other assays) showed the highest temperature melting of the original curve 1 (40° C. vs 37° C. for wild-type), and the lowest temperature for both disappearance of the curve 2 intermediate (46° C. vs 50° C. for wild-type) and appearance of the fully melted curve 3 (56° C. vs 59° C. for wild-type).

In summary, it appears that all mutants undergo a 2-step melting process.

Example 20

Stabilization Using Products and Inhibitors

Cocaine esterase (CocE) cleaves cocaine to produce Benzoic acid and Ecgonine methyl ester. Briefly, alternative substrates and inhibitors of cocaine, as well as compounds able to thermostabilize the enzyme, were investigated generally by substituting amide and thiol analogues at the reactive ester bond, or removing the bond (for inhibitors), substituting benzoyl analogues in place of the benzoic acid leaving group, and/or removing or altering the methyl-ester group on the ecgonine portion of the molecule. As discussed below, it was determined that some substrates, products, and inhibitors stabilized thermal denaturation of wild type CocE, as well as prevented thermally-induced aggregation in gel electrophoresis.

Figure 33:
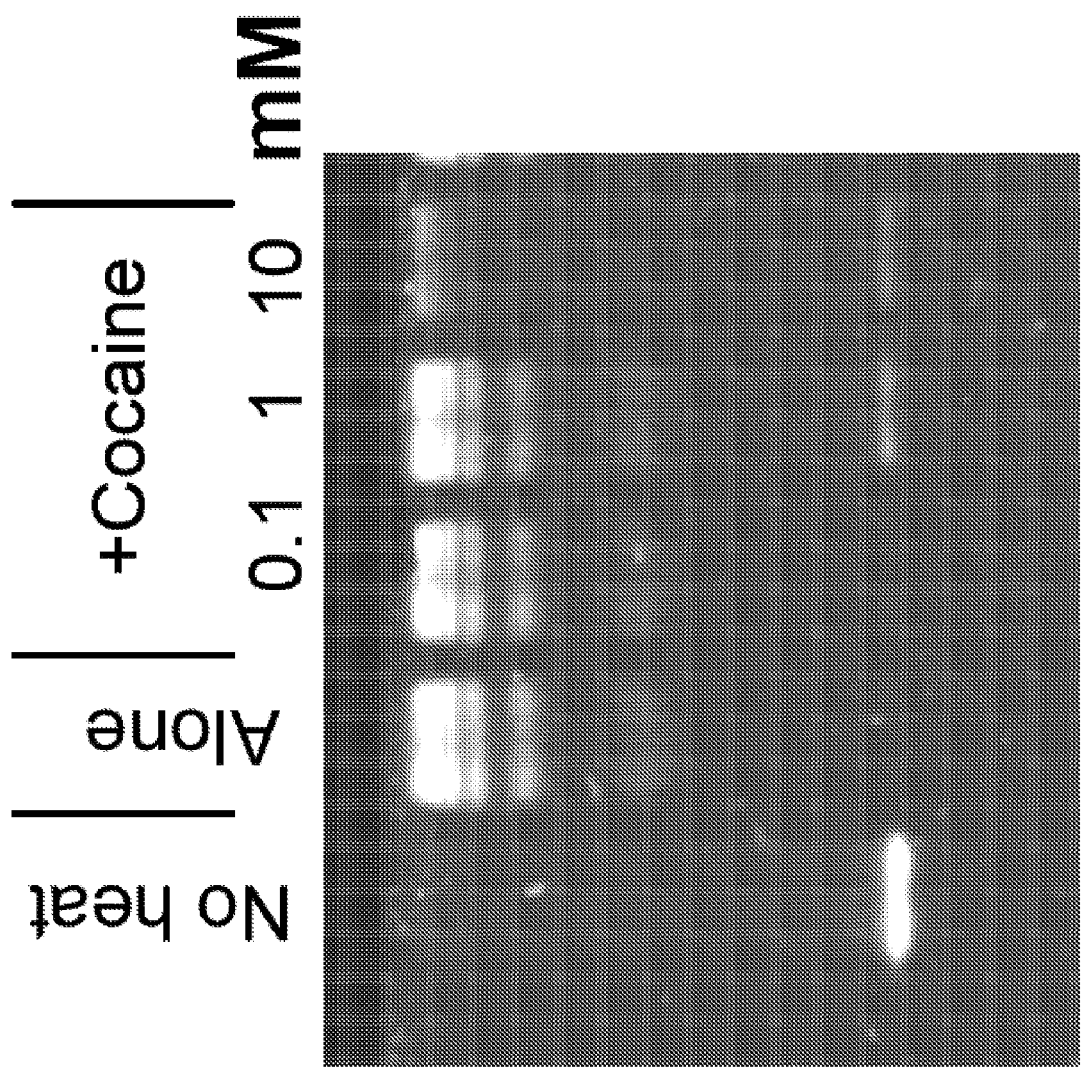
FIG. 33 is a picture of a gel showing that Cocaine (mM range prevented 37° C.-induced formation of high molecular weight CocE aggregates (0.1 mg/ml enzyme concentrations. For further methodology information, see Example 20.
Figure 34:
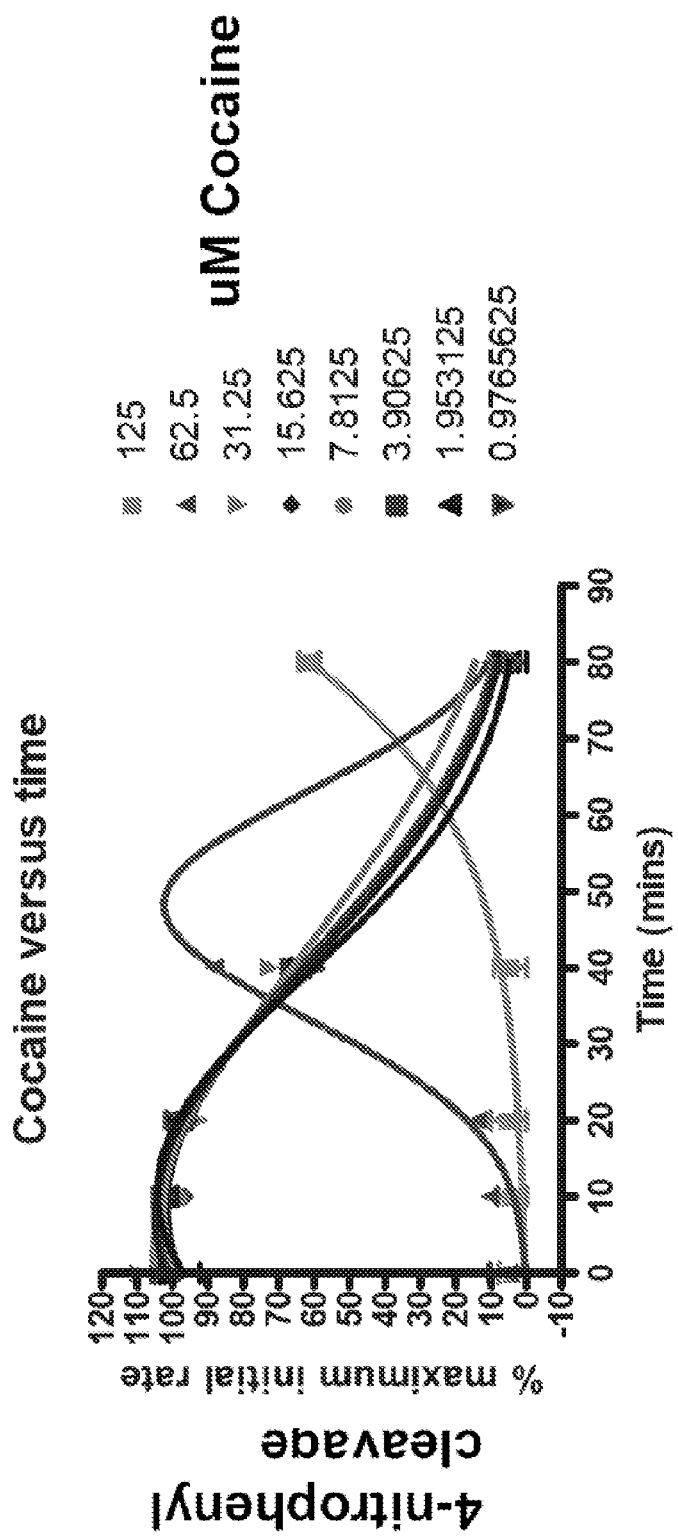
FIG. 34 is a line and scatter plot showing that Cocaine (uM quantities) stabilized 37° C.-induced activity loss. For further methodology information, see Example 20.

Cocaine is the natural substrate of Cocaine esterase (CocE). Cocaine cleavage was monitored by a drop in absorbance at 240 nm. Cocaine (mM range) prevented 37° C.-induced formation of high molecular weight CocE aggregates (0.1 mg/ml enzyme concentrations) (see, e.g., FIG. 33). Cocaine (uM quantities) stabilized 37° C.-induced activity loss (see, e.g., FIG. 34), although the mechanism of this stabilization is complicated due to substrate inhibition at higher concentrations.

Figure 35:
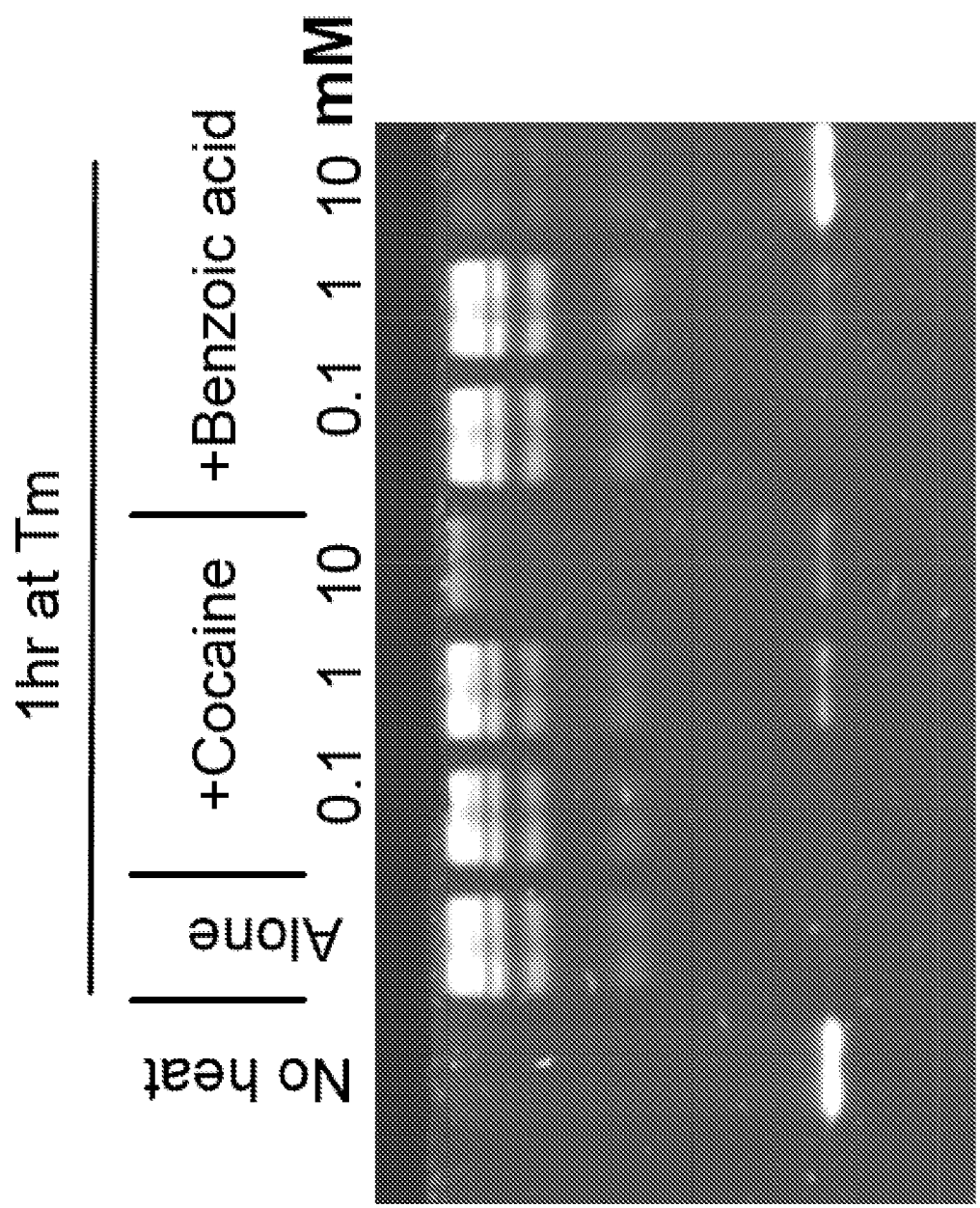
FIG. 35 is a picture of a gel showing that Benzoic acid (mM range prevented 37° C.-induced formation of high molecular weight CocE aggregates (0.1 mg/ml enzyme concentrations. For further methodology information, see Example 20.
Figure 36:
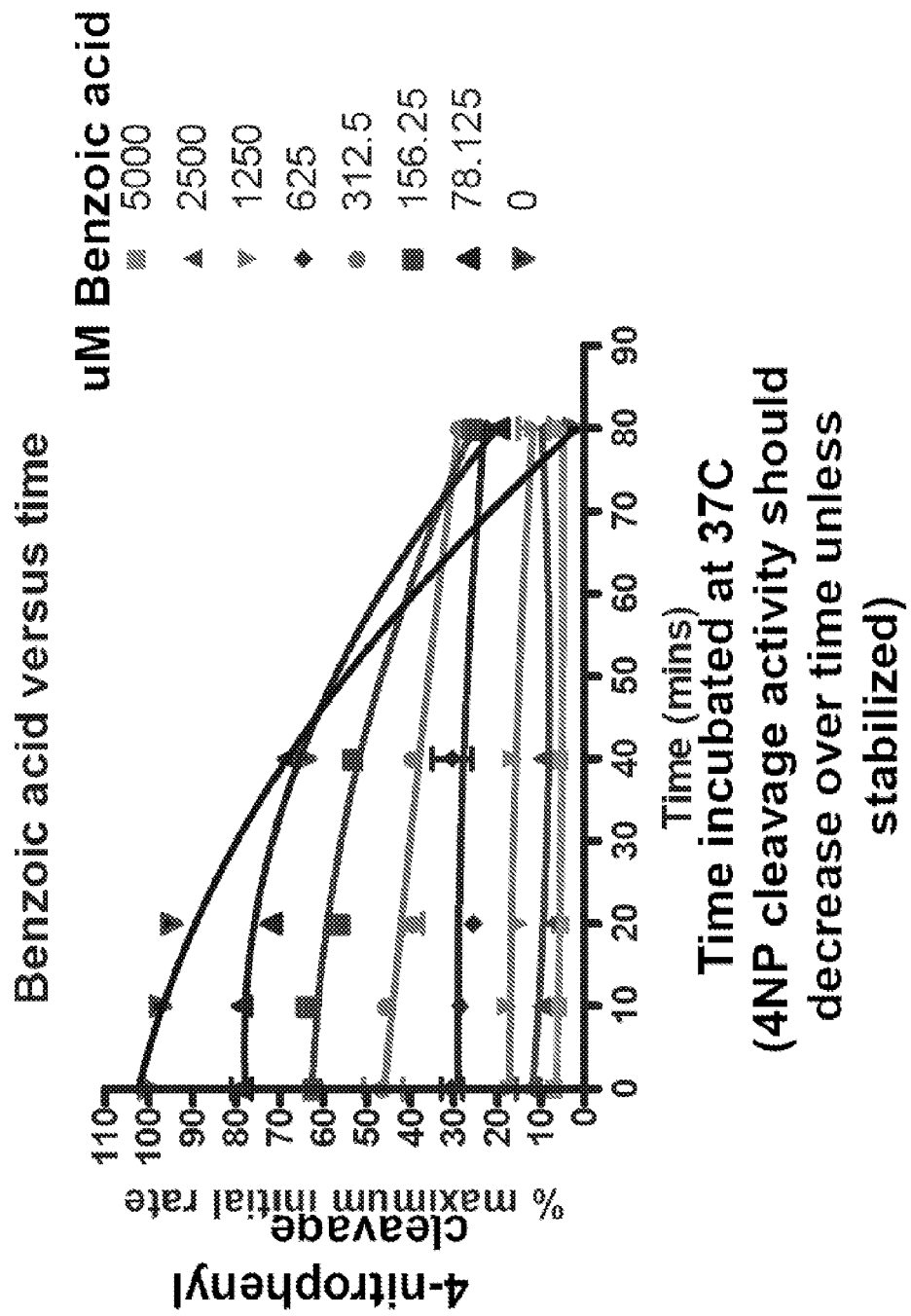
FIG. 36 is a line and scatter plot showing that Cocaine (uM quantities) stabilized 37° C.-induced activity loss. For further methodology information, see Example 20.

Benzoic acid is the natural product of CocE and a weak inhibitor of CocE cleavage of 4-nitrophenyl acetate (Ki 310 uM). Benzoic acid prevented 37° C.-induced formation of high molecular weight CocE aggregates (0.1 mg/ml enzyme concentrations) (see, e.g., FIG. 35). Benzoic acid (uM quantities) stabilized 37° C.-induced activity loss (see, e.g., FIG. 36), although the mechanism of this stabilization is complicated due to substrate inhibition at higher concentrations.

CocE catalyzes the cleavage of 4-nitrophenyl acetate (4NPA) to 4-nitrophenol (4NP) and acetate. The cleavage reaction was monitored by observation of product formation at 400 nm. Both 4NP and 4NPA (mM range) prevented 37° C.-induced formation of high molecular weight CocE aggregates (0.1 mg/ml enzyme concentrations).

Phenylboronic acid is a potent inhibitor of CocE (Ki 250 nM). Phenylboronic acid stabilized 37° C.-induced aggregation of CocE with an EC50 of 0.2 UM by densitometry analysis.

Using the above, a screening assay is developed to screen for small molecules that might similarly stabilize the enzyme but not necessarily occupy the active site. Molecules identified as stabilizing molecules are used to stabilize the proteins disclosed herein until ready for use.

What is claimed is:

1. An isolated mutant cocaine esterase (CocE) polypeptide comprising
an amino acid sequence at least 95% identical to SEQ ID NO: 1 having at least one substitution, addition or deletion,
wherein
the at least one substitution, addition or deletion is selected from the group consisting of L163V; V225I; I218L; A310D; A149S; S159A; S265A; S56G; W220A; S140A; F189L; A193D; T254R; N42V; V262L; L508G; Y152H; V160A; T172R; Y532F; T74S; W285T; L146P; D533S; A194R; G173Q; C477T; K531A; R41I; L119A; K46A; F84Y; T172R-G173Q; L169K; F189A; N197K; R182K; F189K; V190K; Q191K; A194K; I175-G-G-A186; and T176-G-G-D185; and
the mutant CocE polypeptide has esterase activity with increased thermostability at 37° C. as compared to wild-type CocE having the amino acid sequence of SEQ ID NO:1.

2. The mutant CocE polypeptide of claim 1, wherein at least two amino acid residues are substituted.

3. The mutant CocE polypeptide of claim 1, wherein at least three amino acid residues are substituted.

4. The mutant CocE polypeptide of claim 1, wherein at least four amino acid residues are substituted.

5. The mutant CocE polypeptide of claim 1, wherein at least five amino acid residues are substituted.

6. The mutant CocE polypeptide of claim 1, comprising an amino acid sequence selected from the group consisting of SEQ ID NO: 3 (L163V); SEQ ID NO: 7 (V225I); SEQ ID NO: 8 (I218L); SEQ ID NO: 9 (A310D); SEQ ID NO: 10 (A149S); SEQ ID NO: 11 (S159A); SEQ ID NO: 12 (S265A); SEQ ID NO: 13 (S56G); SEQ ID NO: 14 (W220A); SEQ ID NO: 16 (S140A); SEQ ID NO: 17 (F189L); SEQ ID NO: 18 (A193D); SEQ ID NO: 19 (T254R); SEQ ID NO: 20 (N42V); SEQ ID NO: 21 (V262L); SEQ ID NO: 22 (L508G); SEQ ID NO: 23 (Y152H); SEQ ID NO: 24 (V160A); SEQ ID NO: 25 (T172R); SEQ ID NO: 26 (Y532F); SEQ ID NO: 27 (T74S); SEQ ID NO: 28 (W285T); SEQ ID NO: 29 (L146P); SEQ ID NO: 30 (D533S); SEQ ID NO: 31 (A194R); SEQ ID NO: 32 (G173Q); SEQ ID NO: 33 (C477T); SEQ ID NO: 34 (K531A); SEQ ID NO: 35 (R41I); SEQ ID NO: 36 (L119A); SEQ ID NO: 37 (K46A); SEQ ID NO: 38 (F84Y), SEQ ID NO: 39 (T172R-G173Q); SEQ ID NO: 40 (L169K); SEQ ID NO: 41 (F189A), SEQ ID NO: 42 (N197K), SEQ ID NO: 43 (R182K), SEQ ID NO: 44 (F189K), SEQ ID NO: 45 (V190K), SEQ ID NO: 46 (Q191K), and SEQ ID NO: 47 (A194K).

7. An isolated nucleic acid encoding the mutant CocE polypeptide of claim 1.

8. An isolated nucleic acid encoding a mutant CocE polypeptide of claim 1, wherein the nucleic acid has at least 85% sequence identity with SEQ ID NO: 2, and wherein the encoded mutant CocE polypeptide has esterase activity with increased thermostability at 37° C. as compared to wild-type CocE having the amino acid sequence of SEQ ID NO:1.

9. The isolated nucleic acid of claim 8 wherein the sequence identity is at least 90%.

10. The mutant CocE polypeptide of claim 1 wherein the increase in thermostability of the mutant CocE polypeptide over wild-type CocE having the amino acid sequence of SEQ ID NO:1 is about 2.1 kcal/mol or greater.

11. The polypeptide claim 1 wherein the mutant CocE polypeptide has at least about 60% or greater of the esterase activity of wild-type CocE polypeptide.

12. A pharmaceutical composition comprising the mutant CocE polypeptide of claim 1 and a pharmaceutically acceptable carrier or excipient.

13. The mutant CocE polypeptide of claim 1, wherein the mutant CocE polypeptide is pegylated.

14. The mutant CocE polypeptide of claim 1, stabilized by a substrate or inhibitor.

15. The mutant CocE polypeptide of claim 1, comprising a substitution, addition or deletion of T172R; F189A; A193D; G173Q; G173Q-I175-G-G-A186; G173Q-T176-G-G-D185; L169K; or F189K.

16. A method of treating a cocaine-induced condition comprising administering to a subject in need thereof an amount of the mutant CocE polypeptide of claim 1 effective to treat the cocaine-induced condition.

17. The method of claim 16, wherein the cocaine-induced condition is selected from the group consisting of cocaine overdose, cocaine toxicity, cocaine addiction, and cocaine dependence.

18. The mutant CocE polypeptide of claim 1, encoded by a nucleic acid having at least 85% sequence identity with SEQ ID NO:2.

19. The pharmaceutical composition of claim 12, suitable for parenteral administration.

20. The mutant CocE polypeptide of claim 15, comprising a substitution, addition or deletion of F189A/T172R; T172R/A193D; T172R/G173Q; T172R/G173Q-I175-G-G-A186; or T172R/G173Q-T176-G-G-D185.

* * * * *